United States Patent
Shelton, IV et al.

(10) Patent No.: US 11,882,987 B2
(45) Date of Patent: Jan. 30, 2024

(54) ARTICULATING SURGICAL STAPLING INSTRUMENT INCORPORATING A TWO-PIECE E-BEAM FIRING MECHANISM

(71) Applicant: Cilag GmbH International, Zug (CH)

(72) Inventors: Frederick E. Shelton, IV, Hillsboro, OH (US); Michael E. Setser, Burlington, KY (US); William B. Weisenburgh, II, Maineville, OH (US)

(73) Assignee: Cilag GmbH International, Zug (CH)

(*) Notice: Subject to any disclaimer, the term of this patent is extended or adjusted under 35 U.S.C. 154(b) by 146 days.

(21) Appl. No.: 16/929,396

(22) Filed: Jul. 15, 2020

(65) Prior Publication Data
US 2021/0000467 A1 Jan. 7, 2021

Related U.S. Application Data

(63) Continuation of application No. 16/384,096, filed on Apr. 15, 2019, which is a continuation of application
(Continued)

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/064* (2013.01); *A61B 17/068* (2013.01);
(Continued)

(58) Field of Classification Search
CPC ............ A61B 17/07207; A61B 17/068; A61B 17/072; A61B 17/105; A61B 2017/07257;
(Continued)

(56) References Cited

U.S. PATENT DOCUMENTS

| 66,052 A | 6/1867 | Smith |
|---|---|---|
| 662,587 A | 11/1900 | Blake |

(Continued)

FOREIGN PATENT DOCUMENTS

| AU | 2012200594 A1 | 2/2012 |
|---|---|---|
| AU | 2012203035 A1 | 6/2012 |

(Continued)

OTHER PUBLICATIONS

Arjo Loeve et al., Scopes Too Flexible . . . And Too Stiff, 2010, IEEE Pulse, Nov./Dec. 2010 (Year: 2010), 16 pages.
(Continued)

*Primary Examiner* — Michelle Lopez

(57) ABSTRACT

A surgical severing and stapling instrument, suitable for laparoscopic and endoscopic clinical procedures, clamps tissue within an end effector of an elongate channel pivotally opposed by an anvil. An E-beam firing bar moves distally through the clamped end effector to sever tissue and to drive staples on each side of the cut. The E-beam firing bar affirmatively spaces the anvil from the elongate channel to assure properly formed closed staples, especially when an amount of tissue is clamped that is inadequate to space the end effector. In particular, an upper pin of the firing bar longitudinally moves through an anvil slot and a channel slot is captured between a lower cap and a middle pin of the firing bar to assure a minimum spacing. Forming the E-beam from a thickened distal portion and a thinned proximal strip enhances manufacturability and facilitates use in such articulating surgical instruments.

21 Claims, 13 Drawing Sheets

Related U.S. Application Data

No. 15/679,300, filed on Aug. 17, 2017, now Pat. No. 10,292,707, which is a continuation of application No. 14/850,030, filed on Sep. 10, 2015, now Pat. No. 9,737,303, which is a continuation of application No. 14/521,748, filed on Oct. 23, 2014, now Pat. No. 9,510,830, which is a continuation of application No. 14/175,148, filed on Feb. 7, 2014, now Pat. No. 9,282,966, which is a continuation-in-part of application No. 13/369,601, filed on Feb. 9, 2012, now Pat. No. 8,783,541, which is a continuation of application No. 13/118,246, filed on May 27, 2011, now Pat. No. 9,060,770, which is a continuation-in-part of application No. 11/538,154, filed on Oct. 3, 2006, now abandoned, application No. 16/929,396, filed on Jul. 15, 2020 is a continuation of application No. 16/384,096, filed on Apr. 15, 2019, now Pat. No. 10,292,707, which is a continuation of application No. 14/850,030, filed on Sep. 10, 2015, now Pat. No. 9,737,303, which is a continuation of application No. 14/521,748, filed on Oct. 23, 2014, now Pat. No. 9,510,830, which is a continuation of application No. 14/175,148, filed on Feb. 7, 2014, now Pat. No. 9,282,966, which is a continuation-in-part of application No. 11/141,753, filed on Jun. 1, 2005, now Pat. No. 8,905,977.

(60) Provisional application No. 60/591,694, filed on Jul. 28, 2004.

(51) Int. Cl.

| | |
|---|---|
| *A61B 34/30* | (2016.01) |
| *A61B 50/20* | (2016.01) |
| *A61B 17/064* | (2006.01) |
| *A61B 17/10* | (2006.01) |
| *A61B 17/32* | (2006.01) |
| *A61B 17/29* | (2006.01) |
| *A61B 34/37* | (2016.01) |
| *A61B 50/36* | (2016.01) |
| *A61B 18/14* | (2006.01) |
| *A61B 17/00* | (2006.01) |
| *A61B 18/00* | (2006.01) |

(52) U.S. Cl.
CPC ........ *A61B 17/0682* (2013.01); *A61B 17/072* (2013.01); *A61B 17/105* (2013.01); *A61B 17/320092* (2013.01); *A61B 34/30* (2016.02); *A61B 50/20* (2016.02); *A61B 18/1445* (2013.01); *A61B 34/37* (2016.02); *A61B 50/36* (2016.02); *A61B 2017/00017* (2013.01); *A61B 2017/00398* (2013.01); *A61B 2017/00473* (2013.01); *A61B 2017/00734* (2013.01); *A61B 2017/0688* (2013.01); *A61B 2017/07257* (2013.01); *A61B 2017/07271* (2013.01); *A61B 2017/07278* (2013.01); *A61B 2017/07285* (2013.01); *A61B 2017/2923* (2013.01); *A61B 2017/2927* (2013.01); *A61B 2017/320052* (2013.01); *A61B 2017/320093* (2017.08); *A61B 2017/320094* (2017.08); *A61B 2017/320095* (2017.08); *A61B 2017/320097* (2017.08); *A61B 2018/0063* (2013.01); *A61B 2034/302* (2016.02)

(58) Field of Classification Search
CPC ........... A61B 2017/07271; A61B 2017/07278; A61B 2017/07285

USPC ...................................................... 227/176.1
See application file for complete search history.

(56) References Cited

U.S. PATENT DOCUMENTS

| | | |
|---|---|---|
| 670,748 A | 3/1901 | Weddeler |
| 719,487 A | 2/1903 | Hutchinson |
| 804,229 A | 11/1905 | Hutchinson |
| 903,739 A | 11/1908 | Lesemann |
| 951,393 A | 3/1910 | Hahn |
| 1,075,556 A | 10/1913 | Fenoughty |
| 1,082,105 A | 12/1913 | Anderson |
| 1,188,721 A | 6/1916 | Bittner |
| 1,306,107 A | 6/1919 | Elliott |
| 1,314,601 A | 9/1919 | McCaskey |
| 1,466,128 A | 8/1923 | Hallenbeck |
| 1,677,337 A | 7/1928 | Grove |
| 1,794,907 A | 3/1931 | Kelly |
| 1,849,427 A | 3/1932 | Hook |
| 1,912,783 A | 6/1933 | Meyer |
| 1,944,116 A | 1/1934 | Stratman |
| 1,954,048 A | 4/1934 | Jeffrey et al. |
| 2,028,635 A | 1/1936 | Wappler |
| 2,037,727 A | 4/1936 | La Chapelle |
| 2,120,951 A | 6/1938 | Hodgman |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,108 A | 12/1940 | Ridgway |
| 2,224,882 A | 12/1940 | Peck |
| 2,256,295 A | 9/1941 | Schmid |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Royal Lee |
| 2,420,552 A | 5/1947 | Morrill |
| 2,441,096 A | 5/1948 | Happe |
| 2,448,741 A | 9/1948 | Scott et al. |
| 2,450,527 A | 10/1948 | Smith |
| 2,491,872 A | 12/1949 | Neuman |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,724,289 A | 11/1955 | Wight |
| 2,742,955 A | 4/1956 | Dominguez |
| 2,804,848 A | 9/1957 | O'Farrell et al. |
| 2,808,482 A | 10/1957 | Zanichkowsky et al. |
| 2,825,178 A | 3/1958 | Hawkins |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,026,744 A | 3/1962 | Rouse |
| 3,032,769 A | 5/1962 | Palmer |
| 3,035,256 A | 5/1962 | Egbert |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,252,643 A | 5/1966 | Strekopytov et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |

(56) References Cited

U.S. PATENT DOCUMENTS

| | | |
|---|---|---|
| 3,315,863 A | 4/1967 | O'Dea |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,604,561 A | 9/1971 | Mallina et al. |
| 3,608,549 A | 9/1971 | Merrill |
| 3,616,278 A | 10/1971 | Jansen |
| 3,618,842 A | 11/1971 | Bryan |
| 3,635,394 A | 1/1972 | Natelson |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,339 A | 5/1972 | Shimizu |
| 3,661,666 A | 5/1972 | Foster et al. |
| 3,662,939 A | 5/1972 | Bryan |
| 3,685,250 A | 8/1972 | Henry et al. |
| 3,688,966 A | 9/1972 | Perkins et al. |
| 3,692,224 A | 9/1972 | Astafiev et al. |
| 3,695,646 A | 10/1972 | Mommsen |
| 3,709,221 A | 1/1973 | Riely |
| 3,717,294 A | 2/1973 | Green |
| 3,724,237 A | 4/1973 | Wood |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,797,494 A | 3/1974 | Zaffaroni |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,822,818 A | 7/1974 | Strekopytov et al. |
| 3,825,007 A | 7/1974 | Rand |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,863,940 A | 2/1975 | Cummings |
| 3,883,624 A | 5/1975 | McKenzie et al. |
| 3,885,491 A | 5/1975 | Curtis |
| 3,887,393 A | 6/1975 | La Rue, Jr. |
| 3,892,228 A | 7/1975 | Mitsui |
| 3,894,174 A | 7/1975 | Cartun |
| 3,899,829 A | 8/1975 | Storm et al. |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,973,179 A | 8/1976 | Weber et al. |
| 3,981,051 A | 9/1976 | Brumlik |
| 3,993,072 A | 11/1976 | Zaffaroni |
| 3,999,110 A | 12/1976 | Ramstrom et al. |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,047,654 A | 9/1977 | Alvarado |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,149,461 A | 4/1979 | Simeth |
| 4,154,122 A | 5/1979 | Severin |
| 4,160,857 A | 7/1979 | Nardella et al. |
| 4,169,476 A | 10/1979 | Hiltebrandt |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,191,377 A | 3/1980 | Burnside |
| 4,198,734 A | 4/1980 | Brumlik |
| 4,198,982 A | 4/1980 | Fortner et al. |
| 4,203,444 A | 5/1980 | Bonnell et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,250,817 A | 2/1981 | Michel |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,282,573 A | 8/1981 | Imai et al. |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |

(56) References Cited

U.S. PATENT DOCUMENTS

| | | |
|---|---|---|
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,389,963 A | 6/1983 | Pearson |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,421,264 A | 12/1983 | Arter et al. |
| 4,423,456 A | 12/1983 | Zaidenweber |
| 4,425,915 A | 1/1984 | Ivanov |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,459,519 A | 7/1984 | Erdman |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A * | 9/1984 | Noiles .................. A61B 17/115 227/19 |
| 4,475,679 A | 10/1984 | Fleury, Jr. |
| 4,476,864 A | 10/1984 | Tezel |
| 4,478,220 A | 10/1984 | Di Giovanni et al. |
| 4,480,641 A | 11/1984 | Failla et al. |
| 4,481,458 A | 11/1984 | Lane |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,514,477 A | 4/1985 | Kobayashi |
| 4,520,817 A | 6/1985 | Green |
| 4,522,327 A | 6/1985 | Korthoff et al. |
| 4,523,707 A | 6/1985 | Blake, III et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,980 A | 9/1986 | Aihara |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,617,935 A | 10/1986 | Cartmell et al. |
| 4,619,262 A | 10/1986 | Taylor |
| 4,619,391 A | 10/1986 | Sharkany et al. |
| 4,624,401 A | 11/1986 | Gassner et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,642,738 A | 2/1987 | Meller |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,651,734 A | 3/1987 | Doss et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |

(56) References Cited

U.S. PATENT DOCUMENTS

| | | |
|---|---|---|
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,726,247 A | 2/1988 | Hormann |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,755,070 A | 7/1988 | Cerutti |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,788,978 A | 12/1988 | Strekopytov et al. |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,495 A | 4/1989 | Hormann |
| 4,819,853 A | 4/1989 | Green |
| 4,821,939 A | 4/1989 | Green |
| 4,827,552 A | 5/1989 | Bojar et al. |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,096 A | 5/1989 | Oh et al. |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,868,958 A | 9/1989 | Suzuki et al. |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |
| 4,919,039 A | 4/1990 | Nutter |
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | LeVahn et al. |
| 4,949,927 A | 8/1990 | Madocks et al. |
| 4,950,268 A | 8/1990 | Rink |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,681 A | 10/1990 | Yang |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,976,173 A | 12/1990 | Yang |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,222 A | 4/1991 | Her |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,019,077 A | 5/1991 | De Bastiani et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,033,552 A | 7/1991 | Hu |
| 5,035,040 A | 7/1991 | Kerrigan et al. |
| 5,037,018 A | 8/1991 | Matsuda et al. |
| 5,038,109 A | 8/1991 | Goble et al. |
| 5,038,247 A | 8/1991 | Kelley et al. |

(56) References Cited

U.S. PATENT DOCUMENTS

| | | |
|---|---|---|
| 5,040,715 A | 8/1991 | Green et al. |
| 5,042,707 A | 8/1991 | Taheri |
| 5,056,953 A | 10/1991 | Marot et al. |
| 5,060,658 A | 10/1991 | Dejter, Jr. et al. |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,100,422 A | 3/1992 | Berguer et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,135,483 A | 8/1992 | Wagner et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,151,102 A | 9/1992 | Kamiyama et al. |
| 5,155,941 A | 10/1992 | Takahashi et al. |
| 5,156,151 A | 10/1992 | Imran |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |
| 5,158,567 A | 10/1992 | Green |
| D330,699 S | 11/1992 | Gill |
| 5,163,598 A | 11/1992 | Peters et al. |
| 5,163,842 A | 11/1992 | Nonomura |
| 5,164,652 A | 11/1992 | Johnson et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,180,375 A | 1/1993 | Feibus |
| 5,181,514 A | 1/1993 | Solomon et al. |
| 5,187,422 A | 2/1993 | Izenbaard et al. |
| 5,188,102 A | 2/1993 | Idemoto et al. |
| 5,188,111 A | 2/1993 | Yates et al. |
| 5,188,126 A | 2/1993 | Fabian et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,236,629 A | 8/1993 | Mahabadi et al. |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,251,801 A | 10/1993 | Ruckdeschel et al. |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,269,794 A | 12/1993 | Rexroth |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,281,400 A | 1/1994 | Berry, Jr. |
| 5,282,806 A | 2/1994 | Haber et al. |
| 5,282,826 A | 2/1994 | Quadri |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,291,133 A | 3/1994 | Gokhale et al. |

(56) References Cited

U.S. PATENT DOCUMENTS

| | | |
|---|---|---|
| 5,292,053 A | 3/1994 | Bilotti et al. |
| 5,293,024 A | 3/1994 | Sugahara et al. |
| 5,297,714 A | 3/1994 | Kramer |
| 5,300,087 A | 4/1994 | Knoepfler |
| 5,302,148 A | 4/1994 | Heinz |
| 5,303,606 A | 4/1994 | Kokinda |
| 5,304,204 A | 4/1994 | Bregen |
| D347,474 S | 5/1994 | Olson |
| 5,307,976 A | 5/1994 | Olson et al. |
| 5,308,353 A | 5/1994 | Beurrier |
| 5,308,358 A | 5/1994 | Bond et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,318,589 A | 6/1994 | Lichtman |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,486 A | 7/1994 | Wilk |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,338,317 A | 8/1994 | Hasson et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,104 A | 9/1994 | Main et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,353,798 A | 10/1994 | Sieben |
| 5,354,215 A | 10/1994 | Viracola |
| 5,354,250 A | 10/1994 | Christensen |
| 5,354,303 A | 10/1994 | Spaeth et al. |
| 5,355,897 A | 10/1994 | Pietrafitta et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,368,599 A | 11/1994 | Hirsch et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |
| 5,381,943 A | 1/1995 | Allen et al. |
| 5,382,247 A | 1/1995 | Cimino et al. |
| 5,383,460 A | 1/1995 | Jang et al. |
| 5,383,738 A | 1/1995 | Herbermann |
| 5,383,874 A | 1/1995 | Jackson et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,388,748 A | 2/1995 | Davignon et al. |
| 5,389,072 A | 2/1995 | Imran |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |

(56) References Cited

U.S. PATENT DOCUMENTS

| | | |
|---|---|---|
| 5,423,471 A | 6/1995 | Mastri et al. |
| 5,423,809 A | 6/1995 | Klicek |
| 5,423,835 A | 6/1995 | Green et al. |
| 5,425,355 A | 6/1995 | Kulick |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,645 A | 7/1995 | Smith et al. |
| 5,431,654 A | 7/1995 | Nic |
| 5,431,666 A | 7/1995 | Sauer et al. |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,441,499 A | 8/1995 | Fritzsch |
| 5,443,197 A | 8/1995 | Malis et al. |
| 5,443,198 A | 8/1995 | Viola et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,824 A | 10/1995 | Fontayne et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,474,738 A | 12/1995 | Nichols et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,308 A | 12/1995 | Cartmell et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,377 A | 1/1996 | Smith et al. |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,164 A | 3/1996 | Ward et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,507,773 A | 4/1996 | Huitema et al. |
| 5,508,080 A | 4/1996 | Sorimachi et al. |
| 5,509,596 A | 4/1996 | Green et al. |
| 5,509,916 A | 4/1996 | Taylor |
| 5,509,918 A | 4/1996 | Romano |
| 5,510,138 A | 4/1996 | Sanftleben et al. |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,945 A | 8/1996 | Fritzsch |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |

(56) References Cited

U.S. PATENT DOCUMENTS

| | | |
|---|---|---|
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,694 A | 10/1996 | Sauer et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,303 A | 3/1997 | Nakamura |
| 5,607,433 A | 3/1997 | Polla et al. |
| 5,607,436 A | 3/1997 | Pratt et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,611,813 A | 3/1997 | Lichtman |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,415 A | 4/1997 | Lucey et al. |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,979 A | 5/1997 | Mitsui et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,631,973 A | 5/1997 | Green |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |
| 5,636,780 A | 6/1997 | Green et al. |
| 5,637,110 A | 6/1997 | Pennybacker et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,656,917 A | 8/1997 | Theobald |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,664,404 A | 9/1997 | Ivanov et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |

(56) References Cited

U.S. PATENT DOCUMENTS

| | | |
|---|---|---|
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,184 A | 10/1997 | Hassler, Jr. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,683,432 A | 11/1997 | Goedeke et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,265 A | 12/1997 | Romano |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,704,792 A | 1/1998 | Sobhani |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,711,960 A | 1/1998 | Shikinami |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,836 A | 2/1998 | Kliegis et al. |
| 5,715,987 A | 2/1998 | Kelley et al. |
| 5,715,988 A | 2/1998 | Palmer |
| 5,716,352 A | 2/1998 | Viola et al. |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,712 A | 3/1998 | Adair |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,736,271 A | 4/1998 | Cisar et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,746,770 A | 5/1998 | Zeitels et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,755,726 A | 5/1998 | Pratt et al. |
| 5,758,814 A | 6/1998 | Gallagher et al. |
| 5,762,255 A | 6/1998 | Chrisman et al. |
| 5,762,256 A | 6/1998 | Mastri et al. |
| 5,762,458 A | 6/1998 | Wang et al. |
| 5,765,565 A | 6/1998 | Adair |
| 5,766,186 A | 6/1998 | Faraz et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,640 A | 6/1998 | Jacobus et al. |
| 5,769,748 A | 6/1998 | Eyerly et al. |
| 5,769,791 A | 6/1998 | Benaron et al. |
| 5,769,892 A | 6/1998 | Kingwell |
| 5,772,099 A | 6/1998 | Gravener |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,798,752 A | 8/1998 | Buxton et al. |
| 5,799,857 A | 9/1998 | Robertson et al. |
| 5,800,379 A | 9/1998 | Edwards |
| 5,800,423 A | 9/1998 | Jensen |

(56) References Cited

U.S. PATENT DOCUMENTS

| | | |
|---|---|---|
| 5,804,726 A | 9/1998 | Geib et al. |
| 5,804,936 A | 9/1998 | Brodsky et al. |
| 5,806,676 A | 9/1998 | Wasgien |
| 5,807,241 A | 9/1998 | Heimberger |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,240 A | 9/1998 | Robertson |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A * | 2/1999 | Milliman .............. A61B 17/068 227/176.1 |
| 5,865,638 A | 2/1999 | Trafton |
| 5,868,361 A | 2/1999 | Rinderer |
| 5,868,664 A | 2/1999 | Speier et al. |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,881,943 A | 3/1999 | Heck et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,855 A | 4/1999 | Jacobs |
| 5,893,863 A | 4/1999 | Yoon |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,907,664 A | 5/1999 | Wang et al. |
| 5,908,149 A | 6/1999 | Welch et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,922,001 A | 7/1999 | Yoon |
| 5,922,003 A | 7/1999 | Anctil et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,980,569 A | 11/1999 | Scirica |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |

(56) References Cited

U.S. PATENT DOCUMENTS

| | | |
|---|---|---|
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,013,991 A | 1/2000 | Philipp |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,019,780 A | 2/2000 | Lombardo et al. |
| 6,022,352 A | 2/2000 | Vandewalle |
| 6,023,275 A | 2/2000 | Horvitz et al. |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,031,148 A | 2/2000 | Hayes et al. |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,126 A | 3/2000 | Hsieh |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,072,299 A | 6/2000 | Kurle et al. |
| 6,074,386 A | 6/2000 | Goble et al. |
| 6,074,401 A | 6/2000 | Gardiner et al. |
| 6,075,441 A | 6/2000 | Maloney |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,090,123 A | 7/2000 | Culp et al. |
| 6,093,186 A | 7/2000 | Goble |
| 6,094,021 A | 7/2000 | Noro et al. |
| D429,252 S | 8/2000 | Haitani et al. |
| 6,099,537 A | 8/2000 | Sugai et al. |
| 6,099,551 A | 8/2000 | Gabbay |
| 6,102,271 A | 8/2000 | Longo et al. |
| 6,102,926 A | 8/2000 | Tartaglia et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| RE36,923 E | 10/2000 | Hiroi et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,148,979 A | 11/2000 | Roach et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,083 A | 12/2000 | Goeser et al. |
| 6,155,473 A | 12/2000 | Tompkins et al. |
| 6,156,056 A | 12/2000 | Kearns et al. |
| 6,157,169 A | 12/2000 | Lee |
| 6,157,303 A | 12/2000 | Bodie et al. |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |

(56) References Cited

U.S. PATENT DOCUMENTS

| | | |
|---|---|---|
| 6,186,142 B1 | 2/2001 | Schmidt et al. |
| 6,186,957 B1 | 2/2001 | Milam |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,311 B1 | 3/2001 | Danek et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,211,626 B1 | 4/2001 | Lys et al. |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,235,036 B1 | 5/2001 | Gardner et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,246 B1 | 7/2001 | Pantages et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,269,997 B1 | 8/2001 | Balazs et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,317,616 B1 | 11/2001 | Glossop |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,338,738 B1 | 1/2002 | Bellotti et al. |
| 6,343,731 B1 | 2/2002 | Adams et al. |
| 6,346,077 B1 | 2/2002 | Taylor et al. |
| 6,348,061 B1 | 2/2002 | Whitman |
| 6,349,868 B1 | 2/2002 | Mattingly et al. |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,361,542 B1 | 3/2002 | Dimitriu et al. |
| 6,364,828 B1 | 4/2002 | Yeung et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| 6,406,440 B1 | 6/2002 | Stefanchik |
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |

(56) References Cited

U.S. PATENT DOCUMENTS

| | | |
|---|---|---|
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,656 B2 | 9/2002 | Brissette et al. |
| 6,454,781 B1 | 9/2002 | Witt et al. |
| 6,457,338 B1 | 10/2002 | Frenken |
| 6,457,625 B1 | 10/2002 | Tormala et al. |
| 6,458,077 B1 | 10/2002 | Boebel et al. |
| 6,458,142 B1 | 10/2002 | Faller et al. |
| 6,458,147 B1 | 10/2002 | Cruise et al. |
| 6,460,627 B1 | 10/2002 | Below et al. |
| 6,463,824 B1 | 10/2002 | Prell et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,063 B1 | 11/2002 | Frigard |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,189 B1 | 12/2002 | Lang et al. |
| 6,500,194 B2 | 12/2002 | Benderev et al. |
| D468,749 S | 1/2003 | Friedman |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,506,399 B2 | 1/2003 | Donovan |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| D471,206 S | 3/2003 | Buzzard et al. |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,844 B2 | 4/2003 | Lee et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,569,173 B1 | 5/2003 | Blatter et al. |
| 6,572,629 B2 | 6/2003 | Kalloo et al. |
| 6,575,969 B1 | 6/2003 | Rittman, III et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,572 B1 | 7/2003 | Suzuta |
| 6,592,597 B2 | 7/2003 | Grant et al. |
| 6,594,552 B1 | 7/2003 | Nowlin et al. |
| 6,595,914 B2 | 7/2003 | Kato |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,623,482 B2 | 9/2003 | Pendekanti et al. |
| 6,625,517 B1 | 9/2003 | Bogdanov et al. |
| 6,626,834 B2 | 9/2003 | Dunne et al. |
| 6,626,901 B1 | 9/2003 | Treat et al. |
| 6,626,938 B1 | 9/2003 | Butaric et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |

(56) References Cited

U.S. PATENT DOCUMENTS

| | | |
|---|---|---|
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B2 | 3/2004 | Pedicini et al. |
| 6,709,445 B2 | 3/2004 | Boebel et al. |
| 6,712,773 B1 | 3/2004 | Viola |
| 6,716,215 B1 | 4/2004 | David et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,106 B1 | 4/2004 | Charles et al. |
| 6,723,109 B2 | 4/2004 | Solingen |
| 6,726,651 B1 | 4/2004 | Robinson et al. |
| 6,726,697 B2 | 4/2004 | Nicholas et al. |
| 6,726,705 B2 | 4/2004 | Peterson et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,810 B2 | 5/2004 | Hoey et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,825 B2 | 6/2004 | Shoenman et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,763,307 B2 | 7/2004 | Berg et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,773,458 B1 | 8/2004 | Brauker et al. |
| 6,775,575 B2 | 8/2004 | Bommannan et al. |
| 6,777,838 B2 | 8/2004 | Miekka et al. |
| 6,778,846 B1 | 8/2004 | Martinez et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,784,775 B2 | 8/2004 | Mandell et al. |
| 6,786,382 B1 | 9/2004 | Hoffman |
| 6,786,864 B2 | 9/2004 | Matsuura et al. |
| 6,786,896 B2 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,801,009 B2 | 10/2004 | Makaran et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,806,867 B1 | 10/2004 | Arruda et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |

(56) References Cited

U.S. PATENT DOCUMENTS

| | | |
|---|---|---|
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,860,169 B2 | 3/2005 | Shinozaki |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,876,850 B2 | 4/2005 | Maeshima et al. |
| 6,877,647 B2 | 4/2005 | Green et al. |
| 6,878,106 B1 | 4/2005 | Herrmann |
| 6,882,127 B2 | 4/2005 | Konigbauer |
| 6,883,199 B1 | 4/2005 | Lundell et al. |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,244 B1 | 5/2005 | Walker et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,705 B2 | 5/2005 | Niemeyer |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,927,315 B1 | 8/2005 | Heinecke et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,949,196 B2 | 9/2005 | Schmitz et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| 6,958,070 B2 | 10/2005 | Witt et al. |
| D511,525 S | 11/2005 | Hernandez et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,991,146 B2 | 1/2006 | Sinisi et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 6,999,821 B2 | 2/2006 | Jenney et al. |
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,005,828 B2 | 2/2006 | Karikomi |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,213 B2 | 3/2006 | Clark et al. |
| 7,011,657 B2 | 3/2006 | Truckai et al. |

(56) References Cited

U.S. PATENT DOCUMENTS

| | | |
|---|---|---|
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,399 B2 | 4/2006 | Driessen |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,033,378 B2 | 4/2006 | Smith et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,038,421 B2 | 5/2006 | Trifilo |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,716 B1 | 5/2006 | Kucharczyk et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,123 B2 | 6/2006 | Gregorio et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,412 B1 | 7/2006 | Reynolds et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,081,318 B2 | 7/2006 | Lee et al. |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | DeLuca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,363 B2 | 9/2006 | Nishizawa et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,201 B2 | 9/2006 | Truckai et al. |
| 7,112,214 B2 | 9/2006 | Peterson et al. |
| RE39,358 E | 10/2006 | Goble |
| D530,339 S | 10/2006 | Hernandez et al. |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |
| 7,153,300 B2 | 12/2006 | Goble |
| 7,153,314 B2 | 12/2006 | Laufer et al. |
| 7,155,316 B2 | 12/2006 | Sutherland et al. |
| 7,156,846 B2 | 1/2007 | Dycus et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,160,311 B2 | 1/2007 | Blatter et al. |

(56) References Cited

U.S. PATENT DOCUMENTS

| | | |
|---|---|---|
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,117 B2 | 1/2007 | Hellenkamp |
| 7,166,133 B2 | 1/2007 | Evans et al. |
| 7,168,604 B2 | 1/2007 | Milliman et al. |
| 7,169,146 B2 | 1/2007 | Truckai et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,197,965 B1 | 4/2007 | Anderson |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,205,959 B2 | 4/2007 | Henriksson |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,226,467 B2 | 6/2007 | Lucatero et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| 7,273,488 B2 | 9/2007 | Nakamura et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,311,709 B2 | 12/2007 | Truckai et al. |
| 7,313,430 B2 | 12/2007 | Urquhart et al. |
| 7,314,473 B2 | 1/2008 | Jinno et al. |
| 7,317,955 B2 | 1/2008 | McGreevy |
| 7,320,704 B2 | 1/2008 | Lashinski et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,183 B2 | 2/2008 | Reddy et al. |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |

(56) References Cited

U.S. PATENT DOCUMENTS

| | | |
|---|---|---|
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,398 B2 | 4/2008 | Kanazawa |
| 7,354,440 B2 | 4/2008 | Truckal et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,367,973 B2 | 5/2008 | Manzo et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| D570,868 S | 6/2008 | Hosokawa et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| D575,793 S | 8/2008 | Ording |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,422,582 B2 | 9/2008 | Malackowski et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,430,849 B1 | 10/2008 | Coutts et al. |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| D580,942 S | 11/2008 | Oshiro et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,450,991 B2 | 11/2008 | Smith et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,455,687 B2 | 11/2008 | Saunders et al. |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,147 B2 | 1/2009 | Honeycutt et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,492,261 B2 | 2/2009 | Cambre et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,497,137 B2 | 3/2009 | Tellenbach et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |

(56) References Cited

U.S. PATENT DOCUMENTS

| | | |
|---|---|---|
| 7,530,985 B2 | 5/2009 | Takemoto et al. |
| 7,533,790 B1 | 5/2009 | Knodel et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,544,197 B2 | 6/2009 | Kelsch et al. |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,572,285 B2 | 8/2009 | Frey et al. |
| 7,572,298 B2 | 8/2009 | Roller et al. |
| 7,575,144 B2 | 8/2009 | Ortiz et al. |
| 7,578,825 B2 | 8/2009 | Huebner |
| D600,712 S | 9/2009 | LaManna et al. |
| 7,582,086 B2 | 9/2009 | Privitera et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,605,826 B2 | 10/2009 | Sauer |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| 7,618,427 B2 | 11/2009 | Ortiz et al. |
| D605,201 S | 12/2009 | Lorenz et al. |
| D606,992 S | 12/2009 | Liu et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,625,388 B2 | 12/2009 | Boukhny et al. |
| 7,625,662 B2 | 12/2009 | Vaisnys et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,016 B2 | 1/2010 | Nycz et al. |
| 7,644,484 B2 | 1/2010 | Vereschagin |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,003 B2 | 2/2010 | Lorang et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,670,337 B2 | 3/2010 | Young |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,678,121 B1 | 3/2010 | Knodel |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,690,547 B2 | 4/2010 | Racenet et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |

(56) References Cited

U.S. PATENT DOCUMENTS

| | | | |
|---|---|---|---|
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |
| 7,706,853 B2 | 4/2010 | Hacker et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,708,768 B2 | 5/2010 | Danek et al. |
| 7,709,136 B2 | 5/2010 | Touchton et al. |
| 7,712,182 B2 | 5/2010 | Zeiler et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,735,704 B2 | 6/2010 | Bilotti |
| 7,736,254 B2 | 6/2010 | Schena |
| 7,736,306 B2 | 6/2010 | Brustad et al. |
| 7,736,356 B2 | 6/2010 | Cooper et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,758,613 B2 | 7/2010 | Whitman |
| 7,762,462 B2 | 7/2010 | Gelbman |
| 7,762,998 B2 | 7/2010 | Birk et al. |
| D622,286 S | 8/2010 | Umezawa |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,614 B1 | 8/2010 | McGonagle et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,651 B2 | 8/2010 | Madhani et al. |
| 7,780,663 B2 | 8/2010 | Yates et al. |
| 7,780,685 B2 | 8/2010 | Hunt et al. |
| 7,782,382 B2 | 8/2010 | Fujimura |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,819,894 B2 | 10/2010 | Mitsuishi et al. |
| 7,823,076 B2 | 10/2010 | Borovsky et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,829,416 B2 | 11/2010 | Kudou et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |

(56) References Cited

U.S. PATENT DOCUMENTS

| | | |
|---|---|---|
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |
| 7,840,253 B2 | 11/2010 | Tremblay et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,845,538 B2 | 12/2010 | Whitman |
| 7,845,912 B2 | 12/2010 | Sung et al. |
| 7,846,085 B2 | 12/2010 | Silverman et al. |
| 7,846,149 B2 | 12/2010 | Jankowski |
| 7,846,161 B2 | 12/2010 | Dumbauld et al. |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,877,869 B2 | 2/2011 | Mehdizadeh et al. |
| 7,879,063 B2 | 2/2011 | Khosravi |
| 7,879,070 B2 | 2/2011 | Ortiz et al. |
| 7,879,367 B2 | 2/2011 | Heublein et al. |
| 7,883,461 B2 | 2/2011 | Albrecht et al. |
| 7,883,465 B2 | 2/2011 | Donofrio et al. |
| 7,883,540 B2 | 2/2011 | Niwa et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,887,755 B2 | 2/2011 | Mingerink et al. |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,671 B2 | 3/2011 | Kim et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |
| 7,942,300 B2 | 5/2011 | Rethy et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,948,381 B2 | 5/2011 | Lindsay et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,951,166 B2 | 5/2011 | Orban, III et al. |
| 7,952,464 B2 | 5/2011 | Nikitin et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,954,688 B2 | 6/2011 | Argentine et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |

(56) References Cited

U.S. PATENT DOCUMENTS

| | | |
|---|---|---|
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,508 B2 | 7/2011 | Hoag |
| 7,976,563 B2 | 7/2011 | Summerer |
| 7,979,137 B2 | 7/2011 | Tracey et al. |
| 7,980,443 B2 | 7/2011 | Scheib et al. |
| 7,981,025 B2 | 7/2011 | Pool et al. |
| 7,981,102 B2 | 7/2011 | Patel et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,741 B2 | 9/2011 | Cole et al. |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,835 B2 | 10/2011 | Yasuda et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,052,697 B2 | 11/2011 | Phillips |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |

(56) References Cited

U.S. PATENT DOCUMENTS

| | | |
|---|---|---|
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,114,345 B2 | 2/2012 | Dlugos, Jr. et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,157,834 B2 | 4/2012 | Conlon |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,190,238 B2 | 5/2012 | Moll et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,207,863 B2 | 6/2012 | Neubauer et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,230,235 B2 | 7/2012 | Goodman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,235,274 B2 | 8/2012 | Cappola |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |

(56) References Cited

U.S. PATENT DOCUMENTS

| | | |
|---|---|---|
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,266,232 B2 | 9/2012 | Piper et al. |
| 8,267,300 B2 | 9/2012 | Boudreaux |
| 8,267,849 B2 | 9/2012 | Wazer et al. |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,290,883 B2 | 10/2012 | Takeuchi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| D672,784 S | 12/2012 | Clanton et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,271 B2 | 12/2012 | Humayun et al. |
| 8,323,789 B2 | 12/2012 | Rozhin et al. |
| 8,324,585 B2 | 12/2012 | McBroom et al. |
| 8,327,514 B2 | 12/2012 | Kim |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,065 B2 | 12/2012 | Shah |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,948 B2 | 1/2013 | Bahney |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,368,327 B2 | 2/2013 | Benning et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,374,723 B2 | 2/2013 | Zhao et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,377,059 B2 | 2/2013 | Deville et al. |
| 8,381,828 B2 | 2/2013 | Whitman et al. |
| 8,381,834 B2 | 2/2013 | Barhitte et al. |
| 8,382,773 B2 | 2/2013 | Whitfield et al. |

(56) References Cited

U.S. PATENT DOCUMENTS

| | | |
|---|---|---|
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,972 B2 | 3/2013 | Kostrzewski |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |
| 8,400,108 B2 | 3/2013 | Powell et al. |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |
| 8,403,198 B2 | 3/2013 | Sorrentino et al. |
| 8,403,832 B2 | 3/2013 | Cunningham et al. |
| 8,403,926 B2 | 3/2013 | Nobis et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| D680,646 S | 4/2013 | Hunt et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,211 B2 | 4/2013 | Baroud |
| 8,409,222 B2 | 4/2013 | Whitfield et al. |
| 8,409,223 B2 | 4/2013 | Sorrentino et al. |
| 8,409,234 B2 | 4/2013 | Stahler et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,469 B2 | 4/2013 | Diolaiti |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,419,755 B2 | 4/2013 | Deem et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,424,742 B2 | 4/2013 | Bettuchi |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,439,830 B2 | 5/2013 | McKinley et al. |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| D686,244 S | 7/2013 | Moriya et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,486,047 B2 | 7/2013 | Stopek |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,852 B2 | 7/2013 | Viola |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,491,624 B2 | 7/2013 | Kerr et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,673 B2 | 8/2013 | Keller |
| 8,499,966 B2 | 8/2013 | Palmer et al. |
| 8,499,992 B2 | 8/2013 | Whitman et al. |
| 8,499,993 B2 | 8/2013 | Shelton, IV et al. |
| 8,499,994 B2 | 8/2013 | D'Arcangelo |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,505,802 B2 | 8/2013 | Viola et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,938 B2 | 8/2013 | Eisenhardt et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |

(56) References Cited

U.S. PATENT DOCUMENTS

| | | |
|---|---|---|
| 8,523,787 B2 | 9/2013 | Ludwin et al. |
| 8,523,881 B2 | 9/2013 | Cabiri et al. |
| 8,523,882 B2 | 9/2013 | Huitema et al. |
| 8,523,900 B2 | 9/2013 | Jinno et al. |
| 8,529,588 B2 | 9/2013 | Ahlberg et al. |
| 8,529,599 B2 | 9/2013 | Holsten |
| 8,529,600 B2 | 9/2013 | Woodard, Jr. et al. |
| 8,529,819 B2 | 9/2013 | Ostapoff et al. |
| 8,531,153 B2 | 9/2013 | Baarman et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,646 B2 | 9/2013 | Mendez-Coll |
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,598 B2 | 11/2013 | Razzaque et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,591,400 B2 | 11/2013 | Sugiyama |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,431 B2 | 12/2013 | Timm et al. |
| 8,617,155 B2 | 12/2013 | Johnson et al. |
| 8,620,473 B2 | 12/2013 | Diolaiti et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,467 B2 | 1/2014 | Whitman et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,656,929 B2 | 2/2014 | Miller et al. |
| 8,657,174 B2 | 2/2014 | Yates et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,209 B2 | 3/2014 | Crainich |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Baic et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,114 B2 | 3/2014 | Chapman et al. |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |

(56) References Cited

U.S. PATENT DOCUMENTS

| | | |
|---|---|---|
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,706,316 B1 | 4/2014 | Hoevenaar |
| 8,708,210 B2 | 4/2014 | Zemlok et al. |
| 8,708,211 B2 | 4/2014 | Zemlok et al. |
| 8,708,212 B2 | 4/2014 | Williams |
| 8,708,213 B2 | 4/2014 | Shelton, IV et al. |
| 8,709,012 B2 | 4/2014 | Muller |
| 8,712,549 B2 | 4/2014 | Zdeblick et al. |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,611 B2 | 5/2014 | Milliman |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak et al. |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,765,942 B2 | 7/2014 | Feraud et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,098 B2 | 8/2014 | Long |
| 8,794,496 B2 | 8/2014 | Scirica |
| 8,794,497 B2 | 8/2014 | Zingman |
| 8,795,159 B2 | 8/2014 | Moriyama |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,828,046 B2 | 9/2014 | Stefanchik et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,004 B2 | 9/2014 | Holsten et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |

(56) References Cited

U.S. PATENT DOCUMENTS

| | | |
|---|---|---|
| 8,845,622 B2 | 9/2014 | Paik et al. |
| 8,851,215 B2 | 10/2014 | Goto |
| 8,851,354 B2 | 10/2014 | Swensgard et al. |
| 8,851,355 B2 | 10/2014 | Aranyi et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,855,822 B2 | 10/2014 | Bartol et al. |
| 8,857,692 B2 | 10/2014 | Shima et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,547 B2 | 10/2014 | Brogna |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,869,912 B2 | 10/2014 | Roßkamp et al. |
| 8,869,913 B2 | 10/2014 | Matthias et al. |
| 8,870,049 B2 | 10/2014 | Amid et al. |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,871,829 B2 | 10/2014 | Gerold et al. |
| 8,875,971 B2 | 11/2014 | Hall et al. |
| 8,875,972 B2 | 11/2014 | Weisenburgh, II et al. |
| 8,876,698 B2 | 11/2014 | Sakamoto et al. |
| 8,876,857 B2 | 11/2014 | Burbank |
| 8,876,858 B2 | 11/2014 | Braun |
| 8,882,660 B2 | 11/2014 | Phee et al. |
| 8,882,792 B2 | 11/2014 | Dietz et al. |
| 8,884,560 B2 | 11/2014 | Ito |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,910,847 B2 | 12/2014 | Nalagatla et al. |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,915,842 B2 | 12/2014 | Weisenburgh, II et al. |
| 8,920,368 B2 | 12/2014 | Sandhu et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,931,692 B2 | 1/2015 | Sancak |
| 8,936,614 B2 | 1/2015 | Allen, IV |
| 8,937,408 B2 | 1/2015 | Ganem et al. |
| 8,939,343 B2 | 1/2015 | Milliman et al. |
| 8,939,344 B2 | 1/2015 | Olson et al. |
| 8,939,898 B2 | 1/2015 | Omoto |
| 8,944,069 B2 | 2/2015 | Miller et al. |
| 8,945,095 B2 | 2/2015 | Blumenkranz et al. |
| 8,945,098 B2 | 2/2015 | Seibold et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,961,542 B2 | 2/2015 | Whitfield et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,984,711 B2 | 3/2015 | Ota et al. |
| 8,985,240 B2 | 3/2015 | Winnard |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,004,799 B1 | 4/2015 | Tibbits |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |

(56) References Cited

U.S. PATENT DOCUMENTS

| | | | |
|---|---|---|---|
| 9,014,856 B2 | 4/2015 | Manzo et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,017,849 B2 | 4/2015 | Stulen et al. |
| 9,017,851 B2 | 4/2015 | Felder et al. |
| D729,274 S | 5/2015 | Clement et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,468 B2 | 5/2015 | Scarfogliero et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,028,529 B2 | 5/2015 | Fox et al. |
| 9,030,166 B2 | 5/2015 | Kano |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |
| 9,039,694 B2 | 5/2015 | Ross et al. |
| 9,039,720 B2 | 5/2015 | Madan |
| 9,039,736 B2 | 5/2015 | Scirica et al. |
| 9,040,062 B2 | 5/2015 | Maeda et al. |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,238 B2 | 6/2015 | Orszulak |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,089 B2 | 6/2015 | Orszulak |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,070,068 B2 | 6/2015 | Coveley et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,586 B2 | 7/2015 | Hafner et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,338 B2 | 7/2015 | Smith et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,095,642 B2 | 8/2015 | Harder et al. |
| 9,096,033 B2 | 8/2015 | Holop et al. |
| 9,098,153 B2 | 8/2015 | Shen et al. |
| 9,099,863 B2 | 8/2015 | Smith et al. |
| 9,099,877 B2 | 8/2015 | Banos et al. |
| 9,099,922 B2 | 8/2015 | Toosky et al. |
| 9,101,358 B2 | 8/2015 | Kerr et al. |
| 9,101,359 B2 | 8/2015 | Smith et al. |
| 9,101,385 B2 | 8/2015 | Shelton, IV et al. |
| 9,101,475 B2 | 8/2015 | Wei et al. |
| 9,101,621 B2 | 8/2015 | Zeldis |
| 9,107,663 B2 | 8/2015 | Swensgard |
| 9,107,667 B2 | 8/2015 | Hodgkinson |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,866 B2 | 8/2015 | Felder et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,875 B2 | 8/2015 | Viola et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,651 B2 | 9/2015 | Mandakolathur Vasudevan et al. |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D740,414 S | 10/2015 | Katsura |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,154,189 B2 | 10/2015 | Von Novak et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,161,855 B2 | 10/2015 | Rousseau et al. |
| 9,164,271 B2 | 10/2015 | Ebata et al. |
| 9,167,960 B2 | 10/2015 | Yamaguchi et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,171,244 B2 | 10/2015 | Endou et al. |
| 9,179,832 B2 | 11/2015 | Diolaiti |

(56) References Cited

U.S. PATENT DOCUMENTS

| | | |
|---|---|---|
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,376 B2 | 11/2015 | Almodovar |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| D746,459 S | 12/2015 | Kaercher et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,881 B2 | 12/2015 | Penna |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,504 B2 | 12/2015 | Viola et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,686 B2 | 1/2016 | Blair |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,760 B2 | 1/2016 | Shelton, IV |
| 9,226,761 B2 | 1/2016 | Burbank |
| 9,226,767 B2 | 1/2016 | Stulen et al. |
| 9,226,799 B2 | 1/2016 | Lightcap et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,241,758 B2 | 1/2016 | Franer et al. |
| 9,244,524 B2 | 1/2016 | Inoue et al. |
| D748,668 S | 2/2016 | Kim et al. |
| D749,128 S | 2/2016 | Perez et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,254,170 B2 | 2/2016 | Parihar et al. |
| 9,259,265 B2 | 2/2016 | Harris et al. |
| 9,259,268 B2 | 2/2016 | Behnke, II et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,510 B2 | 2/2016 | Dietzel et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,283,334 B2 | 3/2016 | Mantell et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,811 B2 | 4/2016 | Goldberg et al. |
| 9,307,965 B2 | 4/2016 | Ming et al. |
| 9,307,986 B2 | 4/2016 | Hall et al. |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,291 B2 | 4/2016 | Schall et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |

(56) References Cited

U.S. PATENT DOCUMENTS

| | | |
|---|---|---|
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,326,824 B2 | 5/2016 | Inoue et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,339,342 B2 | 5/2016 | Prisco et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,352,071 B2 | 5/2016 | Landgrebe et al. |
| D758,433 S | 6/2016 | Lee et al. |
| D759,063 S | 6/2016 | Chen |
| 9,358,003 B2 | 6/2016 | Hall et al. |
| 9,358,004 B2 | 6/2016 | Sniffin et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |
| 9,358,065 B2 | 6/2016 | Ladtkow et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,223 B2 | 6/2016 | Scirica |
| 9,364,226 B2 | 6/2016 | Zemlok et al. |
| 9,364,228 B2 | 6/2016 | Straehnz et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,361 B2 | 6/2016 | Viola et al. |
| 9,370,362 B2 | 6/2016 | Petty et al. |
| 9,370,364 B2 | 6/2016 | Smith et al. |
| 9,370,400 B2 | 6/2016 | Parihar |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,385,640 B2 | 7/2016 | Sun et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,392,885 B2 | 7/2016 | Vogler et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,393,354 B2 | 7/2016 | Freedman et al. |
| 9,396,369 B1 | 7/2016 | Whitehurst et al. |
| 9,396,669 B2 | 7/2016 | Karkanias et al. |
| 9,398,905 B2 | 7/2016 | Martin |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,402,682 B2 | 8/2016 | Worrell et al. |
| 9,402,688 B2 | 8/2016 | Min et al. |
| 9,408,604 B2 | 8/2016 | Shelton, IV et al. |
| 9,408,605 B1 | 8/2016 | Knodel et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,421,682 B2 | 8/2016 | McClaskey et al. |
| 9,427,223 B2 | 8/2016 | Park et al. |
| 9,427,231 B2 | 8/2016 | Racenet et al. |
| 9,429,204 B2 | 8/2016 | Stefan et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Overes et al. |
| 9,451,958 B2 | 9/2016 | Shelton, IV et al. |
| 9,452,020 B2 | 9/2016 | Griffiths et al. |
| D768,152 S | 10/2016 | Gutierrez et al. |
| D768,156 S | 10/2016 | Frincke |
| D768,167 S | 10/2016 | Jones et al. |
| D769,315 S | 10/2016 | Scotti |
| D769,930 S | 10/2016 | Agrawal |
| 9,461,340 B2 | 10/2016 | Li et al. |
| 9,463,012 B2 | 10/2016 | Bonutti et al. |
| 9,463,040 B2 | 10/2016 | Jeong et al. |
| 9,463,260 B2 | 10/2016 | Stopek |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,513 B2 | 10/2016 | Ishida et al. |
| 9,474,523 B2 | 10/2016 | Meade et al. |
| 9,474,528 B2 | 10/2016 | Marczyk |
| 9,474,540 B2 | 10/2016 | Stokes et al. |
| 9,475,180 B2 | 10/2016 | Eshleman et al. |
| 9,477,649 B1 | 10/2016 | Davidson et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |

(56) References Cited

U.S. PATENT DOCUMENTS

| | | |
|---|---|---|
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,215 B2 | 11/2016 | Olson et al. |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,172 B2 | 11/2016 | Weisshaupt et al. |
| 9,492,189 B2 | 11/2016 | Williams et al. |
| 9,492,192 B2 | 11/2016 | To et al. |
| 9,492,237 B2 | 11/2016 | Kang et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,520 B2 | 11/2016 | Worrell et al. |
| 9,504,521 B2 | 11/2016 | Deutmeyer et al. |
| 9,504,528 B2 | 11/2016 | Ivinson et al. |
| 9,507,399 B2 | 11/2016 | Chien |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,515,366 B2 | 12/2016 | Herbsommer et al. |
| 9,517,063 B2 | 12/2016 | Swayze et al. |
| 9,517,065 B2 | 12/2016 | Simms et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,005 B2 | 12/2016 | Williams et al. |
| 9,522,014 B2 | 12/2016 | Nishizawa et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |
| 9,526,921 B2 | 12/2016 | Kimball et al. |
| D776,683 S | 1/2017 | Gobinski et al. |
| D777,773 S | 1/2017 | Shi |
| 9,532,783 B2 | 1/2017 | Swayze et al. |
| 9,539,060 B2 | 1/2017 | Lightcap et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,733 B2 | 1/2017 | Knodel |
| 9,549,735 B2 | 1/2017 | Shelton, IV et al. |
| 9,549,750 B2 | 1/2017 | Shelton, IV et al. |
| 9,554,794 B2 | 1/2017 | Baber et al. |
| 9,554,796 B2 | 1/2017 | Kostrzewski |
| 9,554,803 B2 | 1/2017 | Smith et al. |
| 9,554,812 B2 | 1/2017 | Inkpen et al. |
| 9,554,854 B2 | 1/2017 | Yates et al. |
| 9,559,624 B2 | 1/2017 | Philipp |
| 9,561,013 B2 | 2/2017 | Tsuchiya |
| 9,561,029 B2 | 2/2017 | Scheib et al. |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,561,072 B2 | 2/2017 | Ko |
| 9,561,082 B2 | 2/2017 | Yen et al. |
| 9,566,061 B2 | 2/2017 | Aronhalt et al. |
| 9,566,062 B2 | 2/2017 | Boudreaux |
| 9,566,064 B2 | 2/2017 | Williams et al. |
| 9,566,065 B2 | 2/2017 | Knodel |
| 9,566,067 B2 | 2/2017 | Milliman et al. |
| 9,572,552 B1 | 2/2017 | Bodor et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| 9,579,143 B2 | 2/2017 | Ullrich et al. |
| 9,579,158 B2 | 2/2017 | Brianza et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,078 B2 | 3/2017 | Scirica et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,079 B2 | 4/2017 | Kamei et al. |
| 9,610,080 B2 | 4/2017 | Whitfield et al. |
| 9,610,412 B2 | 4/2017 | Zemlok et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,622,746 B2 | 4/2017 | Simms et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,632 B2 | 4/2017 | Linder et al. |
| 9,629,652 B2 | 4/2017 | Mumaw et al. |
| 9,629,814 B2 | 4/2017 | Widenhouse et al. |
| D785,794 S | 5/2017 | Magno, Jr. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,091 B2 | 5/2017 | Beardsley et al. |
| 9,636,111 B2 | 5/2017 | Wenchell |
| 9,636,112 B2 | 5/2017 | Penna et al. |
| 9,636,113 B2 | 5/2017 | Wenchell |
| 9,636,850 B2 | 5/2017 | Stopek (nee Prommersberger) et al. |
| 9,641,122 B2 | 5/2017 | Romanowich et al. |
| 9,642,620 B2 | 5/2017 | Baxter, III et al. |
| 9,642,642 B2 | 5/2017 | Lim |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,649,190 B2 | 5/2017 | Mathies |
| 9,651,032 B2 | 5/2017 | Weaver et al. |
| 9,655,613 B2 | 5/2017 | Schaller |
| 9,655,614 B2 | 5/2017 | Swensgard et al. |
| 9,655,615 B2 | 5/2017 | Knodel et al. |

(56) References Cited

U.S. PATENT DOCUMENTS

| | | |
|---|---|---|
| 9,655,616 B2 | 5/2017 | Aranyi |
| 9,655,624 B2 | 5/2017 | Shelton, IV et al. |
| 9,661,991 B2 | 5/2017 | Glossop |
| 9,662,108 B2 | 5/2017 | Williams |
| 9,662,110 B2 | 5/2017 | Huang et al. |
| 9,662,111 B2 | 5/2017 | Holsten et al. |
| 9,662,116 B2 | 5/2017 | Smith et al. |
| 9,662,130 B2 | 5/2017 | Bartels et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,668,735 B2 | 6/2017 | Beetel |
| 9,675,344 B2 | 6/2017 | Combrowski et al. |
| 9,675,348 B2 | 6/2017 | Smith et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,368 B2 | 6/2017 | Guo et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,775 B2 | 7/2017 | Agarwal et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,315 B2 | 7/2017 | Chen et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |
| 9,700,321 B2 | 7/2017 | Shelton, IV et al. |
| 9,700,334 B2 | 7/2017 | Hinman et al. |
| 9,700,381 B2 | 7/2017 | Amat Girbau |
| 9,702,823 B2 | 7/2017 | Maher et al. |
| 9,706,674 B2 | 7/2017 | Collins et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,003 B2 | 7/2017 | Hoell, Jr. et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,466 B2 | 7/2017 | Kostrzewski |
| 9,713,468 B2 | 7/2017 | Harris et al. |
| 9,713,470 B2 | 7/2017 | Scirica et al. |
| 9,713,474 B2 | 7/2017 | Lorenz |
| D795,919 S | 8/2017 | Bischoff et al. |
| 9,717,497 B2 | 8/2017 | Zerkle et al. |
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,730,757 B2 | 8/2017 | Brudniok |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,298 B2 | 8/2017 | Isbell, Jr. |
| 9,737,299 B2 | 8/2017 | Yan |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,323 B2 | 8/2017 | Thapliyal et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,503 B2 | 9/2017 | Milliman |
| 9,750,639 B2 | 9/2017 | Barnes et al. |
| 9,751,176 B2 | 9/2017 | McRoberts et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,187 B2 | 10/2017 | Zergiebel et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |

(56) References Cited

U.S. PATENT DOCUMENTS

| | | |
|---|---|---|
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,815,118 B1 | 11/2017 | Schmitt et al. |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,235 B2 | 12/2017 | Penna et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,839,481 B2 | 12/2017 | Blumenkranz et al. |
| 9,844,313 B2 | 12/2017 | DiCarlo et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,850,499 B2 | 12/2017 | Baylink et al. |
| 9,850,994 B2 | 12/2017 | Schena |
| D808,989 S | 1/2018 | Ayvazian et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,366 B2 | 1/2018 | Aranyi |
| 9,861,382 B2 | 1/2018 | Smith et al. |
| 9,861,446 B2 | 1/2018 | Lang |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,867,617 B2 | 1/2018 | Ma |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,722 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,358 B2 | 2/2018 | Faller et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,117 B2 | 4/2018 | Hathaway et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |

(56) References Cited

U.S. PATENT DOCUMENTS

| | | |
|---|---|---|
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,740 B2 | 5/2018 | Krause et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| 10,004,552 B1 | 6/2018 | Kleyman et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,120 B2 | 7/2018 | Martin et al. |
| 10,022,123 B2 | 7/2018 | Williams et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,046,904 B2 | 8/2018 | Evans et al. |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,642 B2 | 9/2018 | Marczyk et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,126 B2 | 10/2018 | Sauer |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,123,845 B2 | 11/2018 | Yeung |

(56) References Cited

U.S. PATENT DOCUMENTS

| | | |
|---|---|---|
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,382 B2 | 11/2018 | Gladstone |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| 10,136,949 B2 | 11/2018 | Felder et al. |
| D835,659 S | 12/2018 | Anzures et al. |
| D836,124 S | 12/2018 | Fan |
| 10,143,474 B2 | 12/2018 | Bucciaglia et al. |
| 10,146,423 B1 | 12/2018 | Reed et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,161,816 B2 | 12/2018 | Jackson et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,389 B2 | 1/2019 | Vendely et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,911 B2 | 2/2019 | Miller et al. |
| 10,194,912 B2 | 2/2019 | Scheib et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| D847,199 S | 4/2019 | Whitmore |
| 10,244,991 B2 | 4/2019 | Shademan et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,645 B2 | 4/2019 | Kostrzewski |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,363 B2 | 4/2019 | Worrell et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,840 B2 | 4/2019 | Sapre |
| 10,271,844 B2 | 4/2019 | Valentine et al. |
| 10,271,845 B2 | 4/2019 | Shelton, IV |

(56) References Cited

U.S. PATENT DOCUMENTS

| | | |
|---|---|---|
| 10,271,846 B2 | 4/2019 | Shelton, IV et al. |
| 10,271,847 B2 | 4/2019 | Racenet et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,700 B2 | 5/2019 | Scheib |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |
| 10,299,790 B2 | 5/2019 | Beardsley |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| 10,303,851 B2 | 5/2019 | Nguyen et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,578 B2 | 6/2019 | Leimbach et al. |
| 10,314,579 B2 | 6/2019 | Chowaniec et al. |
| 10,314,580 B2 | 6/2019 | Scheib et al. |
| 10,314,582 B2 | 6/2019 | Shelton, IV et al. |
| 10,314,584 B2 | 6/2019 | Scirica et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,937 B2 | 7/2019 | Williams |
| 10,349,939 B2 | 7/2019 | Shelton, IV et al. |
| 10,349,941 B2 | 7/2019 | Marczyk et al. |
| 10,349,963 B2 | 7/2019 | Fiksen et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,866 B2 | 8/2019 | Wang et al. |
| 10,368,867 B2 | 8/2019 | Harris et al. |
| 10,368,892 B2 | 8/2019 | Stulen et al. |
| 10,374,544 B2 | 8/2019 | Yokoyama et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,631 B2 | 8/2019 | Collings et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D859,466 S | 9/2019 | Okada et al. |
| D860,219 S | 9/2019 | Rasmussen et al. |
| D861,035 S | 9/2019 | Park et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,398,460 B2 | 9/2019 | Overmyer |
| 10,404,136 B2 | 9/2019 | Oktavec et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,405,937 B2 | 9/2019 | Black et al. |
| 10,413,155 B2 | 9/2019 | Inoue |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,551 B2 | 9/2019 | Calderoni |
| 10,420,552 B2 | 9/2019 | Shelton, IV et al. |
| 10,420,553 B2 | 9/2019 | Shelton, IV et al. |
| 10,420,554 B2 | 9/2019 | Collings et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |
| 10,420,561 B2 | 9/2019 | Shelton, IV et al. |

(56) References Cited

U.S. PATENT DOCUMENTS

| | | |
|---|---|---|
| 10,420,577 B2 | 9/2019 | Chowaniec et al. |
| D861,707 S | 10/2019 | Yang |
| D862,518 S | 10/2019 | Niven et al. |
| D863,343 S | 10/2019 | Mazlish et al. |
| D864,388 S | 10/2019 | Barber |
| D865,174 S | 10/2019 | Auld et al. |
| D865,175 S | 10/2019 | Widenhouse et al. |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,426,555 B2 | 10/2019 | Crowley et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,842 B2 | 10/2019 | Amariglio et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,371 B2 | 11/2019 | Kostrzewski |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,767 B2 | 11/2019 | Gleiman et al. |
| 10,470,768 B2 | 11/2019 | Harris et al. |
| 10,470,769 B2 | 11/2019 | Shelton, IV et al. |
| 10,471,282 B2 | 11/2019 | Kirk et al. |
| 10,471,576 B2 | 11/2019 | Totsu |
| 10,471,607 B2 | 11/2019 | Butt et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,187 B2 | 11/2019 | Shelton, IV et al. |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,482,292 B2 | 11/2019 | Clouser et al. |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,917 B2 | 12/2019 | Scheib et al. |
| 10,499,918 B2 | 12/2019 | Schellin et al. |
| 10,500,000 B2 | 12/2019 | Swayze et al. |
| 10,500,004 B2 | 12/2019 | Hanuschik et al. |
| 10,500,309 B2 | 12/2019 | Shah et al. |
| 10,507,034 B2 | 12/2019 | Timm |
| 10,508,720 B2 | 12/2019 | Nicholas |
| 10,512,461 B2 | 12/2019 | Gupta et al. |
| 10,512,462 B2 | 12/2019 | Felder et al. |
| 10,512,464 B2 | 12/2019 | Park et al. |
| 10,517,590 B2 | 12/2019 | Giordano et al. |
| 10,517,592 B2 | 12/2019 | Shelton, IV et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 10,524,784 B2 | 1/2020 | Kostrzewski |
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,524,870 B2 | 1/2020 | Saraliev et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,908 B2 | 1/2020 | Mei et al. |
| 10,542,974 B2 | 1/2020 | Yates et al. |
| 10,542,976 B2 | 1/2020 | Calderoni et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,593 B2 | 2/2020 | Shelton, IV et al. |
| 10,548,600 B2 | 2/2020 | Shelton, IV et al. |
| 10,548,673 B2 | 2/2020 | Harris et al. |
| 10,561,412 B2 | 2/2020 | Bookbinder et al. |
| 10,561,418 B2 | 2/2020 | Richard et al. |
| 10,561,419 B2 | 2/2020 | Beardsley |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,493 B2 | 2/2020 | Blase et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| D879,808 S | 3/2020 | Harris et al. |
| D879,809 S | 3/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |
| 10,588,231 B2 | 3/2020 | Sgroi, Jr. et al. |

(56) References Cited

U.S. PATENT DOCUMENTS

| | | |
|---|---|---|
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,589,410 B2 | 3/2020 | Aho |
| 10,595,835 B2 | 3/2020 | Kerr et al. |
| 10,595,862 B2 | 3/2020 | Shelton, IV et al. |
| 10,595,882 B2 | 3/2020 | Parfett et al. |
| 10,595,887 B2 | 3/2020 | Shelton, IV et al. |
| 10,595,929 B2 | 3/2020 | Boudreaux et al. |
| 10,603,036 B2 | 3/2020 | Hunter et al. |
| 10,603,039 B2 | 3/2020 | Vendely et al. |
| 10,603,041 B2 | 3/2020 | Miller et al. |
| 10,603,117 B2 | 3/2020 | Schings et al. |
| 10,603,128 B2 | 3/2020 | Zergiebel et al. |
| D882,783 S | 4/2020 | Shelton, IV et al. |
| 10,610,224 B2 | 4/2020 | Shelton, IV et al. |
| 10,610,225 B2 | 4/2020 | Reed et al. |
| 10,610,236 B2 | 4/2020 | Baril |
| 10,610,313 B2 | 4/2020 | Bailey et al. |
| 10,610,346 B2 | 4/2020 | Schwartz |
| 10,614,184 B2 | 4/2020 | Solki |
| 10,617,411 B2 | 4/2020 | Williams |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,416 B2 | 4/2020 | Leimbach et al. |
| 10,617,417 B2 | 4/2020 | Baxter, III et al. |
| 10,617,418 B2 | 4/2020 | Barton et al. |
| 10,617,420 B2 | 4/2020 | Shelton, IV et al. |
| 10,617,438 B2 | 4/2020 | O'Keefe et al. |
| 10,624,616 B2 | 4/2020 | Mukherjee et al. |
| 10,624,630 B2 | 4/2020 | Deville et al. |
| 10,624,633 B2 | 4/2020 | Shelton, IV et al. |
| 10,624,634 B2 | 4/2020 | Shelton, IV et al. |
| 10,624,635 B2 | 4/2020 | Harris et al. |
| 10,624,709 B2 | 4/2020 | Remm |
| 10,624,861 B2 | 4/2020 | Widenhouse et al. |
| 10,625,062 B2 | 4/2020 | Matlock et al. |
| 10,631,857 B2 | 4/2020 | Kostrzewski |
| 10,631,858 B2 | 4/2020 | Burbank |
| 10,631,859 B2 | 4/2020 | Shelton, IV et al. |
| 10,631,860 B2 | 4/2020 | Bakos et al. |
| 10,636,104 B2 | 4/2020 | Mazar et al. |
| 10,639,018 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,089 B2 | 5/2020 | Manwaring et al. |
| 10,639,115 B2 | 5/2020 | Shelton, IV et al. |
| 10,642,633 B1 | 5/2020 | Chopra et al. |
| 10,645,905 B2 | 5/2020 | Gandola et al. |
| 10,646,220 B2 | 5/2020 | Shelton, IV et al. |
| 10,646,292 B2 | 5/2020 | Solomon et al. |
| 10,653,413 B2 | 5/2020 | Worthington et al. |
| 10,653,417 B2 | 5/2020 | Shelton, IV et al. |
| 10,653,435 B2 | 5/2020 | Shelton, IV et al. |
| 10,660,640 B2 | 5/2020 | Yates et al. |
| 10,667,408 B2 | 5/2020 | Sgroi, Jr. et al. |
| D888,953 S | 6/2020 | Baxter, III et al. |
| 10,667,808 B2 | 6/2020 | Baxter, III et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,818 B2 | 6/2020 | McLain et al. |
| 10,674,895 B2 | 6/2020 | Yeung et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,028 B2 | 6/2020 | Shelton, IV et al. |
| 10,675,035 B2 | 6/2020 | Zingman |
| 10,675,080 B2 | 6/2020 | Woloszko et al. |
| 10,675,102 B2 | 6/2020 | Forgione et al. |
| 10,677,035 B2 | 6/2020 | Balan et al. |
| 10,682,134 B2 | 6/2020 | Shelton, IV et al. |
| 10,682,136 B2 | 6/2020 | Harris et al. |
| 10,682,137 B2 | 6/2020 | Stokes et al. |
| 10,682,138 B2 | 6/2020 | Shelton, IV et al. |
| 10,682,141 B2 | 6/2020 | Moore et al. |
| 10,682,142 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,812 B2 | 6/2020 | Shelton, IV et al. |
| 10,687,813 B2 | 6/2020 | Shelton, IV et al. |
| 10,687,817 B2 | 6/2020 | Shelton, IV et al. |
| 10,687,819 B2 | 6/2020 | Stokes et al. |
| 10,687,904 B2 | 6/2020 | Harris et al. |
| 10,695,053 B2 | 6/2020 | Hess et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,062 B2 | 6/2020 | Leimbach et al. |
| 10,695,063 B2 | 6/2020 | Morgan et al. |
| 10,695,074 B2 | 6/2020 | Carusillo |
| 10,695,081 B2 | 6/2020 | Shelton, IV et al. |
| 10,695,119 B2 | 6/2020 | Smith |
| 10,695,123 B2 | 6/2020 | Allen, IV |
| 10,695,187 B2 | 6/2020 | Moskowitz et al. |
| D890,784 S | 7/2020 | Shelton, IV et al. |
| 10,702,266 B2 | 7/2020 | Parihar et al. |
| 10,702,267 B2 | 7/2020 | Hess et al. |
| 10,702,270 B2 | 7/2020 | Shelton, IV et al. |
| 10,702,271 B2 | 7/2020 | Aranyi et al. |
| 10,705,660 B2 | 7/2020 | Xiao |
| 10,709,446 B2 | 7/2020 | Harris et al. |
| 10,709,468 B2 | 7/2020 | Shelton, IV et al. |
| 10,709,469 B2 | 7/2020 | Shelton, IV et al. |
| 10,709,495 B2 | 7/2020 | Broderick et al. |
| 10,709,496 B2 | 7/2020 | Moua et al. |
| 10,716,563 B2 | 7/2020 | Shelton, IV et al. |
| 10,716,565 B2 | 7/2020 | Shelton, IV et al. |
| 10,716,568 B2 | 7/2020 | Hall et al. |
| 10,716,614 B2 | 7/2020 | Yates et al. |
| 10,717,179 B2 | 7/2020 | Koenig et al. |
| 10,722,232 B2 | 7/2020 | Yates et al. |
| 10,722,233 B2 | 7/2020 | Wellman |
| 10,722,292 B2 | 7/2020 | Arya et al. |
| 10,722,293 B2 | 7/2020 | Arya et al. |
| 10,722,317 B2 | 7/2020 | Ward et al. |
| D893,717 S | 8/2020 | Messerly et al. |
| 10,729,432 B2 | 8/2020 | Shelton, IV et al. |
| 10,729,434 B2 | 8/2020 | Harris et al. |
| 10,729,435 B2 | 8/2020 | Richard |
| 10,729,436 B2 | 8/2020 | Shelton, IV et al. |
| 10,729,443 B2 | 8/2020 | Cabrera et al. |
| 10,729,458 B2 | 8/2020 | Stoddard et al. |
| 10,729,501 B2 | 8/2020 | Leimbach et al. |
| 10,729,509 B2 | 8/2020 | Shelton, IV et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,630 B2 | 8/2020 | Huang et al. |
| 10,736,633 B2 | 8/2020 | Vendely et al. |
| 10,736,634 B2 | 8/2020 | Shelton, IV et al. |
| 10,736,636 B2 | 8/2020 | Baxter, III et al. |
| 10,736,644 B2 | 8/2020 | Windolf et al. |
| 10,736,702 B2 | 8/2020 | Harris et al. |
| 10,737,398 B2 | 8/2020 | Remirez et al. |
| 10,743,849 B2 | 8/2020 | Shelton, IV et al. |
| 10,743,850 B2 | 8/2020 | Hibner et al. |
| 10,743,851 B2 | 8/2020 | Swayze et al. |
| 10,743,868 B2 | 8/2020 | Shelton, IV et al. |
| 10,743,870 B2 | 8/2020 | Hall et al. |
| 10,743,872 B2 | 8/2020 | Leimbach et al. |
| 10,743,873 B2 | 8/2020 | Overmyer et al. |
| 10,743,874 B2 | 8/2020 | Shelton, IV et al. |
| 10,743,875 B2 | 8/2020 | Shelton, IV et al. |

(56) References Cited

U.S. PATENT DOCUMENTS

| | | |
|---|---|---|
| 10,743,877 B2 | 8/2020 | Shelton, IV et al. |
| 10,743,930 B2 | 8/2020 | Nagtegaal |
| 10,751,048 B2 | 8/2020 | Whitman et al. |
| 10,751,053 B2 | 8/2020 | Harris et al. |
| 10,751,076 B2 | 8/2020 | Laurent et al. |
| 10,751,138 B2 | 8/2020 | Giordano et al. |
| 10,758,226 B2 | 9/2020 | Weir et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,233 B2 | 9/2020 | Scheib et al. |
| 10,758,259 B2 | 9/2020 | Demmy et al. |
| 10,765,425 B2 | 9/2020 | Yates et al. |
| 10,765,427 B2 | 9/2020 | Shelton, IV et al. |
| 10,765,429 B2 | 9/2020 | Leimbach et al. |
| 10,765,430 B2 | 9/2020 | Wixey |
| 10,765,432 B2 | 9/2020 | Moore et al. |
| 10,765,442 B2 | 9/2020 | Strobl |
| 10,772,625 B2 | 9/2020 | Shelton, IV et al. |
| 10,772,628 B2 | 9/2020 | Chen et al. |
| 10,772,629 B2 | 9/2020 | Shelton, IV et al. |
| 10,772,630 B2 | 9/2020 | Wixey |
| 10,772,631 B2 | 9/2020 | Zergiebel et al. |
| 10,772,632 B2 | 9/2020 | Kostrzewski |
| 10,772,651 B2 | 9/2020 | Shelton, IV et al. |
| 10,779,818 B2 | 9/2020 | Zemlok et al. |
| 10,779,820 B2 | 9/2020 | Harris et al. |
| 10,779,821 B2 | 9/2020 | Harris et al. |
| 10,779,822 B2 | 9/2020 | Yates et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,826 B2 | 9/2020 | Shelton, IV et al. |
| 10,779,903 B2 | 9/2020 | Wise et al. |
| 10,780,539 B2 | 9/2020 | Shelton, IV et al. |
| 10,786,248 B2 | 9/2020 | Rousseau et al. |
| 10,786,253 B2 | 9/2020 | Shelton, IV et al. |
| 10,786,255 B2 | 9/2020 | Hodgkinson et al. |
| 10,792,038 B2 | 10/2020 | Becerra et al. |
| 10,796,471 B2 | 10/2020 | Leimbach et al. |
| 10,799,240 B2 | 10/2020 | Shelton, IV et al. |
| 10,799,306 B2 | 10/2020 | Robinson et al. |
| 10,806,448 B2 | 10/2020 | Shelton, IV et al. |
| 10,806,449 B2 | 10/2020 | Shelton, IV et al. |
| 10,806,450 B2 | 10/2020 | Yates et al. |
| 10,806,451 B2 | 10/2020 | Harris et al. |
| 10,806,453 B2 | 10/2020 | Chen et al. |
| 10,806,479 B2 | 10/2020 | Shelton, IV et al. |
| 10,813,638 B2 | 10/2020 | Shelton, IV et al. |
| 10,813,639 B2 | 10/2020 | Shelton, IV et al. |
| 10,813,640 B2 | 10/2020 | Adams et al. |
| 10,813,641 B2 | 10/2020 | Setser et al. |
| 10,813,683 B2 | 10/2020 | Baxter, III et al. |
| 10,813,705 B2 | 10/2020 | Hares et al. |
| 10,813,710 B2 | 10/2020 | Grubbs |
| 10,820,939 B2 | 11/2020 | Sartor |
| 10,828,028 B2 | 11/2020 | Harris et al. |
| 10,828,030 B2 | 11/2020 | Weir et al. |
| 10,828,032 B2 | 11/2020 | Leimbach et al. |
| 10,828,033 B2 | 11/2020 | Shelton, IV et al. |
| 10,828,089 B2 | 11/2020 | Clark et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,249 B2 | 11/2020 | Schellin et al. |
| 10,835,251 B2 | 11/2020 | Shelton, IV et al. |
| 10,835,330 B2 | 11/2020 | Shelton, IV et al. |
| 10,842,357 B2 | 11/2020 | Moskowitz et al. |
| 10,842,473 B2 | 11/2020 | Scheib et al. |
| 10,842,488 B2 | 11/2020 | Swayze et al. |
| 10,842,489 B2 | 11/2020 | Shelton, IV |
| 10,842,490 B2 | 11/2020 | DiNardo et al. |
| 10,842,491 B2 | 11/2020 | Shelton, IV et al. |
| 10,842,492 B2 | 11/2020 | Shelton, IV et al. |
| 10,842,523 B2 | 11/2020 | Shelton, IV et al. |
| D904,612 S | 12/2020 | Wynn et al. |
| D904,613 S | 12/2020 | Wynn et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,856,866 B2 | 12/2020 | Shelton, IV et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,863,981 B2 | 12/2020 | Overmyer et al. |
| 10,863,984 B2 | 12/2020 | Shelton, IV et al. |
| 10,863,986 B2 | 12/2020 | Yates et al. |
| 10,869,663 B2 | 12/2020 | Shelton, IV et al. |
| 10,869,664 B2 | 12/2020 | Shelton, IV |
| 10,869,665 B2 | 12/2020 | Shelton, IV et al. |
| 10,869,666 B2 | 12/2020 | Shelton, IV et al. |
| 10,869,669 B2 | 12/2020 | Shelton, IV et al. |
| 10,874,290 B2 | 12/2020 | Walen et al. |
| 10,874,391 B2 | 12/2020 | Shelton, IV et al. |
| 10,874,392 B2 | 12/2020 | Scirica et al. |
| 10,874,393 B2 | 12/2020 | Satti, III et al. |
| 10,874,396 B2 | 12/2020 | Moore et al. |
| 10,874,399 B2 | 12/2020 | Zhang |
| 10,879,275 B2 | 12/2020 | Li et al. |
| D907,647 S | 1/2021 | Siebel et al. |
| D907,648 S | 1/2021 | Siebel et al. |
| D908,216 S | 1/2021 | Messerly et al. |
| 10,881,339 B2 | 1/2021 | Peyser et al. |
| 10,881,395 B2 | 1/2021 | Merchant et al. |
| 10,881,396 B2 | 1/2021 | Shelton, IV et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,888,318 B2 | 1/2021 | Parihar et al. |
| 10,888,321 B2 | 1/2021 | Shelton, IV et al. |
| 10,888,322 B2 | 1/2021 | Morgan et al. |
| 10,888,323 B2 | 1/2021 | Chen et al. |
| 10,888,325 B2 | 1/2021 | Harris et al. |
| 10,888,328 B2 | 1/2021 | Shelton, IV et al. |
| 10,888,329 B2 | 1/2021 | Moore et al. |
| 10,888,330 B2 | 1/2021 | Moore et al. |
| 10,888,369 B2 | 1/2021 | Messerly et al. |
| 10,892,899 B2 | 1/2021 | Shelton, IV et al. |
| 10,893,853 B2 | 1/2021 | Shelton, IV et al. |
| 10,893,863 B2 | 1/2021 | Shelton, IV et al. |
| 10,893,864 B2 | 1/2021 | Harris et al. |
| 10,893,867 B2 | 1/2021 | Leimbach et al. |
| 10,898,183 B2 | 1/2021 | Shelton, IV et al. |
| 10,898,184 B2 | 1/2021 | Yates et al. |
| 10,898,185 B2 | 1/2021 | Overmyer et al. |
| 10,898,186 B2 | 1/2021 | Bakos et al. |
| 10,898,190 B2 | 1/2021 | Yates et al. |
| 10,898,193 B2 | 1/2021 | Shelton, IV et al. |
| 10,898,194 B2 | 1/2021 | Moore et al. |
| 10,898,195 B2 | 1/2021 | Moore et al. |
| 10,903,685 B2 | 1/2021 | Yates et al. |
| D910,847 S | 2/2021 | Shelton, IV et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,905,422 B2 | 2/2021 | Bakos et al. |
| 10,905,423 B2 | 2/2021 | Baber et al. |
| 10,905,426 B2 | 2/2021 | Moore et al. |
| 10,905,427 B2 | 2/2021 | Moore et al. |
| 10,911,515 B2 | 2/2021 | Biasi et al. |
| 10,912,559 B2 | 2/2021 | Harris et al. |
| 10,912,562 B2 | 2/2021 | Dunki-Jacobs et al. |
| 10,912,575 B2 | 2/2021 | Shelton, IV et al. |
| 10,918,364 B2 | 2/2021 | Applegate et al. |
| 10,918,380 B2 | 2/2021 | Morgan et al. |
| 10,918,385 B2 | 2/2021 | Overmyer et al. |
| 10,918,386 B2 | 2/2021 | Shelton, IV et al. |
| 10,919,156 B2 | 2/2021 | Roberts et al. |
| 10,925,600 B2 | 2/2021 | McCuen |
| 10,925,605 B2 | 2/2021 | Moore et al. |
| D914,878 S | 3/2021 | Shelton, IV et al. |
| 10,932,772 B2 | 3/2021 | Shelton, IV et al. |

(56) References Cited

U.S. PATENT DOCUMENTS

| | | | |
|---|---|---|---|
| 10,932,774 B2 | 3/2021 | Shelton, IV |
| 10,932,775 B2 | 3/2021 | Shelton, IV et al. |
| 10,932,778 B2 | 3/2021 | Smith et al. |
| 10,932,779 B2 | 3/2021 | Vendely et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,945,728 B2 | 3/2021 | Morgan et al. |
| 10,945,729 B2 | 3/2021 | Shelton, IV et al. |
| 10,945,731 B2 | 3/2021 | Baxter, III et al. |
| 10,952,708 B2 | 3/2021 | Scheib et al. |
| 10,952,726 B2 | 3/2021 | Chowaniec |
| 10,952,727 B2 | 3/2021 | Giordano et al. |
| 10,952,728 B2 | 3/2021 | Shelton, IV et al. |
| 10,952,759 B2 | 3/2021 | Messerly et al. |
| 10,952,767 B2 | 3/2021 | Kostrzewski et al. |
| 10,959,722 B2 | 3/2021 | Morgan et al. |
| 10,959,725 B2 | 3/2021 | Kerr et al. |
| 10,959,726 B2 | 3/2021 | Williams et al. |
| 10,959,727 B2 | 3/2021 | Hunter et al. |
| 10,959,731 B2 | 3/2021 | Casasanta, Jr. et al. |
| 10,959,744 B2 | 3/2021 | Shelton, IV et al. |
| 10,959,797 B2 | 3/2021 | Licht et al. |
| D917,500 S | 4/2021 | Siebel et al. |
| 10,966,627 B2 | 4/2021 | Shelton, IV et al. |
| 10,966,717 B2 | 4/2021 | Shah et al. |
| 10,966,718 B2 | 4/2021 | Shelton, IV et al. |
| 10,966,791 B2 | 4/2021 | Harris et al. |
| 10,973,515 B2 | 4/2021 | Harris et al. |
| 10,973,516 B2 | 4/2021 | Shelton, IV et al. |
| 10,973,517 B2 | 4/2021 | Wixey |
| 10,973,519 B2 | 4/2021 | Weir et al. |
| 10,973,520 B2 | 4/2021 | Shelton, IV et al. |
| 10,980,534 B2 | 4/2021 | Yates et al. |
| 10,980,535 B2 | 4/2021 | Yates et al. |
| 10,980,536 B2 | 4/2021 | Weaner et al. |
| 10,980,537 B2 | 4/2021 | Shelton, IV et al. |
| 10,980,538 B2 | 4/2021 | Nalagatla et al. |
| 10,980,539 B2 | 4/2021 | Harris et al. |
| 10,980,560 B2 | 4/2021 | Shelton, IV et al. |
| 10,983,646 B2 | 4/2021 | Yoon et al. |
| 10,987,102 B2 | 4/2021 | Gonzalez et al. |
| 10,987,178 B2 | 4/2021 | Shelton, IV et al. |
| 10,993,713 B2 | 5/2021 | Shelton, IV et al. |
| 10,993,715 B2 | 5/2021 | Shelton, IV et al. |
| 10,993,716 B2 | 5/2021 | Shelton, IV et al. |
| 10,993,717 B2 | 5/2021 | Shelton, IV et al. |
| 11,000,274 B2 | 5/2021 | Shelton, IV et al. |
| 11,000,275 B2 | 5/2021 | Shelton, IV et al. |
| 11,000,277 B2 | 5/2021 | Giordano et al. |
| 11,000,278 B2 | 5/2021 | Shelton, IV et al. |
| 11,000,279 B2 | 5/2021 | Shelton, IV et al. |
| 11,005,291 B2 | 5/2021 | Calderoni |
| 11,006,951 B2 | 5/2021 | Giordano et al. |
| 11,006,955 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,511 B2 | 5/2021 | Huang et al. |
| 11,013,552 B2 | 5/2021 | Widenhouse et al. |
| 11,013,563 B2 | 5/2021 | Shelton, IV et al. |
| 11,020,016 B2 | 6/2021 | Wallace et al. |
| 11,020,112 B2 | 6/2021 | Shelton, IV et al. |
| 11,020,113 B2 | 6/2021 | Shelton, IV et al. |
| 11,020,114 B2 | 6/2021 | Shelton, IV et al. |
| 11,020,115 B2 | 6/2021 | Scheib et al. |
| 11,020,172 B2 | 6/2021 | Garrison |
| 11,026,678 B2 | 6/2021 | Overmyer et al. |
| 11,026,680 B2 | 6/2021 | Shelton, IV et al. |
| 11,026,684 B2 | 6/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,033,267 B2 | 6/2021 | Shelton, IV et al. |
| 11,039,834 B2 | 6/2021 | Harris et al. |
| 11,039,836 B2 | 6/2021 | Shelton, IV et al. |
| 11,039,837 B2 | 6/2021 | Shelton, IV et al. |
| 11,039,849 B2 | 6/2021 | Bucciaglia et al. |
| 11,045,189 B2 | 6/2021 | Yates et al. |
| 11,045,191 B2 | 6/2021 | Shelton, IV et al. |
| 11,045,192 B2 | 6/2021 | Harris et al. |
| 11,045,196 B2 | 6/2021 | Olson et al. |
| 11,045,197 B2 | 6/2021 | Shelton, IV et al. |
| 11,045,199 B2 | 6/2021 | Mozdzierz et al. |
| 11,045,270 B2 | 6/2021 | Shelton, IV et al. |
| 11,051,807 B2 | 7/2021 | Shelton, IV et al. |
| 11,051,810 B2 | 7/2021 | Harris et al. |
| 11,051,811 B2 | 7/2021 | Shelton, IV et al. |
| 11,051,813 B2 | 7/2021 | Shelton, IV et al. |
| 11,051,836 B2 | 7/2021 | Shelton, IV et al. |
| 11,051,840 B2 | 7/2021 | Shelton, IV et al. |
| 11,051,873 B2 | 7/2021 | Wiener et al. |
| 11,058,418 B2 | 7/2021 | Shelton, IV et al. |
| 11,058,420 B2 | 7/2021 | Shelton, IV et al. |
| 11,058,422 B2 | 7/2021 | Harris et al. |
| 11,058,423 B2 | 7/2021 | Shelton, IV et al. |
| 11,058,424 B2 | 7/2021 | Shelton, IV et al. |
| 11,058,425 B2 | 7/2021 | Widenhouse et al. |
| 11,058,426 B2 | 7/2021 | Nalagatla et al. |
| 11,058,498 B2 | 7/2021 | Shelton, IV et al. |
| 11,064,997 B2 | 7/2021 | Shelton, IV et al. |
| 11,064,998 B2 | 7/2021 | Shelton, IV |
| 11,065,000 B2 | 7/2021 | Shankarsetty et al. |
| 11,065,048 B2 | 7/2021 | Messerly et al. |
| 11,069,012 B2 | 7/2021 | Shelton, IV et al. |
| 11,071,542 B2 | 7/2021 | Chen et al. |
| 11,071,543 B2 | 7/2021 | Shelton, IV et al. |
| 11,071,545 B2 | 7/2021 | Baber et al. |
| 11,071,554 B2 | 7/2021 | Parfett et al. |
| 11,071,560 B2 | 7/2021 | Deck et al. |
| 11,076,853 B2 | 8/2021 | Parfett et al. |
| 11,076,854 B2 | 8/2021 | Baber et al. |
| 11,076,921 B2 | 8/2021 | Shelton, IV et al. |
| 11,076,929 B2 | 8/2021 | Shelton, IV et al. |
| 11,083,452 B2 | 8/2021 | Schmid et al. |
| 11,083,453 B2 | 8/2021 | Shelton, IV et al. |
| 11,083,454 B2 | 8/2021 | Harris et al. |
| 11,083,455 B2 | 8/2021 | Shelton, IV et al. |
| 11,083,456 B2 | 8/2021 | Shelton, IV et al. |
| 11,083,457 B2 | 8/2021 | Shelton, IV et al. |
| 11,083,458 B2 | 8/2021 | Harris et al. |
| 11,090,045 B2 | 8/2021 | Shelton, IV |
| 11,090,046 B2 | 8/2021 | Shelton, IV et al. |
| 11,090,047 B2 | 8/2021 | Shelton, IV et al. |
| 11,090,048 B2 | 8/2021 | Fanelli et al. |
| 11,090,049 B2 | 8/2021 | Bakos et al. |
| 11,090,075 B2 | 8/2021 | Hunter et al. |
| 11,096,688 B2 | 8/2021 | Shelton, IV et al. |
| 11,096,689 B2 | 8/2021 | Overmyer et al. |
| 11,100,631 B2 | 8/2021 | Yates et al. |
| 11,103,241 B2 | 8/2021 | Yates et al. |
| 11,103,248 B2 | 8/2021 | Shelton, IV et al. |
| 11,103,268 B2 | 8/2021 | Shelton, IV et al. |
| 11,103,269 B2 | 8/2021 | Shelton, IV et al. |
| 11,103,301 B2 | 8/2021 | Messerly et al. |
| 11,109,858 B2 | 9/2021 | Shelton, IV et al. |
| 11,109,859 B2 | 9/2021 | Overmyer et al. |
| 11,109,860 B2 | 9/2021 | Shelton, IV et al. |
| 11,109,866 B2 | 9/2021 | Shelton, IV et al. |
| 11,109,878 B2 | 9/2021 | Shelton, IV et al. |
| 11,109,925 B2 | 9/2021 | Cooper et al. |
| 11,116,485 B2 | 9/2021 | Scheib et al. |
| 11,116,502 B2 | 9/2021 | Shelton, IV et al. |
| 11,116,594 B2 | 9/2021 | Beardsley |
| 11,123,069 B2 | 9/2021 | Baxter, III et al. |
| 11,123,070 B2 | 9/2021 | Shelton, IV et al. |
| 11,129,611 B2 | 9/2021 | Shelton, IV et al. |
| 11,129,613 B2 | 9/2021 | Harris et al. |
| 11,129,615 B2 | 9/2021 | Scheib et al. |
| 11,129,616 B2 | 9/2021 | Shelton, IV et al. |
| 11,129,634 B2 | 9/2021 | Scheib et al. |

(56) References Cited

U.S. PATENT DOCUMENTS

| | | |
|---|---|---|
| 11,129,636 B2 | 9/2021 | Shelton, IV et al. |
| 11,129,666 B2 | 9/2021 | Messerly et al. |
| 11,129,680 B2 | 9/2021 | Shelton, IV et al. |
| 11,132,462 B2 | 9/2021 | Shelton, IV et al. |
| 11,133,106 B2 | 9/2021 | Shelton, IV et al. |
| 11,134,938 B2 | 10/2021 | Timm et al. |
| 11,134,940 B2 | 10/2021 | Shelton, IV et al. |
| 11,134,942 B2 | 10/2021 | Harris et al. |
| 11,134,943 B2 | 10/2021 | Giordano et al. |
| 11,134,944 B2 | 10/2021 | Wise et al. |
| 11,134,947 B2 | 10/2021 | Shelton, IV et al. |
| 11,135,352 B2 | 10/2021 | Shelton, IV et al. |
| 11,141,153 B2 | 10/2021 | Shelton, IV et al. |
| 11,141,154 B2 | 10/2021 | Shelton, IV et al. |
| 11,141,155 B2 | 10/2021 | Shelton, IV |
| 11,141,156 B2 | 10/2021 | Shelton, IV |
| 11,141,159 B2 | 10/2021 | Scheib et al. |
| 11,141,160 B2 | 10/2021 | Shelton, IV et al. |
| 11,147,547 B2 | 10/2021 | Shelton, IV et al. |
| 11,147,549 B2 | 10/2021 | Timm et al. |
| 11,147,551 B2 | 10/2021 | Shelton, IV |
| 11,147,553 B2 | 10/2021 | Shelton, IV |
| 11,147,554 B2 | 10/2021 | Aronhalt et al. |
| 11,154,296 B2 | 10/2021 | Aronhalt et al. |
| 11,154,297 B2 | 10/2021 | Swayze et al. |
| 11,154,298 B2 | 10/2021 | Timm et al. |
| 11,154,299 B2 | 10/2021 | Shelton, IV et al. |
| 11,154,300 B2 | 10/2021 | Nalagatla et al. |
| 11,154,301 B2 | 10/2021 | Beckman et al. |
| 11,160,551 B2 | 11/2021 | Shelton, IV et al. |
| 11,160,553 B2 | 11/2021 | Simms et al. |
| 11,160,601 B2 | 11/2021 | Worrell et al. |
| 11,166,716 B2 | 11/2021 | Shelton, IV et al. |
| 11,166,717 B2 | 11/2021 | Shelton, IV et al. |
| 11,166,720 B2 | 11/2021 | Giordano et al. |
| 11,166,772 B2 | 11/2021 | Shelton, IV et al. |
| 11,166,773 B2 | 11/2021 | Ragosta et al. |
| 11,172,580 B2 | 11/2021 | Gaertner, II |
| 11,172,927 B2 | 11/2021 | Shelton, IV |
| 11,172,929 B2 | 11/2021 | Shelton, IV |
| 11,179,150 B2 | 11/2021 | Yates et al. |
| 11,179,152 B2 | 11/2021 | Morgan et al. |
| 11,179,155 B2 | 11/2021 | Shelton, IV et al. |
| 11,179,208 B2 | 11/2021 | Yates et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,191,543 B2 | 12/2021 | Overmyer et al. |
| 11,191,545 B2 | 12/2021 | Vendely et al. |
| 11,197,668 B2 | 12/2021 | Shelton, IV et al. |
| 11,197,670 B2 | 12/2021 | Shelton, IV et al. |
| 11,197,671 B2 | 12/2021 | Shelton, IV et al. |
| 11,197,672 B2 | 12/2021 | Dunki-Jacobs et al. |
| 11,202,570 B2 | 12/2021 | Shelton, IV et al. |
| 11,202,631 B2 | 12/2021 | Shelton, IV et al. |
| 11,202,633 B2 | 12/2021 | Harris et al. |
| 11,207,064 B2 | 12/2021 | Shelton, IV et al. |
| 11,207,065 B2 | 12/2021 | Harris et al. |
| 11,207,067 B2 | 12/2021 | Shelton, IV et al. |
| 11,207,089 B2 | 12/2021 | Kostrzewski et al. |
| 11,207,090 B2 | 12/2021 | Shelton, IV et al. |
| 11,207,146 B2 | 12/2021 | Shelton, IV et al. |
| 11,213,293 B2 | 1/2022 | Worthington et al. |
| 11,213,294 B2 | 1/2022 | Shelton, IV et al. |
| 11,213,302 B2 | 1/2022 | Parfett et al. |
| 11,213,359 B2 | 1/2022 | Shelton, IV et al. |
| 11,219,453 B2 | 1/2022 | Shelton, IV et al. |
| 11,219,455 B2 | 1/2022 | Shelton, IV et al. |
| 11,224,423 B2 | 1/2022 | Shelton, IV et al. |
| 11,224,426 B2 | 1/2022 | Shelton, IV et al. |
| 11,224,427 B2 | 1/2022 | Shelton, IV et al. |
| 11,224,428 B2 | 1/2022 | Scott et al. |
| 11,224,454 B2 | 1/2022 | Shelton, IV et al. |
| 11,224,497 B2 | 1/2022 | Shelton, IV et al. |
| 11,229,436 B2 | 1/2022 | Shelton, IV et al. |
| 11,229,437 B2 | 1/2022 | Shelton, IV et al. |
| 11,234,698 B2 | 2/2022 | Shelton, IV et al. |
| 11,234,700 B2 | 2/2022 | Ragosta et al. |
| 11,241,229 B2 | 2/2022 | Shelton, IV et al. |
| 11,241,230 B2 | 2/2022 | Shelton, IV et al. |
| 11,241,235 B2 | 2/2022 | Shelton, IV et al. |
| 11,246,590 B2 | 2/2022 | Swayze et al. |
| 11,246,592 B2 | 2/2022 | Shelton, IV et al. |
| 11,246,616 B2 | 2/2022 | Shelton, IV et al. |
| 11,246,618 B2 | 2/2022 | Hall et al. |
| 11,246,678 B2 | 2/2022 | Shelton, IV et al. |
| 11,253,254 B2 | 2/2022 | Kimball et al. |
| 11,253,256 B2 | 2/2022 | Harris et al. |
| 11,259,799 B2 | 3/2022 | Overmyer et al. |
| 11,259,803 B2 | 3/2022 | Shelton, IV et al. |
| 11,259,805 B2 | 3/2022 | Shelton, IV et al. |
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,406 B2 | 3/2022 | Leimbach et al. |
| 11,266,409 B2 | 3/2022 | Huitema et al. |
| 11,266,410 B2 | 3/2022 | Shelton, IV et al. |
| 11,266,468 B2 | 3/2022 | Shelton, IV et al. |
| 11,272,927 B2 | 3/2022 | Swayze et al. |
| 11,272,928 B2 | 3/2022 | Shelton, IV |
| 11,272,931 B2 | 3/2022 | Boudreaux et al. |
| 11,272,938 B2 | 3/2022 | Shelton, IV et al. |
| 11,278,279 B2 | 3/2022 | Morgan et al. |
| 11,278,280 B2 | 3/2022 | Shelton, IV et al. |
| 11,278,284 B2 | 3/2022 | Shelton, IV et al. |
| 11,291,443 B2 | 4/2022 | Viola et al. |
| 11,304,697 B2 | 4/2022 | Fanelli et al. |
| 11,304,704 B2 | 4/2022 | Thomas et al. |
| 11,311,295 B2 | 4/2022 | Wingardner et al. |
| D950,728 S | 5/2022 | Bakos et al. |
| D952,144 S | 5/2022 | Boudreaux |
| 11,317,912 B2 | 5/2022 | Jenkins et al. |
| 11,317,978 B2 | 5/2022 | Cameron et al. |
| 11,369,366 B2 | 6/2022 | Scheib et al. |
| 11,376,002 B2 | 7/2022 | Shelton, IV et al. |
| 11,376,082 B2 | 7/2022 | Shelton, IV et al. |
| 11,382,704 B2 | 7/2022 | Overmyer et al. |
| 11,406,442 B2 | 8/2022 | Davison et al. |
| 11,413,041 B2 | 8/2022 | Viola et al. |
| D964,564 S | 9/2022 | Boudreaux |
| 11,439,391 B2 | 9/2022 | Bruns et al. |
| 11,452,526 B2 | 9/2022 | Ross et al. |
| D966,512 S | 10/2022 | Shelton, IV et al. |
| D967,421 S | 10/2022 | Shelton, IV et al. |
| D971,232 S | 11/2022 | Siebel et al. |
| 11,484,309 B2 | 11/2022 | Harris et al. |
| 11,484,312 B2 | 11/2022 | Shelton, IV et al. |
| 11,510,673 B1 | 11/2022 | Chen et al. |
| 11,523,824 B2 | 12/2022 | Williams |
| 11,523,859 B2 | 12/2022 | Shelton, IV et al. |
| D974,560 S | 1/2023 | Shelton, IV et al. |
| D975,278 S | 1/2023 | Shelton, IV et al. |
| D975,850 S | 1/2023 | Shelton, IV et al. |
| D975,851 S | 1/2023 | Shelton, IV et al. |
| D976,401 S | 1/2023 | Shelton, IV et al. |
| D980,425 S | 3/2023 | Baxter, III |
| 11,607,278 B2 | 3/2023 | Shelton, IV et al. |
| 11,628,006 B2 | 4/2023 | Henderson et al. |
| 11,638,582 B2 | 5/2023 | Bakos et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0030219 A1 | 10/2001 | Green et al. |
| 2001/0034530 A1 | 10/2001 | Malackowski et al. |
| 2001/0045442 A1 | 11/2001 | Whitman |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0023126 A1 | 2/2002 | Flavin |
| 2002/0029032 A1 | 3/2002 | Arkin |
| 2002/0029036 A1 | 3/2002 | Goble et al. |
| 2002/0042620 A1 | 4/2002 | Julian et al. |

(56) References Cited

U.S. PATENT DOCUMENTS

| | | |
|---|---|---|
| 2002/0045905 A1 | 4/2002 | Gerbi et al. |
| 2002/0054158 A1 | 5/2002 | Asami |
| 2002/0065535 A1 | 5/2002 | Kneifel et al. |
| 2002/0066764 A1 | 6/2002 | Perry et al. |
| 2002/0077660 A1 | 6/2002 | Kayan et al. |
| 2002/0082612 A1 | 6/2002 | Moll et al. |
| 2002/0087048 A1 | 7/2002 | Brock et al. |
| 2002/0087148 A1 | 7/2002 | Brock et al. |
| 2002/0091374 A1 | 7/2002 | Cooper |
| 2002/0095175 A1 | 7/2002 | Brock et al. |
| 2002/0099374 A1 | 7/2002 | Pendekanti et al. |
| 2002/0103494 A1 | 8/2002 | Pacey |
| 2002/0111621 A1 | 8/2002 | Wallace et al. |
| 2002/0111624 A1 | 8/2002 | Witt et al. |
| 2002/0116063 A1 | 8/2002 | Giannetti et al. |
| 2002/0117533 A1 | 8/2002 | Milliman et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0133236 A1 | 9/2002 | Rousseau |
| 2002/0134811 A1 | 9/2002 | Napier et al. |
| 2002/0135474 A1 | 9/2002 | Sylliassen |
| 2002/0138086 A1 | 9/2002 | Sixto et al. |
| 2002/0143340 A1 | 10/2002 | Kaneko |
| 2002/0143346 A1 * | 10/2002 | McGuckin, Jr. ... A61B 17/3205 606/151 |
| 2002/0151770 A1 | 10/2002 | Noll et al. |
| 2002/0156497 A1 | 10/2002 | Nagase et al. |
| 2002/0158593 A1 | 10/2002 | Henderson et al. |
| 2002/0161277 A1 | 10/2002 | Boone et al. |
| 2002/0177848 A1 | 11/2002 | Truckai et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0004610 A1 | 1/2003 | Niemeyer et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0018323 A1 | 1/2003 | Wallace et al. |
| 2003/0028236 A1 | 2/2003 | Gillick et al. |
| 2003/0040670 A1 | 2/2003 | Govari |
| 2003/0045835 A1 | 3/2003 | Anderson et al. |
| 2003/0047230 A1 | 3/2003 | Kim |
| 2003/0047582 A1 | 3/2003 | Sonnenschein et al. |
| 2003/0050628 A1 | 3/2003 | Whitman et al. |
| 2003/0050654 A1 | 3/2003 | Whitman et al. |
| 2003/0066858 A1 | 4/2003 | Holgersson |
| 2003/0078647 A1 | 4/2003 | Vallana et al. |
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0093160 A1 | 5/2003 | Maksimovic et al. |
| 2003/0094356 A1 | 5/2003 | Waldron |
| 2003/0096158 A1 | 5/2003 | Takano et al. |
| 2003/0105475 A1 | 6/2003 | Sancoff et al. |
| 2003/0114851 A1 | 6/2003 | Truckai et al. |
| 2003/0121586 A1 | 7/2003 | Mitra et al. |
| 2003/0135204 A1 | 7/2003 | Lee et al. |
| 2003/0135388 A1 | 7/2003 | Martucci et al. |
| 2003/0139741 A1 | 7/2003 | Goble et al. |
| 2003/0144660 A1 | 7/2003 | Mollenauer |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0158463 A1 | 8/2003 | Julian et al. |
| 2003/0163029 A1 | 8/2003 | Sonnenschein et al. |
| 2003/0163085 A1 | 8/2003 | Tanner et al. |
| 2003/0164172 A1 | 9/2003 | Chumas et al. |
| 2003/0181800 A1 | 9/2003 | Bonutti |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216619 A1 | 11/2003 | Scirica et al. |
| 2003/0216732 A1 | 11/2003 | Truckai et al. |
| 2003/0220541 A1 | 11/2003 | Salisbury et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034287 A1 | 2/2004 | Hickle |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092967 A1 | 5/2004 | Sancoff et al. |
| 2004/0092992 A1 | 5/2004 | Adams et al. |
| 2004/0093020 A1 | 5/2004 | Sinton |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0231870 A1 | 11/2004 | McCormick et al. |
| 2004/0232194 A1 | 11/2004 | Pedicini et al. |
| 2004/0232197 A1 | 11/2004 | Shelton, IV et al. |
| 2004/0232201 A1 | 11/2004 | Wenchell et al. |
| 2004/0236352 A1 | 11/2004 | Wang et al. |
| 2004/0239582 A1 | 12/2004 | Seymour |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0254680 A1 | 12/2004 | Sunaoshi |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0023325 A1 | 2/2005 | Gresham et al. |
| 2005/0032511 A1 | 2/2005 | Malone et al. |
| 2005/0033352 A1 | 2/2005 | Zepf et al. |
| 2005/0044489 A1 | 2/2005 | Yamagami et al. |

(56) References Cited

U.S. PATENT DOCUMENTS

| | | |
|---|---|---|
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0067548 A1 | 3/2005 | Inoue |
| 2005/0070925 A1 | 3/2005 | Shelton et al. |
| 2005/0070929 A1 | 3/2005 | Dalessandro et al. |
| 2005/0074593 A1 | 4/2005 | Day et al. |
| 2005/0075561 A1 | 4/2005 | Golden |
| 2005/0079088 A1 | 4/2005 | Wirth et al. |
| 2005/0080342 A1 | 4/2005 | Gilreath et al. |
| 2005/0085693 A1 | 4/2005 | Belson et al. |
| 2005/0085838 A1 | 4/2005 | Thompson et al. |
| 2005/0090709 A1 | 4/2005 | Okada et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0119524 A1 | 6/2005 | Sekine et al. |
| 2005/0120836 A1 | 6/2005 | Anderson |
| 2005/0124855 A1 | 6/2005 | Jaffe et al. |
| 2005/0125028 A1 | 6/2005 | Looper et al. |
| 2005/0125897 A1 | 6/2005 | Wyslucha et al. |
| 2005/0129730 A1 | 6/2005 | Pang et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0145672 A1 | 7/2005 | Schwemberger et al. |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0191936 A1 | 9/2005 | Marine et al. |
| 2005/0197859 A1 | 9/2005 | Wilson et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0242950 A1 | 11/2005 | Lindsay et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0251110 A1 | 11/2005 | Nixon |
| 2005/0256452 A1 | 11/2005 | DeMarchi et al. |
| 2005/0256546 A1 | 11/2005 | Vaisnys et al. |
| 2005/0258963 A1 | 11/2005 | Rodriguez et al. |
| 2005/0261676 A1 | 11/2005 | Hall et al. |
| 2005/0263563 A1 | 12/2005 | Racenet et al. |
| 2005/0267455 A1 | 12/2005 | Eggers et al. |
| 2005/0267464 A1 | 12/2005 | Truckai et al. |
| 2005/0267529 A1 | 12/2005 | Crockett et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |
| 2006/0000867 A1 | 1/2006 | Shelton et al. |
| 2006/0008787 A1 | 1/2006 | Hayman et al. |
| 2006/0011698 A1 | 1/2006 | Okada et al. |
| 2006/0015009 A1 | 1/2006 | Jaffe et al. |
| 2006/0019056 A1 | 1/2006 | Turner et al. |
| 2006/0020167 A1 | 1/2006 | Sitzmann |
| 2006/0020258 A1 | 1/2006 | Strauss et al. |
| 2006/0020272 A1 | 1/2006 | Gildenberg |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0053951 A1 | 3/2006 | Revelis et al. |
| 2006/0064086 A1 | 3/2006 | Odom |
| 2006/0079735 A1 | 4/2006 | Martone et al. |
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142656 A1 | 6/2006 | Malackowski et al. |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0189440 A1 | 8/2006 | Gravagne |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0226196 A1 | 10/2006 | Hueil et al. |
| 2006/0226957 A1 | 10/2006 | Miller et al. |
| 2006/0235368 A1 | 10/2006 | Oz |
| 2006/0241666 A1 | 10/2006 | Briggs et al. |
| 2006/0241691 A1 | 10/2006 | Wilk |
| 2006/0244460 A1 | 11/2006 | Weaver |
| 2006/0247584 A1 | 11/2006 | Sheetz et al. |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289600 A1 | 12/2006 | Wales et al. |

(56) References Cited

U.S. PATENT DOCUMENTS

| | | |
|---|---|---|
| 2006/0289602 A1 | 12/2006 | Wales et al. |
| 2006/0291981 A1 | 12/2006 | Viola et al. |
| 2007/0005045 A1 | 1/2007 | Mintz et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0016272 A1 | 1/2007 | Thompson et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027459 A1 | 2/2007 | Horvath et al. |
| 2007/0027468 A1 | 2/2007 | Wales et al. |
| 2007/0027551 A1 | 2/2007 | Farnsworth et al. |
| 2007/0034669 A1 | 2/2007 | de la Torre et al. |
| 2007/0043338 A1 | 2/2007 | Moll et al. |
| 2007/0043384 A1 | 2/2007 | Ortiz et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0055305 A1 | 3/2007 | Schnyder et al. |
| 2007/0069851 A1 | 3/2007 | Sung et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0103437 A1 | 5/2007 | Rosenberg |
| 2007/0106113 A1 | 5/2007 | Ravo |
| 2007/0106317 A1 | 5/2007 | Shelton et al. |
| 2007/0118115 A1 | 5/2007 | Artale et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0152829 A1 | 7/2007 | Lindsay et al. |
| 2007/0155010 A1 | 7/2007 | Farnsworth et al. |
| 2007/0162056 A1 | 7/2007 | Gerbi et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0173872 A1 | 7/2007 | Neuenfeldt |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179476 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0191915 A1 | 8/2007 | Strother et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0221701 A1 | 9/2007 | Ortiz et al. |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0244496 A1 | 10/2007 | Hellenkamp |
| 2007/0246505 A1 | 10/2007 | Pace-Floridia et al. |
| 2007/0250093 A1 | 10/2007 | Makower et al. |
| 2007/0260132 A1 | 11/2007 | Sterling |
| 2007/0260242 A1 | 11/2007 | Dycus et al. |
| 2007/0262592 A1 | 11/2007 | Hwang et al. |
| 2007/0270660 A1 | 11/2007 | Caylor et al. |
| 2007/0270790 A1 | 11/2007 | Smith et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0290027 A1 | 12/2007 | Maatta et al. |
| 2007/0296286 A1 | 12/2007 | Avenell |
| 2008/0000941 A1 | 1/2008 | Sonnenschein et al. |
| 2008/0003196 A1 | 1/2008 | Jonn et al. |
| 2008/0007237 A1 | 1/2008 | Nagashima et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0046000 A1 | 2/2008 | Lee et al. |
| 2008/0051833 A1 | 2/2008 | Gramuglia et al. |
| 2008/0064920 A1 | 3/2008 | Bakos et al. |
| 2008/0064921 A1 | 3/2008 | Larkin et al. |
| 2008/0065153 A1 | 3/2008 | Allard et al. |
| 2008/0069736 A1 | 3/2008 | Mingerink et al. |
| 2008/0071328 A1 | 3/2008 | Haubrich et al. |
| 2008/0077158 A1 | 3/2008 | Haider et al. |
| 2008/0078802 A1 | 4/2008 | Hess et al. |
| 2008/0081948 A1 | 4/2008 | Weisenburgh et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0083811 A1 | 4/2008 | Marczyk |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0094228 A1 | 4/2008 | Welch et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0126984 A1 | 5/2008 | Fleishman et al. |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140088 A1 | 6/2008 | Orban, III |
| 2008/0140115 A1 | 6/2008 | Stopek |
| 2008/0140159 A1 | 6/2008 | Bornhoft et al. |
| 2008/0149682 A1 | 6/2008 | Uhm |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0208058 A1 | 8/2008 | Sabata et al. |
| 2008/0214967 A1 | 9/2008 | Aranyi et al. |
| 2008/0216704 A1 | 9/2008 | Eisenbeis et al. |
| 2008/0217376 A1 | 9/2008 | Clauson et al. |
| 2008/0234709 A1 | 9/2008 | Houser |
| 2008/0234866 A1 | 9/2008 | Kishi et al. |

(56) References Cited

U.S. PATENT DOCUMENTS

| | | |
|---|---|---|
| 2008/0242939 A1 | 10/2008 | Johnston |
| 2008/0243088 A1 | 10/2008 | Evans |
| 2008/0243143 A1 | 10/2008 | Kuhns et al. |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0255420 A1 | 10/2008 | Lee et al. |
| 2008/0255421 A1 | 10/2008 | Hegeman et al. |
| 2008/0255663 A1 | 10/2008 | Akpek et al. |
| 2008/0262654 A1 | 10/2008 | Omori et al. |
| 2008/0269596 A1 | 10/2008 | Revie et al. |
| 2008/0281171 A1 | 11/2008 | Fennell et al. |
| 2008/0281332 A1 | 11/2008 | Taylor |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0296347 A1 | 12/2008 | Shelton, IV et al. |
| 2008/0297287 A1 | 12/2008 | Shachar et al. |
| 2008/0298784 A1 | 12/2008 | Kastner |
| 2008/0308504 A1 | 12/2008 | Hallan et al. |
| 2008/0308602 A1 | 12/2008 | Timm et al. |
| 2008/0308603 A1 | 12/2008 | Shelton et al. |
| 2008/0308607 A1 | 12/2008 | Timm et al. |
| 2008/0308807 A1 | 12/2008 | Yamazaki et al. |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0007014 A1 | 1/2009 | Coomer et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0030437 A1 | 1/2009 | Houser et al. |
| 2009/0043253 A1 | 2/2009 | Podaima |
| 2009/0048583 A1 | 2/2009 | Williams et al. |
| 2009/0048589 A1 | 2/2009 | Takashino et al. |
| 2009/0053288 A1 | 2/2009 | Eskridge, Jr. et al. |
| 2009/0057369 A1 | 3/2009 | Smith et al. |
| 2009/0069806 A1 | 3/2009 | De La Mora Levy et al. |
| 2009/0076506 A1 | 3/2009 | Baker |
| 2009/0076510 A1 | 3/2009 | Bell et al. |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0110533 A1 | 4/2009 | Jinno |
| 2009/0112234 A1 | 4/2009 | Crainich et al. |
| 2009/0114701 A1 | 5/2009 | Zemlok et al. |
| 2009/0118762 A1 | 5/2009 | Crainich et al. |
| 2009/0119011 A1 | 5/2009 | Kondo et al. |
| 2009/0120994 A1 | 5/2009 | Murray et al. |
| 2009/0131819 A1 | 5/2009 | Ritchie et al. |
| 2009/0132400 A1 | 5/2009 | Conway |
| 2009/0135280 A1 | 5/2009 | Johnston et al. |
| 2009/0138003 A1 | 5/2009 | Deville et al. |
| 2009/0143797 A1 | 6/2009 | Smith et al. |
| 2009/0143855 A1 | 6/2009 | Weber et al. |
| 2009/0149871 A9 | 6/2009 | Kagan et al. |
| 2009/0167548 A1 | 7/2009 | Sugahara |
| 2009/0171147 A1 | 7/2009 | Lee et al. |
| 2009/0177218 A1 | 7/2009 | Young et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0196903 A1 | 8/2009 | Kliman |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0204126 A1 | 8/2009 | Le |
| 2009/0204925 A1 | 8/2009 | Bhat et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0236401 A1 | 9/2009 | Cole et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0248100 A1 | 10/2009 | Vaisnys et al. |
| 2009/0253959 A1 | 10/2009 | Yoshie et al. |
| 2009/0255974 A1 | 10/2009 | Viola |
| 2009/0261141 A1 | 10/2009 | Stratton et al. |
| 2009/0262078 A1 | 10/2009 | Pizzi |
| 2009/0264940 A1 | 10/2009 | Beale et al. |
| 2009/0270895 A1 | 10/2009 | Churchill et al. |
| 2009/0273353 A1 | 11/2009 | Kroh et al. |
| 2009/0277288 A1 | 11/2009 | Doepker et al. |
| 2009/0278406 A1 | 11/2009 | Hoffman |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0318936 A1 | 12/2009 | Harris et al. |
| 2009/0325859 A1 | 12/2009 | Ameer et al. |
| 2010/0002013 A1 | 1/2010 | Kagaya |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016853 A1 | 1/2010 | Burbank |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0030239 A1 | 2/2010 | Viola et al. |
| 2010/0032179 A1 | 2/2010 | Hanspers et al. |
| 2010/0036370 A1 | 2/2010 | Mirel et al. |
| 2010/0036441 A1 | 2/2010 | Procter |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069833 A1 | 3/2010 | Wenderow et al. |
| 2010/0069942 A1 | 3/2010 | Shelton, IV |
| 2010/0076433 A1 | 3/2010 | Taylor et al. |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094312 A1 | 4/2010 | Ruiz Morales et al. |
| 2010/0094340 A1 | 4/2010 | Stopek et al. |
| 2010/0094400 A1 | 4/2010 | Bolduc et al. |
| 2010/0100123 A1 | 4/2010 | Bennett |
| 2010/0100124 A1 | 4/2010 | Calabrese et al. |
| 2010/0106167 A1 | 4/2010 | Boulnois et al. |
| 2010/0116519 A1 | 5/2010 | Gareis |
| 2010/0122339 A1 | 5/2010 | Boccacci |
| 2010/0125786 A1 | 5/2010 | Ozawa et al. |
| 2010/0133317 A1 | 6/2010 | Shelton, IV et al. |
| 2010/0137990 A1 | 6/2010 | Apatsidis et al. |
| 2010/0138659 A1 | 6/2010 | Carmichael et al. |
| 2010/0145146 A1 | 6/2010 | Melder |
| 2010/0147921 A1 | 6/2010 | Olson |
| 2010/0147922 A1 | 6/2010 | Olson |
| 2010/0159435 A1 | 6/2010 | Mueller et al. |
| 2010/0168741 A1 | 7/2010 | Sanai et al. |
| 2010/0179022 A1 | 7/2010 | Shirokoshi |
| 2010/0180711 A1 | 7/2010 | Kilibarda et al. |
| 2010/0187285 A1 | 7/2010 | Harris et al. |
| 2010/0191255 A1 | 7/2010 | Crainich et al. |

(56) References Cited

U.S. PATENT DOCUMENTS

| | | |
|---|---|---|
| 2010/0191262 A1 | 7/2010 | Harris et al. |
| 2010/0191292 A1 | 7/2010 | DeMeo et al. |
| 2010/0193566 A1 | 8/2010 | Scheib et al. |
| 2010/0194541 A1 | 8/2010 | Stevenson et al. |
| 2010/0198159 A1 | 8/2010 | Voss et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0218019 A1 | 8/2010 | Eckhard |
| 2010/0222901 A1 | 9/2010 | Swayze et al. |
| 2010/0228250 A1 | 9/2010 | Brogna |
| 2010/0234687 A1 | 9/2010 | Azarbarzin et al. |
| 2010/0241115 A1 | 9/2010 | Benamou et al. |
| 2010/0241137 A1 | 9/2010 | Doyle et al. |
| 2010/0245102 A1 | 9/2010 | Yokoi |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267525 A1 | 10/2010 | Tanner |
| 2010/0267662 A1 | 10/2010 | Fielder et al. |
| 2010/0274160 A1 | 10/2010 | Yachi et al. |
| 2010/0291184 A1 | 11/2010 | Clark et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0325568 A1 | 12/2010 | Pedersen et al. |
| 2010/0327041 A1 | 12/2010 | Milliman et al. |
| 2010/0331856 A1 | 12/2010 | Carlson et al. |
| 2011/0006101 A1 | 1/2011 | Hall et al. |
| 2011/0009694 A1 | 1/2011 | Schultz et al. |
| 2011/0009863 A1 | 1/2011 | Marczyk et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0028991 A1 | 2/2011 | Ikeda et al. |
| 2011/0029003 A1 | 2/2011 | Lavigne et al. |
| 2011/0029270 A1 | 2/2011 | Mueglitz |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0056717 A1 | 3/2011 | Herisse |
| 2011/0060363 A1 | 3/2011 | Hess et al. |
| 2011/0066156 A1 | 3/2011 | McGahan et al. |
| 2011/0066243 A1 | 3/2011 | Rivin et al. |
| 2011/0071473 A1 | 3/2011 | Rogers et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0095067 A1 | 4/2011 | Ohdaira |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0118708 A1 | 5/2011 | Burbank et al. |
| 2011/0118754 A1 | 5/2011 | Dachs, II et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0189957 A1 | 8/2011 | Hocke |
| 2011/0192882 A1 | 8/2011 | Hess et al. |
| 2011/0198381 A1 | 8/2011 | McCardle et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0220381 A1 | 9/2011 | Friese et al. |
| 2011/0224543 A1 | 9/2011 | Johnson et al. |
| 2011/0225105 A1 | 9/2011 | Scholer et al. |
| 2011/0230713 A1 | 9/2011 | Kleemann et al. |
| 2011/0235168 A1 | 9/2011 | Sander |
| 2011/0238044 A1 | 9/2011 | Main et al. |
| 2011/0241597 A1 | 10/2011 | Zhu et al. |
| 2011/0251606 A1 | 10/2011 | Kerr |
| 2011/0256266 A1 | 10/2011 | Orme et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278035 A1 | 11/2011 | Chen |
| 2011/0278343 A1 | 11/2011 | Knodel et al. |
| 2011/0279268 A1 | 11/2011 | Konishi et al. |
| 2011/0285507 A1 | 11/2011 | Nelson |
| 2011/0290856 A1 | 12/2011 | Shelton, IV et al. |
| 2011/0290858 A1 | 12/2011 | Whitman et al. |
| 2011/0292258 A1 | 12/2011 | Adler et al. |
| 2011/0293690 A1 | 12/2011 | Griffin et al. |
| 2011/0295295 A1 | 12/2011 | Shelton, IV et al. |
| 2011/0295299 A1 | 12/2011 | Braithwaite et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0008880 A1 | 1/2012 | Toth |
| 2012/0010615 A1 | 1/2012 | Cummings et al. |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0029550 A1 | 2/2012 | Forsell |
| 2012/0033360 A1 | 2/2012 | Hsu |
| 2012/0043100 A1 | 2/2012 | Isobe et al. |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080491 A1 | 4/2012 | Shelton, IV et al. |
| 2012/0080498 A1 | 4/2012 | Shelton, IV et al. |
| 2012/0083836 A1 | 4/2012 | Shelton, IV et al. |
| 2012/0086276 A1 | 4/2012 | Sawyers |
| 2012/0095458 A1 | 4/2012 | Cybulski et al. |
| 2012/0101488 A1 | 4/2012 | Aldridge et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116263 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0132663 A1 | 5/2012 | Kasvikis et al. |
| 2012/0143173 A1 | 6/2012 | Steege et al. |
| 2012/0143175 A1 | 6/2012 | Hermann et al. |
| 2012/0171539 A1 | 7/2012 | Rejman et al. |
| 2012/0175398 A1 | 7/2012 | Sandborn et al. |
| 2012/0190964 A1 | 7/2012 | Hyde et al. |
| 2012/0197239 A1 | 8/2012 | Smith et al. |
| 2012/0197272 A1 | 8/2012 | Oray et al. |
| 2012/0203213 A1 | 8/2012 | Kimball et al. |
| 2012/0211542 A1 | 8/2012 | Racenet |
| 2012/0220990 A1 | 8/2012 | Mckenzie et al. |

(56) References Cited

U.S. PATENT DOCUMENTS

| | | |
|---|---|---|
| 2012/0233298 A1 | 9/2012 | Verbandt et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0241494 A1 | 9/2012 | Marczyk |
| 2012/0241503 A1 | 9/2012 | Baxter, III et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0256494 A1 | 10/2012 | Kesler et al. |
| 2012/0271327 A1 | 10/2012 | West et al. |
| 2012/0283707 A1 | 11/2012 | Giordano et al. |
| 2012/0286019 A1 | 11/2012 | Hueil et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0296316 A1 | 11/2012 | Imuta |
| 2012/0296342 A1 | 11/2012 | Haglund Wendelschafer |
| 2012/0298722 A1 | 11/2012 | Hess et al. |
| 2012/0301498 A1 | 11/2012 | Altreuter et al. |
| 2012/0310254 A1 | 12/2012 | Manzo et al. |
| 2012/0312861 A1 | 12/2012 | Gurumurthy et al. |
| 2012/0316424 A1 | 12/2012 | Stopek |
| 2012/0330285 A1 | 12/2012 | Hartoumbekis et al. |
| 2012/0330329 A1 | 12/2012 | Harris et al. |
| 2013/0006227 A1 | 1/2013 | Takashino |
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0023915 A1 | 1/2013 | Mueller |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0056522 A1 | 3/2013 | Swensgard |
| 2013/0057162 A1 | 3/2013 | Pollischansky |
| 2013/0068816 A1 | 3/2013 | Mandakolathur Vasudevan et al. |
| 2013/0069088 A1 | 3/2013 | Speck et al. |
| 2013/0075447 A1 | 3/2013 | Weisenburgh, II et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098968 A1 | 4/2013 | Aranyi et al. |
| 2013/0098970 A1 | 4/2013 | Racenet et al. |
| 2013/0106352 A1 | 5/2013 | Nagamine |
| 2013/0112729 A1 | 5/2013 | Beardsley et al. |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153639 A1 | 6/2013 | Hodgkinson et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0165908 A1 | 6/2013 | Purdy et al. |
| 2013/0169217 A1 | 7/2013 | Watanabe et al. |
| 2013/0172713 A1 | 7/2013 | Kirschenman |
| 2013/0172878 A1 | 7/2013 | Smith |
| 2013/0175315 A1 | 7/2013 | Milliman |
| 2013/0175317 A1 | 7/2013 | Yates et al. |
| 2013/0183769 A1 | 7/2013 | Tajima |
| 2013/0186936 A1 | 7/2013 | Shelton, IV |
| 2013/0211244 A1 | 8/2013 | Nathaniel |
| 2013/0214025 A1 | 8/2013 | Zemlok et al. |
| 2013/0215449 A1 | 8/2013 | Yamasaki |
| 2013/0231681 A1 | 9/2013 | Robinson et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0253499 A1 | 9/2013 | Kimball et al. |
| 2013/0256373 A1 | 10/2013 | Schmid et al. |
| 2013/0256380 A1 | 10/2013 | Schmid et al. |
| 2013/0267950 A1 | 10/2013 | Rosa et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0284792 A1 | 10/2013 | Ma |
| 2013/0289565 A1 | 10/2013 | Hassler, Jr. |
| 2013/0293353 A1 | 11/2013 | McPherson et al. |
| 2013/0303845 A1 | 11/2013 | Skula et al. |
| 2013/0304084 A1 | 11/2013 | Beira et al. |
| 2013/0306704 A1 | 11/2013 | Balbierz et al. |
| 2013/0310849 A1 | 11/2013 | Malkowski |
| 2013/0327552 A1 | 12/2013 | Lovelass et al. |
| 2013/0331826 A1 | 12/2013 | Steege |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0002322 A1 | 1/2014 | Kanome et al. |
| 2014/0005550 A1 | 1/2014 | Lu et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0008289 A1 | 1/2014 | Williams et al. |
| 2014/0014704 A1 | 1/2014 | Onukuri et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0022283 A1 | 1/2014 | Chan et al. |
| 2014/0039549 A1 | 2/2014 | Belsky et al. |
| 2014/0041191 A1 | 2/2014 | Knodel |
| 2014/0048580 A1 | 2/2014 | Merchant et al. |
| 2014/0069240 A1 | 3/2014 | Dauvin et al. |
| 2014/0078715 A1 | 3/2014 | Pickard et al. |
| 2014/0081176 A1 | 3/2014 | Hassan |
| 2014/0088614 A1 | 3/2014 | Blumenkranz |
| 2014/0088639 A1 | 3/2014 | Bartels et al. |
| 2014/0094681 A1 | 4/2014 | Valentine et al. |
| 2014/0100554 A1 | 4/2014 | Williams |
| 2014/0100558 A1 | 4/2014 | Schmitz et al. |
| 2014/0107697 A1 | 4/2014 | Patani et al. |
| 2014/0110453 A1 | 4/2014 | Wingardner et al. |
| 2014/0115229 A1 | 4/2014 | Kothamasu et al. |
| 2014/0131418 A1 | 5/2014 | Kostrzewski |
| 2014/0131419 A1 | 5/2014 | Bettuchi |
| 2014/0135832 A1 | 5/2014 | Park et al. |
| 2014/0148803 A1 | 5/2014 | Taylor |
| 2014/0151433 A1 | 6/2014 | Shelton, IV et al. |
| 2014/0155916 A1 | 6/2014 | Hodgkinson et al. |
| 2014/0158747 A1 | 6/2014 | Measamer et al. |
| 2014/0166718 A1 | 6/2014 | Swayze et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0183244 A1 | 7/2014 | Duque et al. |
| 2014/0188091 A1 | 7/2014 | Vidal et al. |
| 2014/0188101 A1 | 7/2014 | Bales, Jr. et al. |
| 2014/0188159 A1 | 7/2014 | Steege |
| 2014/0194874 A1 | 7/2014 | Dietz et al. |
| 2014/0207124 A1 | 7/2014 | Aldridge et al. |
| 2014/0209658 A1 | 7/2014 | Skalla et al. |
| 2014/0215242 A1 | 7/2014 | Jung |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |

(56) References Cited

U.S. PATENT DOCUMENTS

| | | |
|---|---|---|
| 2014/0246475 A1 | 9/2014 | Hall et al. |
| 2014/0248167 A1 | 9/2014 | Sugimoto et al. |
| 2014/0249557 A1 | 9/2014 | Koch et al. |
| 2014/0249573 A1 | 9/2014 | Arav |
| 2014/0262408 A1 | 9/2014 | Woodard |
| 2014/0263535 A1 | 9/2014 | Rajani et al. |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276720 A1 | 9/2014 | Parihar et al. |
| 2014/0276730 A1 | 9/2014 | Boudreaux et al. |
| 2014/0276776 A1 | 9/2014 | Parihar et al. |
| 2014/0284371 A1 | 9/2014 | Morgan et al. |
| 2014/0287703 A1 | 9/2014 | Herbsommer et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0358163 A1 | 12/2014 | Farin et al. |
| 2014/0367445 A1 | 12/2014 | Ingmanson et al. |
| 2014/0371764 A1 | 12/2014 | Oyola et al. |
| 2014/0373003 A1 | 12/2014 | Grez et al. |
| 2014/0374130 A1 | 12/2014 | Nakamura et al. |
| 2014/0378950 A1 | 12/2014 | Chiu |
| 2014/0379000 A1 | 12/2014 | Romo et al. |
| 2015/0001272 A1 | 1/2015 | Sniffin et al. |
| 2015/0002089 A1 | 1/2015 | Rejman et al. |
| 2015/0022012 A1 | 1/2015 | Kim et al. |
| 2015/0025549 A1 | 1/2015 | Kilroy et al. |
| 2015/0025571 A1 | 1/2015 | Suzuki et al. |
| 2015/0034697 A1 | 2/2015 | Mastri et al. |
| 2015/0039010 A1 | 2/2015 | Beardsley et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060516 A1 | 3/2015 | Collings et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0067582 A1 | 3/2015 | Donnelly et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076211 A1 | 3/2015 | Irka et al. |
| 2015/0080883 A1 | 3/2015 | Haverkost et al. |
| 2015/0082624 A1 | 3/2015 | Craig et al. |
| 2015/0083781 A1 | 3/2015 | Giordano et al. |
| 2015/0087952 A1 | 3/2015 | Albert et al. |
| 2015/0088127 A1 | 3/2015 | Craig et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |
| 2015/0127021 A1 | 5/2015 | Harris et al. |
| 2015/0133957 A1 | 5/2015 | Kostrzewski |
| 2015/0134077 A1 | 5/2015 | Shelton, IV et al. |
| 2015/0150620 A1 | 6/2015 | Miyamoto et al. |
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0202013 A1 | 7/2015 | Teichtmann et al. |
| 2015/0209045 A1 | 7/2015 | Hodgkinson et al. |
| 2015/0216605 A1 | 8/2015 | Baldwin |
| 2015/0222212 A1 | 8/2015 | Iwata |
| 2015/0223868 A1 | 8/2015 | Brandt et al. |
| 2015/0230697 A1 | 8/2015 | Phee et al. |
| 2015/0230794 A1 | 8/2015 | Wellman et al. |
| 2015/0230861 A1 | 8/2015 | Woloszko et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272606 A1 | 10/2015 | Nobis |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297824 A1 | 10/2015 | Cabiri et al. |
| 2015/0303417 A1 | 10/2015 | Koeder et al. |
| 2015/0305743 A1 | 10/2015 | Casasanta et al. |
| 2015/0313594 A1 | 11/2015 | Shelton, IV et al. |
| 2015/0324317 A1 | 11/2015 | Collins et al. |
| 2015/0352699 A1 | 12/2015 | Sakai et al. |
| 2015/0366585 A1 | 12/2015 | Lemay et al. |
| 2015/0367497 A1 | 12/2015 | Ito et al. |
| 2015/0372265 A1 | 12/2015 | Morisaku et al. |
| 2015/0374372 A1 | 12/2015 | Zergiebel et al. |
| 2015/0374378 A1 | 12/2015 | Giordano et al. |
| 2016/0000437 A1 | 1/2016 | Giordano et al. |
| 2016/0000452 A1 | 1/2016 | Yates et al. |
| 2016/0000453 A1 | 1/2016 | Yates et al. |
| 2016/0029998 A1 | 2/2016 | Brister et al. |
| 2016/0030042 A1 | 2/2016 | Heinrich et al. |
| 2016/0030043 A1 | 2/2016 | Fanelli et al. |
| 2016/0030076 A1 | 2/2016 | Faller et al. |
| 2016/0047423 A1 | 2/2016 | Bodtker |
| 2016/0051316 A1 | 2/2016 | Boudreaux |
| 2016/0066913 A1 | 3/2016 | Swayze et al. |
| 2016/0069449 A1 | 3/2016 | Kanai et al. |
| 2016/0074035 A1 | 3/2016 | Whitman et al. |
| 2016/0074040 A1 | 3/2016 | Widenhouse et al. |
| 2016/0081678 A1 | 3/2016 | Kappel et al. |
| 2016/0082161 A1 | 3/2016 | Zilberman et al. |
| 2016/0089175 A1 | 3/2016 | Hibner et al. |
| 2016/0099601 A1 | 4/2016 | Leabman et al. |
| 2016/0100838 A1 | 4/2016 | Beaupré et al. |
| 2016/0118201 A1 | 4/2016 | Nicholas et al. |
| 2016/0132026 A1 | 5/2016 | Wingardner et al. |
| 2016/0135835 A1 | 5/2016 | Onuma |
| 2016/0135895 A1 | 5/2016 | Faasse et al. |
| 2016/0139666 A1 | 5/2016 | Rubin et al. |
| 2016/0174969 A1 | 6/2016 | Kerr et al. |
| 2016/0174983 A1 | 6/2016 | Shelton, IV et al. |
| 2016/0175021 A1 | 6/2016 | Hassler, Jr. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192927 A1 | 7/2016 | Kostrzewski |
| 2016/0192960 A1 | 7/2016 | Bueno et al. |
| 2016/0199063 A1 | 7/2016 | Mandakolathur Vasudevan et al. |
| 2016/0199956 A1 | 7/2016 | Shelton, IV et al. |
| 2016/0220150 A1 | 8/2016 | Sharonov |
| 2016/0235494 A1 | 8/2016 | Shelton, IV et al. |
| 2016/0242783 A1 | 8/2016 | Shelton, IV et al. |
| 2016/0242855 A1 | 8/2016 | Fichtinger et al. |
| 2016/0249910 A1 | 9/2016 | Shelton, IV et al. |
| 2016/0249922 A1 | 9/2016 | Morgan et al. |
| 2016/0249929 A1 | 9/2016 | Cappola et al. |
| 2016/0256159 A1 | 9/2016 | Pinjala et al. |
| 2016/0256184 A1 | 9/2016 | Shelton, IV et al. |
| 2016/0256221 A1 | 9/2016 | Smith |
| 2016/0256229 A1 | 9/2016 | Morgan et al. |
| 2016/0262745 A1 | 9/2016 | Morgan et al. |
| 2016/0262921 A1 | 9/2016 | Balbierz et al. |
| 2016/0270781 A1 | 9/2016 | Scirica |

(56) References Cited

U.S. PATENT DOCUMENTS

| | | |
|---|---|---|
| 2016/0287265 A1 | 10/2016 | Macdonald et al. |
| 2016/0287279 A1 | 10/2016 | Bovay et al. |
| 2016/0302820 A1 | 10/2016 | Hibner et al. |
| 2016/0310143 A1 | 10/2016 | Bettuchi |
| 2016/0314716 A1 | 10/2016 | Grubbs |
| 2016/0314717 A1 | 10/2016 | Grubbs |
| 2016/0345972 A1 | 12/2016 | Beardsley et al. |
| 2016/0367122 A1 | 12/2016 | Ichimura et al. |
| 2016/0374669 A1 | 12/2016 | Overmyer et al. |
| 2016/0374716 A1 | 12/2016 | Kessler |
| 2017/0000549 A1 | 1/2017 | Gilbert et al. |
| 2017/0007234 A1 | 1/2017 | Chin et al. |
| 2017/0007244 A1 | 1/2017 | Shelton, IV et al. |
| 2017/0007245 A1 | 1/2017 | Shelton, IV et al. |
| 2017/0007347 A1 | 1/2017 | Jaworek et al. |
| 2017/0020616 A1 | 1/2017 | Vale et al. |
| 2017/0035419 A1 | 2/2017 | Decker et al. |
| 2017/0055819 A1 | 3/2017 | Hansen et al. |
| 2017/0055980 A1 | 3/2017 | Vendely et al. |
| 2017/0056008 A1 | 3/2017 | Shelton, IV et al. |
| 2017/0056016 A1 | 3/2017 | Barton et al. |
| 2017/0056018 A1 | 3/2017 | Zeiner et al. |
| 2017/0066054 A1 | 3/2017 | Birky |
| 2017/0079642 A1 | 3/2017 | Overmyer et al. |
| 2017/0086829 A1 | 3/2017 | Vendely et al. |
| 2017/0086830 A1 | 3/2017 | Yates et al. |
| 2017/0086842 A1 | 3/2017 | Shelton, IV et al. |
| 2017/0086930 A1 | 3/2017 | Thompson et al. |
| 2017/0086932 A1 | 3/2017 | Auld et al. |
| 2017/0095252 A1 | 4/2017 | Smith et al. |
| 2017/0095922 A1 | 4/2017 | Licht et al. |
| 2017/0105727 A1 | 4/2017 | Scheib et al. |
| 2017/0105733 A1 | 4/2017 | Scheib et al. |
| 2017/0105786 A1 | 4/2017 | Scheib et al. |
| 2017/0106302 A1 | 4/2017 | Cummings et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0143336 A1 | 5/2017 | Shah et al. |
| 2017/0168187 A1 | 6/2017 | Calderoni et al. |
| 2017/0172382 A1 | 6/2017 | Nir et al. |
| 2017/0172549 A1 | 6/2017 | Smaby et al. |
| 2017/0172662 A1 | 6/2017 | Panescu et al. |
| 2017/0181803 A1 | 6/2017 | Mayer-Ullmann et al. |
| 2017/0182195 A1 | 6/2017 | Wagner |
| 2017/0182211 A1 | 6/2017 | Raxworthy et al. |
| 2017/0196558 A1 | 7/2017 | Morgan et al. |
| 2017/0196649 A1 | 7/2017 | Yates et al. |
| 2017/0202605 A1 | 7/2017 | Shelton, IV et al. |
| 2017/0202607 A1 | 7/2017 | Shelton, IV et al. |
| 2017/0202770 A1 | 7/2017 | Friedrich et al. |
| 2017/0209145 A1 | 7/2017 | Swayze et al. |
| 2017/0224332 A1 | 8/2017 | Hunter et al. |
| 2017/0231628 A1 | 8/2017 | Shelton, IV et al. |
| 2017/0231629 A1 | 8/2017 | Stopek et al. |
| 2017/0238962 A1 | 8/2017 | Hansen et al. |
| 2017/0238991 A1 | 8/2017 | Worrell et al. |
| 2017/0242455 A1 | 8/2017 | Dickens |
| 2017/0245880 A1 | 8/2017 | Honda et al. |
| 2017/0245949 A1 | 8/2017 | Randle |
| 2017/0249431 A1 | 8/2017 | Shelton, IV et al. |
| 2017/0252060 A1 | 9/2017 | Ellingson et al. |
| 2017/0255799 A1 | 9/2017 | Zhao et al. |
| 2017/0258471 A1 | 9/2017 | DiNardo et al. |
| 2017/0262110 A1 | 9/2017 | Polishchuk et al. |
| 2017/0265774 A1 | 9/2017 | Johnson et al. |
| 2017/0281186 A1 | 10/2017 | Shelton, IV et al. |
| 2017/0281189 A1 | 10/2017 | Nalagatla et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0308665 A1 | 10/2017 | Heck et al. |
| 2017/0312042 A1 | 11/2017 | Giordano et al. |
| 2017/0319047 A1 | 11/2017 | Poulsen et al. |
| 2017/0319201 A1 | 11/2017 | Morgan et al. |
| 2017/0333034 A1 | 11/2017 | Morgan et al. |
| 2017/0333035 A1 | 11/2017 | Morgan et al. |
| 2017/0348010 A1 | 12/2017 | Chiang |
| 2017/0348042 A1 | 12/2017 | Drochner et al. |
| 2017/0348043 A1 | 12/2017 | Wang et al. |
| 2017/0354413 A1 | 12/2017 | Chen et al. |
| 2017/0358052 A1 | 12/2017 | Yuan |
| 2017/0360441 A1 | 12/2017 | Sgroi |
| 2018/0008265 A1 | 1/2018 | Hatanaka et al. |
| 2018/0036024 A1 | 2/2018 | Allen, IV |
| 2018/0036025 A1 | 2/2018 | Drochner et al. |
| 2018/0042610 A1 | 2/2018 | Sgroi, Jr. |
| 2018/0042689 A1 | 2/2018 | Mozdzierz et al. |
| 2018/0049738 A1 | 2/2018 | Meloul et al. |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0067004 A1 | 3/2018 | Sgroi, Jr. |
| 2018/0085116 A1 | 3/2018 | Yates et al. |
| 2018/0085117 A1 | 3/2018 | Shelton, IV et al. |
| 2018/0085120 A1 | 3/2018 | Viola |
| 2018/0092710 A1 | 4/2018 | Bosisio et al. |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125590 A1 | 5/2018 | Giordano et al. |
| 2018/0125594 A1 | 5/2018 | Beardsley |
| 2018/0132845 A1 | 5/2018 | Schmid et al. |
| 2018/0132849 A1 | 5/2018 | Miller et al. |
| 2018/0132850 A1 | 5/2018 | Leimbach et al. |
| 2018/0132926 A1 | 5/2018 | Asher et al. |
| 2018/0132952 A1 | 5/2018 | Spivey et al. |
| 2018/0133521 A1 | 5/2018 | Frushour et al. |
| 2018/0140299 A1 | 5/2018 | Weaner et al. |
| 2018/0146960 A1 | 5/2018 | Shelton, IV et al. |
| 2018/0153542 A1 | 6/2018 | Shelton, IV et al. |
| 2018/0153634 A1 | 6/2018 | Zemlok et al. |
| 2018/0161034 A1 | 6/2018 | Scheib et al. |
| 2018/0168572 A1 | 6/2018 | Burbank |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168592 A1 | 6/2018 | Overmyer et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0168754 A1 | 6/2018 | Overmyer |
| 2018/0168756 A1 | 6/2018 | Liao et al. |
| 2018/0206904 A1 | 7/2018 | Felder et al. |
| 2018/0228490 A1 | 8/2018 | Richard et al. |
| 2018/0231111 A1 | 8/2018 | Mika et al. |
| 2018/0231475 A1 | 8/2018 | Brown et al. |
| 2018/0235609 A1 | 8/2018 | Harris et al. |
| 2018/0235617 A1 | 8/2018 | Shelton, IV et al. |
| 2018/0235618 A1 | 8/2018 | Kostrzewski |
| 2018/0235626 A1 | 8/2018 | Shelton, IV et al. |
| 2018/0236181 A1 | 8/2018 | Marlin et al. |
| 2018/0242970 A1 | 8/2018 | Mozdzierz |
| 2018/0247711 A1 | 8/2018 | Terry |
| 2018/0250002 A1 | 9/2018 | Eschbach |
| 2018/0271520 A1 | 9/2018 | Shelton, IV et al. |
| 2018/0271526 A1 | 9/2018 | Zammataro |
| 2018/0271553 A1 | 9/2018 | Worrell |
| 2018/0271604 A1 | 9/2018 | Grout et al. |

(56) References Cited

U.S. PATENT DOCUMENTS

| | | |
|---|---|---|
| 2018/0273597 A1 | 9/2018 | Stimson |
| 2018/0279994 A1 | 10/2018 | Schaer et al. |
| 2018/0280026 A1 | 10/2018 | Zhang et al. |
| 2018/0280073 A1 | 10/2018 | Sanai et al. |
| 2018/0289371 A1 | 10/2018 | Wang et al. |
| 2018/0296216 A1 | 10/2018 | Shelton, IV et al. |
| 2018/0296290 A1 | 10/2018 | Namiki et al. |
| 2018/0310995 A1 | 11/2018 | Gliner et al. |
| 2018/0317905 A1 | 11/2018 | Olson et al. |
| 2018/0317915 A1 | 11/2018 | McDonald, II |
| 2018/0325514 A1 | 11/2018 | Harris et al. |
| 2018/0333169 A1 | 11/2018 | Leimbach et al. |
| 2018/0360446 A1 | 12/2018 | Shelton, IV et al. |
| 2018/0360456 A1 | 12/2018 | Shelton, IV et al. |
| 2018/0360472 A1 | 12/2018 | Harris et al. |
| 2018/0360473 A1 | 12/2018 | Shelton, IV et al. |
| 2018/0368066 A1 | 12/2018 | Howell et al. |
| 2018/0368833 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0372806 A1 | 12/2018 | Laughery et al. |
| 2018/0375165 A1 | 12/2018 | Shelton, IV et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000470 A1 | 1/2019 | Yates et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000481 A1 | 1/2019 | Harris et al. |
| 2019/0000535 A1 | 1/2019 | Messerly et al. |
| 2019/0000536 A1 | 1/2019 | Yates et al. |
| 2019/0006047 A1 | 1/2019 | Gorek et al. |
| 2019/0008515 A1 | 1/2019 | Beardsley et al. |
| 2019/0015102 A1 | 1/2019 | Baber et al. |
| 2019/0015165 A1 | 1/2019 | Giordano et al. |
| 2019/0017311 A1 | 1/2019 | McGettrick et al. |
| 2019/0021733 A1 | 1/2019 | Burbank |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038285 A1 | 2/2019 | Mozdzierz |
| 2019/0059984 A1 | 2/2019 | Otrembiak et al. |
| 2019/0059986 A1 | 2/2019 | Shelton, IV et al. |
| 2019/0076143 A1 | 3/2019 | Smith |
| 2019/0090871 A1 | 3/2019 | Shelton, IV et al. |
| 2019/0091183 A1 | 3/2019 | Tomat et al. |
| 2019/0099179 A1 | 4/2019 | Leimbach et al. |
| 2019/0099181 A1 | 4/2019 | Shelton, IV et al. |
| 2019/0099229 A1 | 4/2019 | Spivey et al. |
| 2019/0104919 A1 | 4/2019 | Shelton, IV et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0110779 A1 | 4/2019 | Gardner et al. |
| 2019/0110791 A1 | 4/2019 | Shelton, IV et al. |
| 2019/0110792 A1 | 4/2019 | Shelton, IV et al. |
| 2019/0117220 A1 | 4/2019 | Nativ et al. |
| 2019/0117224 A1 | 4/2019 | Setser et al. |
| 2019/0117287 A1 | 4/2019 | Nativ et al. |
| 2019/0122840 A1 | 4/2019 | Zergiebel et al. |
| 2019/0125320 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125342 A1 | 5/2019 | Beardsley et al. |
| 2019/0125344 A1 | 5/2019 | DiNardo et al. |
| 2019/0125357 A1 | 5/2019 | Shelton, IV et al. |
| 2019/0125358 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125387 A1 | 5/2019 | Parihar et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133422 A1 | 5/2019 | Nakamura |
| 2019/0133577 A1 | 5/2019 | Weadock et al. |
| 2019/0138770 A1 | 5/2019 | Compaijen et al. |
| 2019/0142421 A1 | 5/2019 | Shelton, IV |
| 2019/0142423 A1 | 5/2019 | Satti, III et al. |
| 2019/0150925 A1 | 5/2019 | Marczyk et al. |
| 2019/0151029 A1 | 5/2019 | Robinson |
| 2019/0159778 A1 | 5/2019 | Shelton, IV et al. |
| 2019/0175847 A1 | 6/2019 | Pocreva, III et al. |
| 2019/0183502 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192156 A1 | 6/2019 | Simms et al. |
| 2019/0192157 A1 | 6/2019 | Scott et al. |
| 2019/0192235 A1 | 6/2019 | Harris et al. |
| 2019/0192236 A1 | 6/2019 | Shelton, IV et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200989 A1 | 7/2019 | Burbank et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201079 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |

(56) References Cited

U.S. PATENT DOCUMENTS

| | | |
|---|---|---|
| 2019/0201158 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206003 A1 | 7/2019 | Harris et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0239873 A1 | 8/2019 | Laurent et al. |
| 2019/0247048 A1 | 8/2019 | Gasparovich et al. |
| 2019/0261982 A1 | 8/2019 | Holsten |
| 2019/0261983 A1 | 8/2019 | Granger et al. |
| 2019/0261984 A1 | 8/2019 | Nelson et al. |
| 2019/0261987 A1 | 8/2019 | Viola et al. |
| 2019/0262153 A1 | 8/2019 | Tassoni et al. |
| 2019/0269400 A1 | 9/2019 | Mandakolathur Vasudevan et al. |
| 2019/0269402 A1 | 9/2019 | Murray et al. |
| 2019/0269407 A1 | 9/2019 | Swensgard et al. |
| 2019/0269428 A1 | 9/2019 | Allen et al. |
| 2019/0274677 A1 | 9/2019 | Shelton, IV |
| 2019/0274685 A1 | 9/2019 | Olson et al. |
| 2019/0274716 A1 | 9/2019 | Nott et al. |
| 2019/0282233 A1 | 9/2019 | Burbank et al. |
| 2019/0290264 A1 | 9/2019 | Morgan et al. |
| 2019/0290266 A1 | 9/2019 | Scheib et al. |
| 2019/0290267 A1 | 9/2019 | Baxter, III et al. |
| 2019/0290297 A1 | 9/2019 | Haider et al. |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0298381 A1 | 10/2019 | Kreidler et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307456 A1 | 10/2019 | Shelton, IV et al. |
| 2019/0307479 A1 | 10/2019 | Shelton, IV et al. |
| 2019/0314015 A1 | 10/2019 | Shelton, IV et al. |
| 2019/0314017 A1 | 10/2019 | Huitema et al. |
| 2019/0314018 A1 | 10/2019 | Huitema et al. |
| 2019/0321040 A1 | 10/2019 | Shelton, IV |
| 2019/0321062 A1 | 10/2019 | Williams |
| 2019/0328387 A1 | 10/2019 | Overmyer et al. |
| 2019/0328390 A1 | 10/2019 | Harris et al. |
| 2019/0343515 A1 | 11/2019 | Morgan et al. |
| 2019/0343525 A1 | 11/2019 | Shelton, IV et al. |
| 2019/0350581 A1 | 11/2019 | Baxter, III et al. |
| 2019/0350582 A1 | 11/2019 | Shelton, IV et al. |
| 2019/0357909 A1 | 11/2019 | Huitema et al. |
| 2019/0365384 A1 | 12/2019 | Baxter, III et al. |
| 2019/0374224 A1 | 12/2019 | Huitema et al. |
| 2019/0388091 A1 | 12/2019 | Eschbach et al. |
| 2020/0000471 A1 | 1/2020 | Shelton, IV et al. |
| 2020/0000531 A1 | 1/2020 | Giordano et al. |
| 2020/0008800 A1 | 1/2020 | Shelton, IV et al. |
| 2020/0008802 A1 | 1/2020 | Aronhalt et al. |
| 2020/0008809 A1 | 1/2020 | Shelton, IV et al. |
| 2020/0008827 A1 | 1/2020 | Dearden et al. |
| 2020/0015817 A1 | 1/2020 | Harris et al. |
| 2020/0015819 A1 | 1/2020 | Shelton, IV et al. |
| 2020/0015836 A1 | 1/2020 | Nicholas et al. |
| 2020/0015915 A1 | 1/2020 | Swayze et al. |
| 2020/0030020 A1 | 1/2020 | Wang et al. |
| 2020/0037939 A1 | 2/2020 | Castagna et al. |
| 2020/0038016 A1 | 2/2020 | Shelton, IV et al. |
| 2020/0038018 A1 | 2/2020 | Shelton, IV et al. |
| 2020/0038020 A1 | 2/2020 | Yates et al. |
| 2020/0038021 A1 | 2/2020 | Contini et al. |
| 2020/0046348 A1 | 2/2020 | Shelton, IV et al. |
| 2020/0046355 A1 | 2/2020 | Harris et al. |
| 2020/0046356 A1 | 2/2020 | Baxter, III et al. |
| 2020/0054320 A1 | 2/2020 | Harris et al. |
| 2020/0054321 A1 | 2/2020 | Harris et al. |
| 2020/0054324 A1 | 2/2020 | Shelton, IV et al. |
| 2020/0054329 A1 | 2/2020 | Shelton, IV et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060523 A1 | 2/2020 | Matsuda et al. |
| 2020/0060680 A1 | 2/2020 | Shelton, IV et al. |
| 2020/0060713 A1 | 2/2020 | Leimbach et al. |
| 2020/0061385 A1 | 2/2020 | Schwarz et al. |
| 2020/0077994 A1 | 3/2020 | Shelton, IV et al. |
| 2020/0078015 A1 | 3/2020 | Miller et al. |
| 2020/0085427 A1 | 3/2020 | Giordano et al. |
| 2020/0085431 A1 | 3/2020 | Swayze et al. |
| 2020/0085435 A1 | 3/2020 | Shelton, IV et al. |
| 2020/0085436 A1 | 3/2020 | Beckman et al. |
| 2020/0085518 A1 | 3/2020 | Giordano et al. |
| 2020/0093484 A1 | 3/2020 | Shelton, IV et al. |
| 2020/0093485 A1 | 3/2020 | Shelton, IV et al. |
| 2020/0093506 A1 | 3/2020 | Leimbach et al. |
| 2020/0093550 A1 | 3/2020 | Spivey et al. |
| 2020/0100699 A1 | 4/2020 | Shelton, IV et al. |
| 2020/0100783 A1 | 4/2020 | Yates et al. |
| 2020/0107829 A1 | 4/2020 | Shelton, IV et al. |
| 2020/0113563 A1 | 4/2020 | Gupta et al. |
| 2020/0114505 A1 | 4/2020 | Kikuchi |
| 2020/0138434 A1 | 5/2020 | Miller et al. |
| 2020/0138435 A1 | 5/2020 | Shelton, IV et al. |
| 2020/0138436 A1 | 5/2020 | Yates et al. |
| 2020/0138507 A1 | 5/2020 | Davison et al. |
| 2020/0138534 A1 | 5/2020 | Garcia Kilroy et al. |
| 2020/0146166 A1 | 5/2020 | Sgroi, Jr. |
| 2020/0146676 A1 | 5/2020 | Yates et al. |
| 2020/0146741 A1 | 5/2020 | Long et al. |
| 2020/0187943 A1 | 6/2020 | Shelton, IV et al. |
| 2020/0197027 A1 | 6/2020 | Hershberger et al. |
| 2020/0205810 A1 | 7/2020 | Posey et al. |
| 2020/0205811 A1 | 7/2020 | Posey et al. |
| 2020/0205823 A1 | 7/2020 | Vendely et al. |
| 2020/0214706 A1 | 7/2020 | Vendely et al. |
| 2020/0214731 A1 | 7/2020 | Shelton, IV et al. |
| 2020/0222047 A1 | 7/2020 | Shelton, IV et al. |
| 2020/0229812 A1 | 7/2020 | Parihar et al. |
| 2020/0229814 A1 | 7/2020 | Amariglio et al. |
| 2020/0229816 A1 | 7/2020 | Bakos et al. |
| 2020/0237371 A1 | 7/2020 | Huitema et al. |
| 2020/0246001 A1 | 8/2020 | Ming et al. |
| 2020/0253605 A1 | 8/2020 | Swayze et al. |
| 2020/0261075 A1 | 8/2020 | Boudreaux et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0261106 A1 | 8/2020 | Hess et al. |
| 2020/0268377 A1 | 8/2020 | Schmid et al. |
| 2020/0268381 A1 | 8/2020 | Roberts et al. |
| 2020/0275926 A1 | 9/2020 | Shelton, IV et al. |
| 2020/0275927 A1 | 9/2020 | Shelton, IV et al. |
| 2020/0275928 A1 | 9/2020 | Shelton, IV et al. |

(56) References Cited

U.S. PATENT DOCUMENTS

| | | |
|---|---|---|
| 2020/0275930 A1 | 9/2020 | Harris et al. |
| 2020/0280219 A1 | 9/2020 | Laughery et al. |
| 2020/0281585 A1 | 9/2020 | Timm et al. |
| 2020/0281587 A1 | 9/2020 | Schmid et al. |
| 2020/0281590 A1 | 9/2020 | Shelton, IV et al. |
| 2020/0289112 A1 | 9/2020 | Whitfield et al. |
| 2020/0289119 A1 | 9/2020 | Viola et al. |
| 2020/0297340 A1 | 9/2020 | Hess et al. |
| 2020/0297341 A1 | 9/2020 | Yates et al. |
| 2020/0297346 A1 | 9/2020 | Shelton, IV et al. |
| 2020/0297438 A1 | 9/2020 | Shelton, IV et al. |
| 2020/0305862 A1 | 10/2020 | Yates et al. |
| 2020/0305863 A1 | 10/2020 | Yates et al. |
| 2020/0305864 A1 | 10/2020 | Yates et al. |
| 2020/0305870 A1 | 10/2020 | Shelton, IV |
| 2020/0305871 A1 | 10/2020 | Shelton, IV et al. |
| 2020/0305872 A1 | 10/2020 | Weidner et al. |
| 2020/0305874 A1 | 10/2020 | Huitema et al. |
| 2020/0315612 A1 | 10/2020 | Shelton, IV et al. |
| 2020/0315623 A1 | 10/2020 | Eisinger et al. |
| 2020/0315625 A1 | 10/2020 | Hall et al. |
| 2020/0315983 A1 | 10/2020 | Widenhouse et al. |
| 2020/0323526 A1 | 10/2020 | Huang et al. |
| 2020/0330092 A1 | 10/2020 | Shelton, IV et al. |
| 2020/0330093 A1 | 10/2020 | Shelton, IV et al. |
| 2020/0330094 A1 | 10/2020 | Baxter, III et al. |
| 2020/0330096 A1 | 10/2020 | Shelton, IV et al. |
| 2020/0330181 A1 | 10/2020 | Junger et al. |
| 2020/0337693 A1 | 10/2020 | Shelton, IV et al. |
| 2020/0337702 A1 | 10/2020 | Shelton, IV et al. |
| 2020/0337703 A1 | 10/2020 | Shelton, IV et al. |
| 2020/0337706 A1 | 10/2020 | Truckai et al. |
| 2020/0337791 A1 | 10/2020 | Shelton, IV et al. |
| 2020/0345346 A1 | 11/2020 | Shelton, IV et al. |
| 2020/0345349 A1 | 11/2020 | Kimball et al. |
| 2020/0345352 A1 | 11/2020 | Shelton, IV et al. |
| 2020/0345353 A1 | 11/2020 | Leimbach et al. |
| 2020/0345354 A1 | 11/2020 | Leimbach et al. |
| 2020/0345355 A1 | 11/2020 | Baxter, III et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345360 A1 | 11/2020 | Leimbach et al. |
| 2020/0345363 A1 | 11/2020 | Shelton, IV et al. |
| 2020/0345435 A1 | 11/2020 | Traina |
| 2020/0345446 A1 | 11/2020 | Kimball et al. |
| 2020/0352562 A1 | 11/2020 | Timm et al. |
| 2020/0367885 A1 | 11/2020 | Yates et al. |
| 2020/0367886 A1 | 11/2020 | Shelton, IV et al. |
| 2020/0375585 A1 | 12/2020 | Swayze et al. |
| 2020/0375592 A1 | 12/2020 | Hall et al. |
| 2020/0375593 A1 | 12/2020 | Hunter et al. |
| 2020/0375597 A1 | 12/2020 | Shelton, IV et al. |
| 2020/0390444 A1 | 12/2020 | Harris et al. |
| 2020/0397430 A1 | 12/2020 | Patel et al. |
| 2020/0397433 A1 | 12/2020 | Lytle, IV et al. |
| 2020/0397434 A1 | 12/2020 | Overmyer et al. |
| 2020/0397439 A1 | 12/2020 | Eisinger |
| 2020/0405290 A1 | 12/2020 | Shelton, IV et al. |
| 2020/0405292 A1 | 12/2020 | Shelton, IV et al. |
| 2020/0405293 A1 | 12/2020 | Shelton, IV et al. |
| 2020/0405294 A1 | 12/2020 | Shelton, IV |
| 2020/0405295 A1 | 12/2020 | Shelton, IV et al. |
| 2020/0405296 A1 | 12/2020 | Shelton, IV et al. |
| 2020/0405302 A1 | 12/2020 | Shelton, IV et al. |
| 2020/0405303 A1 | 12/2020 | Shelton, IV |
| 2020/0405304 A1 | 12/2020 | Mozdzierz et al. |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405309 A1 | 12/2020 | Shelton, IV et al. |
| 2020/0405312 A1 | 12/2020 | Shelton, IV et al. |
| 2020/0405313 A1 | 12/2020 | Shelton, IV |
| 2020/0405314 A1 | 12/2020 | Shelton, IV et al. |
| 2020/0405316 A1 | 12/2020 | Shelton, IV et al. |
| 2020/0405341 A1 | 12/2020 | Hess et al. |
| 2020/0405375 A1 | 12/2020 | Shelton, IV et al. |
| 2020/0405403 A1 | 12/2020 | Shelton, IV et al. |
| 2020/0405409 A1 | 12/2020 | Shelton, IV et al. |
| 2020/0405410 A1 | 12/2020 | Shelton, IV |
| 2020/0405416 A1 | 12/2020 | Shelton, IV et al. |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0410177 A1 | 12/2020 | Shelton, IV |
| 2020/0410180 A1 | 12/2020 | Shelton, IV et al. |
| 2021/0000466 A1 | 1/2021 | Leimbach et al. |
| 2021/0000470 A1 | 1/2021 | Leimbach et al. |
| 2021/0007742 A1 | 1/2021 | Rector et al. |
| 2021/0015480 A1 | 1/2021 | Shelton, IV et al. |
| 2021/0022741 A1 | 1/2021 | Baxter, III et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059666 A1 | 3/2021 | Schmid et al. |
| 2021/0059669 A1 | 3/2021 | Yates et al. |
| 2021/0059670 A1 | 3/2021 | Overmyer et al. |
| 2021/0059671 A1 | 3/2021 | Shelton, IV et al. |
| 2021/0059672 A1 | 3/2021 | Giordano et al. |
| 2021/0059673 A1 | 3/2021 | Shelton, IV et al. |
| 2021/0068817 A1 | 3/2021 | Shelton, IV et al. |
| 2021/0068818 A1 | 3/2021 | Overmyer et al. |
| 2021/0068820 A1 | 3/2021 | Parihar et al. |
| 2021/0068829 A1 | 3/2021 | Miller et al. |
| 2021/0068830 A1 | 3/2021 | Baber et al. |
| 2021/0068831 A1 | 3/2021 | Baber et al. |
| 2021/0068832 A1 | 3/2021 | Yates et al. |
| 2021/0068835 A1 | 3/2021 | Shelton, IV et al. |
| 2021/0077092 A1 | 3/2021 | Parihar et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0084700 A1 | 3/2021 | Daniels |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085317 A1 | 3/2021 | Miller et al. |
| 2021/0085318 A1 | 3/2021 | Swayze et al. |
| 2021/0085319 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0085326 A1 | 3/2021 | Vendely et al. |
| 2021/0093321 A1 | 4/2021 | Auld et al. |
| 2021/0093323 A1 | 4/2021 | Scirica et al. |
| 2021/0100541 A1 | 4/2021 | Shelton, IV et al. |
| 2021/0100550 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0128153 A1 | 5/2021 | Sgroi |
| 2021/0137522 A1 | 5/2021 | Shelton, IV et al. |
| 2021/0153866 A1 | 5/2021 | Knapp et al. |
| 2021/0177401 A1 | 6/2021 | Abramek et al. |
| 2021/0177411 A1 | 6/2021 | Williams |
| 2021/0177528 A1 | 6/2021 | Cappelleri et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |

(56) References Cited

U.S. PATENT DOCUMENTS

| | | |
|---|---|---|
| 2021/0186503 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186506 A1 | 6/2021 | Shelton, IV et al. |
| 2021/0186507 A1 | 6/2021 | Shelton, IV et al. |
| 2021/0196265 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0204941 A1 | 7/2021 | Dewaele et al. |
| 2021/0204951 A1 | 7/2021 | Sgroi et al. |
| 2021/0212671 A1 | 7/2021 | Ramadan et al. |
| 2021/0212691 A1 | 7/2021 | Smith et al. |
| 2021/0212776 A1 | 7/2021 | Schmitt et al. |
| 2021/0219976 A1 | 7/2021 | DiNardo et al. |
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244411 A1 | 8/2021 | Smith et al. |
| 2021/0244412 A1 | 8/2021 | Vendely et al. |
| 2021/0251720 A1 | 8/2021 | Jhaveri et al. |
| 2021/0259681 A1 | 8/2021 | Shelton, IV et al. |
| 2021/0259687 A1 | 8/2021 | Gonzalez et al. |
| 2021/0259790 A1 | 8/2021 | Kaiser |
| 2021/0259986 A1 | 8/2021 | Widenhouse et al. |
| 2021/0259987 A1 | 8/2021 | Widenhouse et al. |
| 2021/0267589 A1 | 9/2021 | Swayze et al. |
| 2021/0267592 A1 | 9/2021 | Baxter, III et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275175 A1 | 9/2021 | Vadali et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282774 A1 | 9/2021 | Shelton, IV et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0290322 A1 | 9/2021 | Traina |
| 2021/0298745 A1 | 9/2021 | Leimbach et al. |
| 2021/0298746 A1 | 9/2021 | Leimbach et al. |
| 2021/0307744 A1 | 10/2021 | Walcott et al. |
| 2021/0307748 A1 | 10/2021 | Harris et al. |
| 2021/0307754 A1 | 10/2021 | Shelton, IV et al. |
| 2021/0313975 A1 | 10/2021 | Shan et al. |
| 2021/0315566 A1 | 10/2021 | Yates et al. |
| 2021/0315570 A1 | 10/2021 | Shelton, IV |
| 2021/0315571 A1 | 10/2021 | Swayze et al. |
| 2021/0315573 A1 | 10/2021 | Shelton, IV et al. |
| 2021/0315574 A1 | 10/2021 | Shelton, IV et al. |
| 2021/0315576 A1 | 10/2021 | Shelton, IV et al. |
| 2021/0315577 A1 | 10/2021 | Shelton, IV et al. |
| 2021/0322009 A1 | 10/2021 | Huang et al. |
| 2021/0330321 A1 | 10/2021 | Leimbach et al. |
| 2021/0338233 A1 | 11/2021 | Shelton, IV et al. |
| 2021/0338234 A1 | 11/2021 | Shelton, IV et al. |
| 2021/0338260 A1 | 11/2021 | Le Rolland et al. |
| 2021/0346082 A1 | 11/2021 | Adams et al. |
| 2021/0353284 A1 | 11/2021 | Yang et al. |
| 2021/0369271 A1 | 12/2021 | Schings et al. |
| 2021/0369273 A1 | 12/2021 | Yates et al. |
| 2021/0378669 A1 | 12/2021 | Shelton, IV et al. |
| 2021/0393260 A1 | 12/2021 | Shelton, IV et al. |
| 2021/0393261 A1 | 12/2021 | Harris et al. |
| 2021/0393262 A1 | 12/2021 | Shelton, IV et al. |
| 2021/0393268 A1 | 12/2021 | Shelton, IV et al. |
| 2021/0393366 A1 | 12/2021 | Shelton, IV et al. |
| 2021/0401487 A1 | 12/2021 | Apostolopoulos et al. |
| 2021/0401513 A1 | 12/2021 | Apostolopoulos et al. |
| 2022/0000478 A1 | 1/2022 | Shelton, IV et al. |
| 2022/0000479 A1 | 1/2022 | Shelton, IV et al. |
| 2022/0015760 A1 | 1/2022 | Beardsley et al. |
| 2022/0031313 A1 | 2/2022 | Bakos et al. |
| 2022/0031314 A1 | 2/2022 | Bakos et al. |
| 2022/0031315 A1 | 2/2022 | Bakos et al. |
| 2022/0031319 A1 | 2/2022 | Witte et al. |
| 2022/0031320 A1 | 2/2022 | Hall et al. |
| 2022/0031322 A1 | 2/2022 | Parks |
| 2022/0031323 A1 | 2/2022 | Witte |
| 2022/0031324 A1 | 2/2022 | Hall et al. |
| 2022/0031345 A1 | 2/2022 | Witte |
| 2022/0031346 A1 | 2/2022 | Parks |
| 2022/0031350 A1 | 2/2022 | Witte |
| 2022/0031351 A1 | 2/2022 | Moubarak et al. |
| 2022/0049593 A1 | 2/2022 | Groover et al. |
| 2022/0054125 A1 | 2/2022 | Ji et al. |
| 2022/0054130 A1 | 2/2022 | Overmyer et al. |
| 2022/0061642 A1 | 3/2022 | Park et al. |
| 2022/0061836 A1 | 3/2022 | Parihar et al. |
| 2022/0061843 A1 | 3/2022 | Vendely et al. |
| 2022/0061845 A1 | 3/2022 | Shelton, IV et al. |
| 2022/0061862 A1 | 3/2022 | Shelton, IV et al. |
| 2022/0071630 A1 | 3/2022 | Swayze et al. |
| 2022/0071631 A1 | 3/2022 | Harris et al. |
| 2022/0071632 A1 | 3/2022 | Patel et al. |
| 2022/0071635 A1 | 3/2022 | Shelton, IV et al. |
| 2022/0079580 A1 | 3/2022 | Vendely et al. |
| 2022/0079586 A1 | 3/2022 | Shelton, IV et al. |
| 2022/0079588 A1 | 3/2022 | Harris et al. |
| 2022/0079589 A1 | 3/2022 | Harris et al. |
| 2022/0079590 A1 | 3/2022 | Harris et al. |
| 2022/0079595 A1 | 3/2022 | Huitema et al. |
| 2022/0079596 A1 | 3/2022 | Huitema et al. |
| 2022/0087676 A1 | 3/2022 | Shelton, IV et al. |
| 2022/0104695 A1 | 4/2022 | Russell |
| 2022/0104814 A1 | 4/2022 | Shelton, IV et al. |
| 2022/0104816 A1 | 4/2022 | Fernandes et al. |
| 2022/0104820 A1 | 4/2022 | Shelton, IV et al. |
| 2022/0110673 A1 | 4/2022 | Boronyak et al. |
| 2022/0117602 A1 | 4/2022 | Wise et al. |
| 2022/0125472 A1 | 4/2022 | Beckman et al. |
| 2022/0133299 A1 | 5/2022 | Baxter, III |
| 2022/0133300 A1 | 5/2022 | Leimbach et al. |
| 2022/0133301 A1 | 5/2022 | Leimbach |
| 2022/0133302 A1 | 5/2022 | Zerkle et al. |
| 2022/0133303 A1 | 5/2022 | Huang |
| 2022/0133304 A1 | 5/2022 | Leimbach et al. |
| 2022/0133310 A1 | 5/2022 | Ross |
| 2022/0133311 A1 | 5/2022 | Huang |
| 2022/0133312 A1 | 5/2022 | Huang |
| 2022/0133318 A1 | 5/2022 | Hudson et al. |
| 2022/0133427 A1 | 5/2022 | Baxter, III |
| 2022/0133428 A1 | 5/2022 | Leimbach et al. |
| 2022/0142643 A1 | 5/2022 | Shelton, IV et al. |
| 2022/0151611 A1 | 5/2022 | Shelton, IV et al. |
| 2022/0151613 A1 | 5/2022 | Vendely et al. |
| 2022/0151614 A1 | 5/2022 | Vendely et al. |
| 2022/0151615 A1 | 5/2022 | Shelton, IV et al. |
| 2022/0151616 A1 | 5/2022 | Shelton, IV et al. |
| 2022/0160355 A1 | 5/2022 | Harris et al. |
| 2022/0160358 A1 | 5/2022 | Wixey |
| 2022/0167968 A1 | 6/2022 | Worthington et al. |
| 2022/0167970 A1 | 6/2022 | Aronhalt et al. |
| 2022/0167971 A1 | 6/2022 | Shelton, IV et al. |
| 2022/0167972 A1 | 6/2022 | Shelton, IV et al. |
| 2022/0167973 A1 | 6/2022 | Shelton, IV et al. |
| 2022/0167974 A1 | 6/2022 | Shelton, IV et al. |
| 2022/0167975 A1 | 6/2022 | Shelton, IV et al. |
| 2022/0167977 A1 | 6/2022 | Shelton, IV et al. |
| 2022/0167979 A1 | 6/2022 | Yates et al. |
| 2022/0167980 A1 | 6/2022 | Shelton, IV et al. |
| 2022/0167981 A1 | 6/2022 | Shelton, IV et al. |
| 2022/0167982 A1 | 6/2022 | Shelton, IV et al. |
| 2022/0167983 A1 | 6/2022 | Shelton, IV et al. |
| 2022/0167984 A1 | 6/2022 | Shelton, IV et al. |

(56) References Cited

U.S. PATENT DOCUMENTS

| | | |
|---|---|---|
| 2022/0167995 A1 | 6/2022 | Parfett et al. |
| 2022/0168038 A1 | 6/2022 | Shelton, IV et al. |
| 2022/0175370 A1 | 6/2022 | Shelton, IV et al. |
| 2022/0175371 A1 | 6/2022 | Hess et al. |
| 2022/0175372 A1 | 6/2022 | Shelton, IV et al. |
| 2022/0175375 A1 | 6/2022 | Harris et al. |
| 2022/0175378 A1 | 6/2022 | Leimbach et al. |
| 2022/0175381 A1 | 6/2022 | Scheib et al. |
| 2022/0183685 A1 | 6/2022 | Shelton, IV et al. |
| 2022/0202487 A1 | 6/2022 | Shelton, IV et al. |
| 2022/0211367 A1 | 7/2022 | Schmid et al. |
| 2022/0218332 A1 | 7/2022 | Shelton, IV et al. |
| 2022/0218333 A1 | 7/2022 | Parihar et al. |
| 2022/0218334 A1 | 7/2022 | Parihar et al. |
| 2022/0218336 A1 | 7/2022 | Timm et al. |
| 2022/0218337 A1 | 7/2022 | Timm et al. |
| 2022/0218338 A1 | 7/2022 | Shelton, IV et al. |
| 2022/0218340 A1 | 7/2022 | Harris et al. |
| 2022/0218344 A1 | 7/2022 | Leimbach et al. |
| 2022/0218345 A1 | 7/2022 | Shelton, IV et al. |
| 2022/0218346 A1 | 7/2022 | Shelton, IV et al. |
| 2022/0218347 A1 | 7/2022 | Shelton, IV et al. |
| 2022/0218348 A1 | 7/2022 | Swensgard et al. |
| 2022/0218349 A1 | 7/2022 | Shelton, IV et al. |
| 2022/0218350 A1 | 7/2022 | Shelton, IV et al. |
| 2022/0218351 A1 | 7/2022 | Shelton, IV et al. |
| 2022/0218376 A1 | 7/2022 | Shelton, IV et al. |
| 2022/0218378 A1 | 7/2022 | Shelton, IV et al. |
| 2022/0218381 A1 | 7/2022 | Leimbach et al. |
| 2022/0218382 A1 | 7/2022 | Leimbach et al. |
| 2022/0225980 A1 | 7/2022 | Shelton, IV et al. |
| 2022/0225981 A1 | 7/2022 | Shelton, IV et al. |
| 2022/0225982 A1 | 7/2022 | Yates et al. |
| 2022/0225986 A1 | 7/2022 | Shelton, IV et al. |
| 2022/0225992 A1 | 7/2022 | Smith et al. |
| 2022/0225993 A1 | 7/2022 | Huitema et al. |
| 2022/0225994 A1 | 7/2022 | Setser et al. |
| 2022/0226012 A1 | 7/2022 | Shelton, IV et al. |
| 2022/0226013 A1 | 7/2022 | Hall et al. |
| 2022/0233184 A1 | 7/2022 | Parihar et al. |
| 2022/0233185 A1 | 7/2022 | Parihar et al. |
| 2022/0233186 A1 | 7/2022 | Timm et al. |
| 2022/0233187 A1 | 7/2022 | Timm et al. |
| 2022/0233188 A1 | 7/2022 | Timm et al. |
| 2022/0233194 A1 | 7/2022 | Baxter, III et al. |
| 2022/0233195 A1 | 7/2022 | Shelton, IV et al. |
| 2022/0233257 A1 | 7/2022 | Shelton, IV et al. |
| 2022/0240927 A1 | 8/2022 | Timm et al. |
| 2022/0240928 A1 | 8/2022 | Timm et al. |
| 2022/0240929 A1 | 8/2022 | Timm et al. |
| 2022/0240930 A1 | 8/2022 | Yates et al. |
| 2022/0240936 A1 | 8/2022 | Huitema et al. |
| 2022/0240937 A1 | 8/2022 | Shelton, IV et al. |
| 2022/0249095 A1 | 8/2022 | Shelton, IV et al. |
| 2022/0265272 A1 | 8/2022 | Li et al. |
| 2022/0273291 A1 | 9/2022 | Shelton, IV et al. |
| 2022/0273292 A1 | 9/2022 | Shelton, IV et al. |
| 2022/0273293 A1 | 9/2022 | Shelton, IV et al. |
| 2022/0273294 A1 | 9/2022 | Creamer et al. |
| 2022/0273299 A1 | 9/2022 | Shelton, IV et al. |
| 2022/0273300 A1 | 9/2022 | Shelton, IV et al. |
| 2022/0273301 A1 | 9/2022 | Creamer et al. |
| 2022/0273302 A1 | 9/2022 | Shelton, IV et al. |
| 2022/0273303 A1 | 9/2022 | Creamer et al. |
| 2022/0273304 A1 | 9/2022 | Shelton, IV et al. |
| 2022/0273305 A1 | 9/2022 | Shelton, IV et al. |
| 2022/0273306 A1 | 9/2022 | Shelton, IV et al. |
| 2022/0273307 A1 | 9/2022 | Shelton, IV et al. |
| 2022/0273308 A1 | 9/2022 | Shelton, IV et al. |
| 2022/0278438 A1 | 9/2022 | Shelton, IV et al. |
| 2022/0287711 A1 | 9/2022 | Ming et al. |
| 2022/0296230 A1 | 9/2022 | Adams et al. |
| 2022/0296231 A1 | 9/2022 | Adams et al. |
| 2022/0296232 A1 | 9/2022 | Adams et al. |
| 2022/0296233 A1 | 9/2022 | Morgan et al. |
| 2022/0296234 A1 | 9/2022 | Shelton, IV et al. |
| 2022/0296235 A1 | 9/2022 | Morgan et al. |
| 2022/0296236 A1 | 9/2022 | Bakos et al. |
| 2022/0296237 A1 | 9/2022 | Bakos et al. |
| 2022/0304679 A1 | 9/2022 | Bakos et al. |
| 2022/0304680 A1 | 9/2022 | Shelton, IV et al. |
| 2022/0304681 A1 | 9/2022 | Shelton, IV et al. |
| 2022/0304682 A1 | 9/2022 | Shelton, IV et al. |
| 2022/0304683 A1 | 9/2022 | Shelton, IV et al. |
| 2022/0304684 A1 | 9/2022 | Bakos et al. |
| 2022/0304685 A1 | 9/2022 | Bakos et al. |
| 2022/0304686 A1 | 9/2022 | Shelton, IV et al. |
| 2022/0304687 A1 | 9/2022 | Shelton, IV et al. |
| 2022/0304688 A1 | 9/2022 | Shelton, IV et al. |
| 2022/0304689 A1 | 9/2022 | Shelton, IV |
| 2022/0304690 A1 | 9/2022 | Baxter, III et al. |
| 2022/0304714 A1 | 9/2022 | Shelton, IV et al. |
| 2022/0304715 A1 | 9/2022 | Shelton, IV |
| 2022/0313253 A1 | 10/2022 | Shelton, IV et al. |
| 2022/0313263 A1 | 10/2022 | Huitema et al. |
| 2022/0313619 A1 | 10/2022 | Schmid et al. |
| 2022/0323067 A1 | 10/2022 | Overmyer et al. |
| 2022/0323070 A1 | 10/2022 | Ross et al. |
| 2022/0330940 A1 | 10/2022 | Shelton, IV et al. |
| 2022/0338870 A1 | 10/2022 | Swayze et al. |
| 2022/0346774 A1 | 11/2022 | Hess et al. |
| 2022/0346775 A1 | 11/2022 | Hess et al. |
| 2022/0346776 A1 | 11/2022 | Aronhalt et al. |
| 2022/0346781 A1 | 11/2022 | Shelton, IV et al. |
| 2022/0346783 A1 | 11/2022 | Shelton, IV et al. |
| 2022/0346785 A1 | 11/2022 | Aronhalt et al. |
| 2022/0354492 A1 | 11/2022 | Baril |
| 2022/0354493 A1 | 11/2022 | Shelton, IV et al. |
| 2022/0354495 A1 | 11/2022 | Baxter, III et al. |
| 2022/0361879 A1 | 11/2022 | Baxter, III et al. |
| 2022/0370069 A1 | 11/2022 | Simms et al. |
| 2022/0378418 A1 | 12/2022 | Huang et al. |
| 2022/0378420 A1 | 12/2022 | Leimbach et al. |
| 2022/0378424 A1 | 12/2022 | Huang et al. |
| 2022/0378425 A1 | 12/2022 | Huang et al. |
| 2022/0378426 A1 | 12/2022 | Huang et al. |
| 2022/0378427 A1 | 12/2022 | Huang et al. |
| 2022/0378428 A1 | 12/2022 | Shelton, IV et al. |
| 2022/0378435 A1 | 12/2022 | Dholakia et al. |
| 2022/0387030 A1 | 12/2022 | Shelton, IV et al. |
| 2022/0387031 A1 | 12/2022 | Yates et al. |
| 2022/0387032 A1 | 12/2022 | Huitema et al. |
| 2022/0387033 A1 | 12/2022 | Huitema et al. |
| 2022/0387034 A1 | 12/2022 | Huitema et al. |
| 2022/0387035 A1 | 12/2022 | Huitema et al. |
| 2022/0387036 A1 | 12/2022 | Huitema et al. |
| 2022/0387037 A1 | 12/2022 | Huitema et al. |
| 2022/0387038 A1 | 12/2022 | Huitema et al. |
| 2022/0387125 A1 | 12/2022 | Leimbach et al. |
| 2023/0016171 A1 | 1/2023 | Yates et al. |
| 2023/0018950 A1 | 1/2023 | Shelton, IV et al. |
| 2023/0057935 A1 | 2/2023 | Baber et al. |
| 2023/0088531 A1 | 3/2023 | Hall et al. |
| 2023/0094712 A1 | 3/2023 | Shelton, IV et al. |
| 2023/0120983 A1 | 4/2023 | Stokes et al. |
| 2023/0121131 A1 | 4/2023 | Swayze et al. |
| 2023/0121658 A1 | 4/2023 | Stokes et al. |
| 2023/0133811 A1 | 5/2023 | Huang |
| 2023/0134883 A1 | 5/2023 | Leimbach |
| 2023/0135070 A1 | 5/2023 | Shelton, IV et al. |
| 2023/0135282 A1 | 5/2023 | Schings et al. |
| 2023/0135811 A1 | 5/2023 | Guest |
| 2023/0138314 A1 | 5/2023 | Jenkins |
| 2023/0138743 A1 | 5/2023 | Ross et al. |
| 2023/0165582 A1 | 6/2023 | Harris et al. |
| 2023/0165584 A1 | 6/2023 | Leimbach et al. |
| 2023/0172607 A1 | 6/2023 | DiNardo et al. |

FOREIGN PATENT DOCUMENTS

| | | |
|---|---|---|
| AU | 2012268848 A1 | 1/2013 |
| AU | 2011218702 B2 | 6/2013 |
| AU | 2012200178 B2 | 7/2013 |
| BR | 112013007744 A2 | 6/2016 |

(56) References Cited

FOREIGN PATENT DOCUMENTS

| | | | |
|---|---|---|---|
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101401736 | A | 4/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 204092074 | U | 1/2015 |
| CN | 104337556 | A | 2/2015 |
| CN | 204158440 | U | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |
| CN | 103860225 | B | 3/2016 |
| CN | 103750872 | B | 5/2016 |
| CN | 105682566 | A | 6/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |

(56) References Cited

FOREIGN PATENT DOCUMENTS

| | | |
|---|---|---|
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1558161 A1 | 8/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 2153793 A2 | 2/2010 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2529671 A2 | 12/2012 |
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2789299 A1 | 10/2014 |
| EP | 2842500 A1 | 3/2015 |
| EP | 2853220 A1 | 4/2015 |
| EP | 2878274 A1 | 6/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 3120781 A2 | 1/2017 |
| EP | 3135225 A2 | 3/2017 |
| EP | 2789299 B1 | 5/2017 |
| EP | 3225190 A2 | 10/2017 |
| EP | 3235445 A1 | 10/2017 |
| EP | 3326548 A1 | 5/2018 |
| EP | 3363378 A1 | 8/2018 |
| EP | 3409216 A1 | 12/2018 |
| EP | 3476301 A1 | 5/2019 |
| EP | 3476334 A1 | 5/2019 |
| EP | 3275378 B1 | 7/2019 |
| EP | 3505095 A1 | 7/2019 |
| EP | 3791810 A1 | 3/2021 |
| ES | 1070456 U | 9/2009 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | 56333137 A | 2/1988 |
| JP | S63270040 A | 11/1988 |
| JP | S63318824 A | 12/1988 |
| JP | H0129503 B2 | 6/1989 |
| JP | H02106189 A | 4/1990 |
| JP | H0378514 U | 8/1991 |
| JP | H0385009 U | 8/1991 |
| JP | H0489041 A | 3/1992 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H0636757 A | 2/1994 |
| JP | H06237937 A | 8/1994 |
| JP | H06304176 A | 11/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H0950795 A | 2/1997 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000210299 A | 8/2000 |
| JP | 2000271141 A | 10/2000 |
| JP | 2000287987 A | 10/2000 |
| JP | 2000325303 A | 11/2000 |
| JP | 2001-69758 A | 3/2001 |
| JP | 2001087272 A | 4/2001 |
| JP | 2001208655 A | 8/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |

(56) References Cited

FOREIGN PATENT DOCUMENTS

| | | |
|---|---|---|
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006291180 A | 10/2006 |
| JP | 2006346445 A | 12/2006 |
| JP | 2007-97252 A | 4/2007 |
| JP | 2007289715 A | 11/2007 |
| JP | 2007304057 A | 11/2007 |
| JP | 2007306710 A | 11/2007 |
| JP | D1322057 | 2/2008 |
| JP | 2008154804 A | 7/2008 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | D1383743 | 2/2010 |
| JP | 2010065594 A | 3/2010 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |
| JP | 2011200665 A | 10/2011 |
| JP | D1432094 | 12/2011 |
| JP | 1433631 S | 2/2012 |
| JP | 2012115542 A | 6/2012 |
| JP | 2012143283 A | 8/2012 |
| JP | 5154710 B1 | 2/2013 |
| JP | 2013099551 A | 5/2013 |
| JP | 2013126430 A | 6/2013 |
| JP | D1481426 | 9/2013 |
| JP | 2013541982 A | 11/2013 |
| JP | 2013541983 A | 11/2013 |
| JP | 2013541997 A | 11/2013 |
| JP | 2014018667 A | 2/2014 |
| JP | D1492363 | 2/2014 |
| JP | 2014121599 A | 7/2014 |
| JP | 2014171879 A | 9/2014 |
| JP | 1517663 S | 2/2015 |
| JP | 2015512725 A | 4/2015 |
| JP | 2015513956 A | 5/2015 |
| JP | 2015513958 A | 5/2015 |
| JP | 2015514471 A | 5/2015 |
| JP | 2015516838 A | 6/2015 |
| JP | 2015521524 A | 7/2015 |
| JP | 2015521525 A | 7/2015 |
| JP | 2016007800 A | 1/2016 |
| JP | 2016508792 A | 3/2016 |
| JP | 2016512057 A | 4/2016 |
| JP | 2016518914 A | 6/2016 |
| JP | 2016530949 A | 10/2016 |
| JP | 2017513563 A | 6/2017 |
| JP | 1601498 S | 4/2018 |
| JP | 2019513530 A | 5/2019 |
| JP | 2020501797 A | 1/2020 |
| JP | D1677030 S | 1/2021 |
| JP | D1696539 S | 10/2021 |
| KR | 20100110134 A | 10/2010 |
| KR | 20110003229 A | 1/2011 |
| KR | 300631507 | 3/2012 |
| KR | 300747646 | 6/2014 |
| KR | 20180053811 A | 5/2018 |
| RU | 1814161 A1 | 5/1993 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |
| SU | 728848 A1 | 4/1980 |
| SU | 1009439 A | 4/1983 |
| SU | 1042742 A1 | 9/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| WO | WO-9308754 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0036690 A2 | 6/2000 |
| WO | WO-0053112 A2 | 9/2000 |
| WO | WO-0024448 A2 | 10/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |

(56) References Cited

FOREIGN PATENT DOCUMENTS

| | | |
|---|---|---|
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032762 A1 * | 4/2004 ........... A61B 17/068 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A2 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A1 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2014175894 A1 | 10/2014 |
| WO | WO-2015032797 A1 | 3/2015 |
| WO | WO-2015076780 A1 | 5/2015 |
| WO | WO-2015137040 A1 | 9/2015 |
| WO | WO-2015138760 A1 | 9/2015 |
| WO | WO-2015187107 A1 | 12/2015 |
| WO | WO-2016100682 A1 | 6/2016 |
| WO | WO-2016107448 A1 | 7/2016 |
| WO | WO-2017138905 A1 | 8/2017 |
| WO | WO-2018011664 A1 | 1/2018 |
| WO | WO-2019036490 A1 | 2/2019 |
| WO | WO-2019130087 A1 | 7/2019 |
| WO | WO-2019130089 A1 | 7/2019 |
| WO | WO-2019208902 A1 | 10/2019 |
| WO | WO-2021189234 A1 | 9/2021 |
| WO | WO-2022249091 A1 | 12/2022 |
| WO | WO-2022249094 A1 | 12/2022 |

OTHER PUBLICATIONS

Molina, "Low Level Reader Protocol (LLRP)," Oct. 13, 2010, pp. 1-198.

Makerbot, 10 Advantages of 3D Printing, 2020 (retrieved via the wayback machine), Makerbot.com (Year: 2020).

U.S. Appl. No. 62/798,651, filed Jan. 30, 2019.

U.S. Appl. No. 62/840,602, filed Apr. 30, 2019.

IPR2020-00050, Part 1 of 5.

IPR2020-00050, Part 2 of 5.

IPR2020-00050, Part 3 of 5.

IPR2020-00050, Part 4 of 5.

IPR2020-00050, Part 5 of 5.

IPR2020-00051, Part 1 of 6.

IPR2020-00051, Part 2 of 6.

IPR2020-00051, Part 3 of 6.

IPR2020-00051, Part 4 of 6.

IPR2020-00051, Part 5 of 6.

IPR2020-00051, Part 6 of 6.

United States Court of Appeals for the Federal Circuit, Appeal Nos. 2021-1995, 2021-1997, Appellant Ethicon LLC's Opening Brief, dated Sep. 10, 2021.

United States Court of Appeals for the Federal Circuit, Responsive Brief for Appellee Intuitive Surgical, Inc., Case 21/1995, Document 20, pp. 1-72, dated Nov. 3, 2021.

United States International Trade Commission, Initial Determination On Violation Of Section 337 And Recommended Determination On Remedy And Bond, Investigation No. 337-TA-1167, Public Version, dated Jun. 8, 2021.

United States International Trade Commission, Notice Of A Final Determination Finding A Violation Of Section 337 And Issuance Of Remedial Orders; Suspension Of Enforcement Of The Remedial Orders Pending Final Resolution Of A Final Written Decision By The Patent Trial And Appeal Board; And Termination Of The Investigation, Investigation No. 337-TA-1167, dated Oct. 14, 2021.

ITC Investigation No. 337-TA-1167 Commission Opinion (public version), dated Dec. 20, 2021.

United States Patent and Trademark Office, Before the Patent Trial and Appeal Board, Deposition of Frank Fronczak, Sep. 1, 2020, Exhibit 1019, Intuitive v. Ethicon, IPR2020-00050.

United States Patent and Trademark Office, Before the Patent Trial and Appeal Board, Deposition of Bryan Knodel, Ph.D., Oct. 23, 2020, Exhibit 2099.001, Intuitive v. Ethicon, IPR2020-00050.

United States Patent and Trademark Office, Before the Patent Trial and Appeal Board, Patent Owner Ethicon LLC's Response, dated Jun. 22, 2020, Paper 21, Intuitive v. Ethicon, IPR2020-00050.

United States Patent and Trademark Office, Before the Patent Trial and Appeal Board, Patent Owner Ethicon LLC's Sur-Reply, dated Nov. 2, 2020, Paper 38, Intuitive v. Ethicon, IPR2020-00050.

United States Patent and Trademark Office, Before the Patent Trial and Appeal Board, Petitioner's Reply to Patent Owner's Response, dated Sep. 21, 2020, Paper 29, Intuitive v. Ethicon, IPR2020-00050.

United States Patent and Trademark Office, Before the Patent Trial and Appeal Board, Petitioner's Sur-Sur-Reply to Patent Owner's Sur-Reply, dated Dec. 23, 2020, Paper 46, Intuitive v. Ethicon, IPR2020-00050.

United States Patent and Trademark Office, Before the Patent Trial and Appeal Board, Declaration of Dr. Bryan Knodel in Support of Petition for Inter Pules Review of U.S. Pat. No. 9,844,379, Exhibit 1003, dated Oct. 16, 2019.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

Disclosed Anonymously, "Motor-Driven Surgical Stapler Improvements," Research Disclosure Database No. 526041, Published: Feb. 2008.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 a Polarized Relay, Copyright Matsushita Electric Works, Ltd. (Known of at least as early as Aug. 17, 2010), 5 pages.

(56) References Cited

OTHER PUBLICATIONS

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy," vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. And Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Data Sheet of LM4F230H5QR, 2007.
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: a Possible New Option for Patients with Weight Regain," Surg Endosc (2006) vol. 20., pp. 1744-1748.
Serial Communication Protocol; Michael Lemmon Feb. 1, 2009; http://www3.nd.edu~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on

(56) References Cited

OTHER PUBLICATIONS

May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, Article ID 879294, Hindawi Publishing Corporation.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.

\* cited by examiner

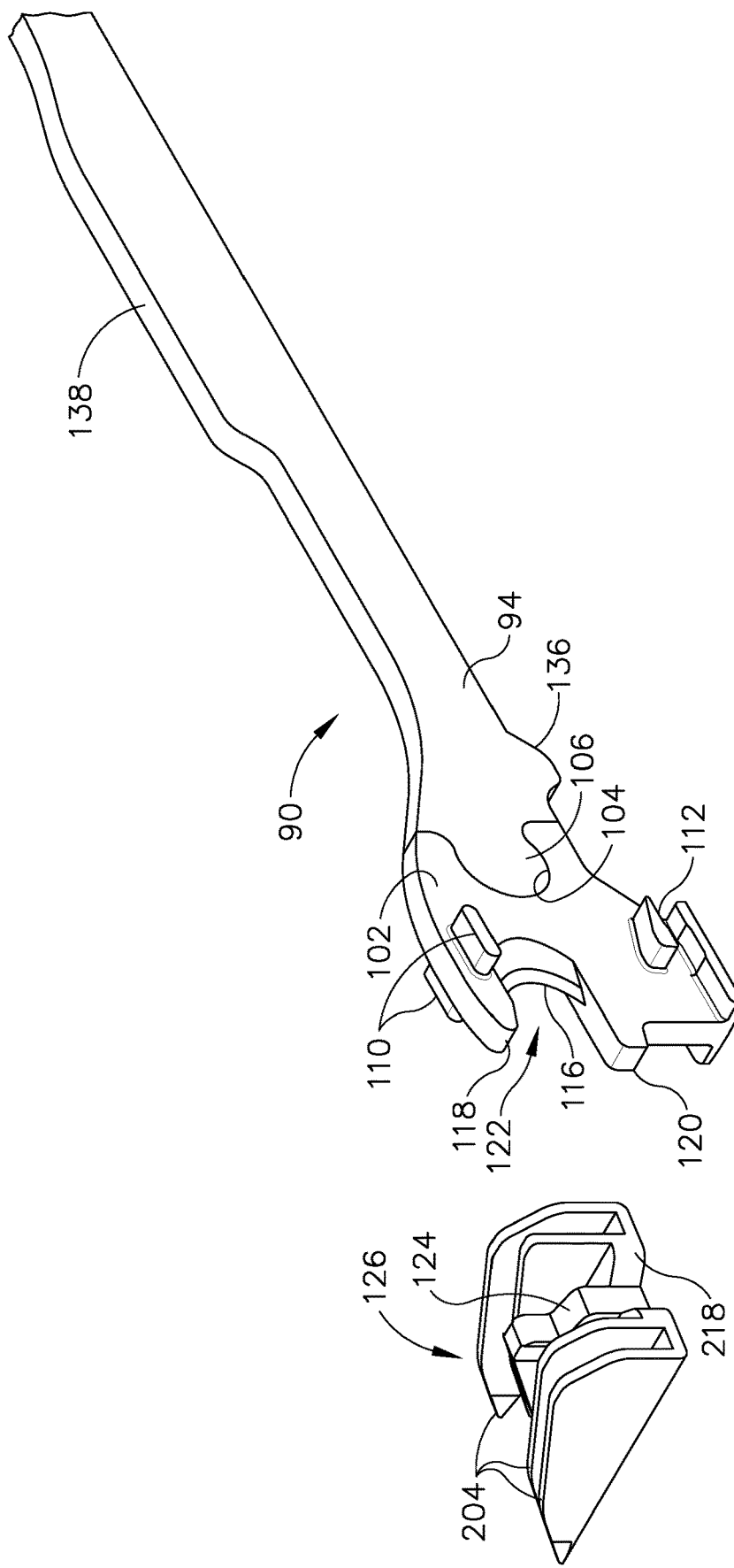

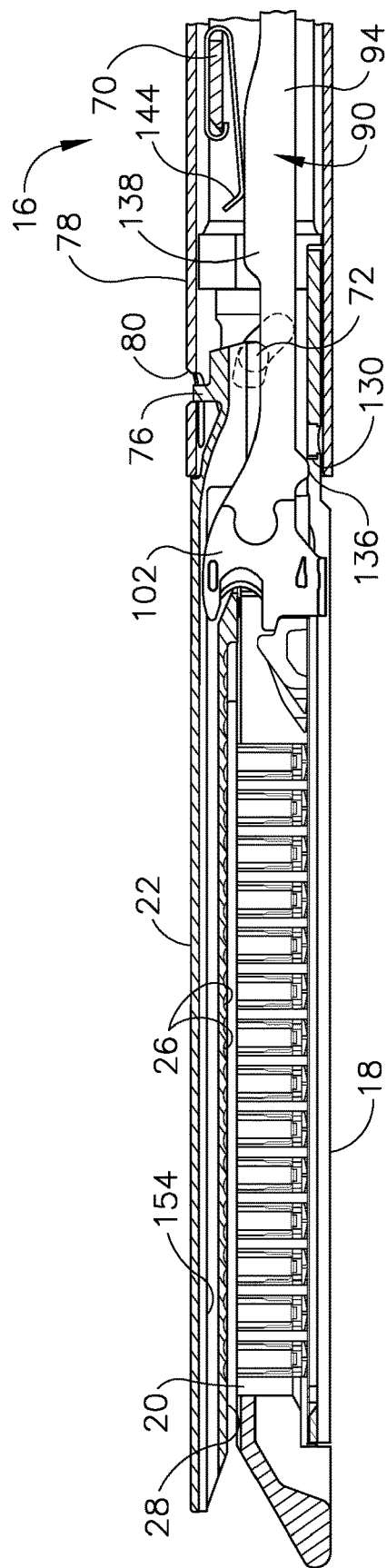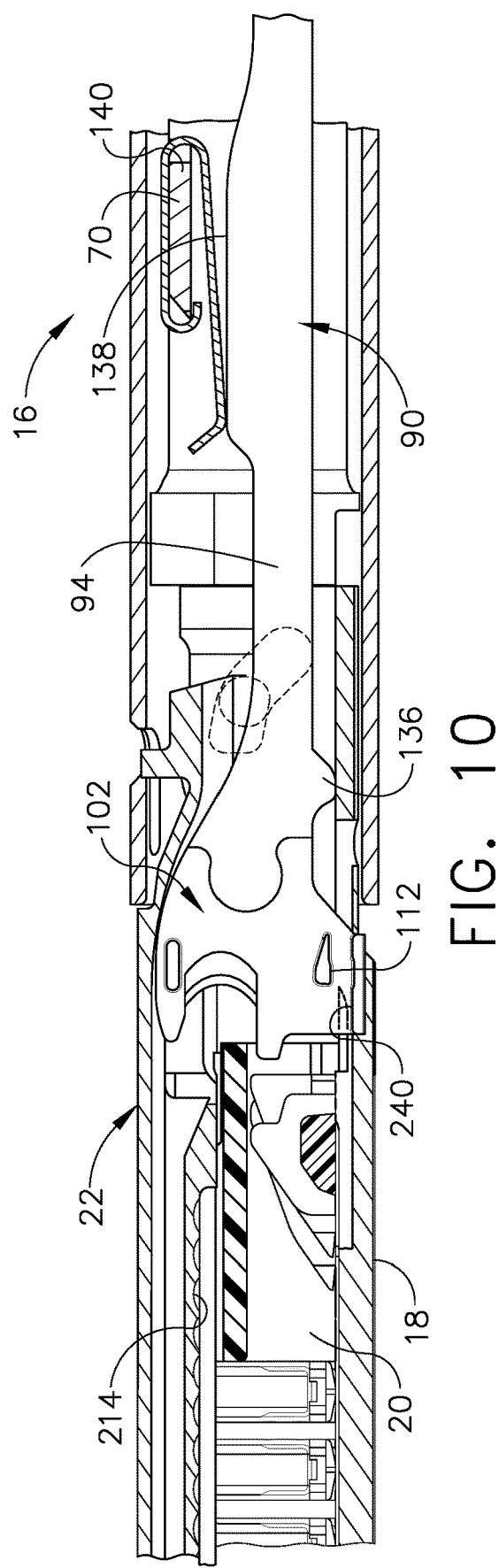

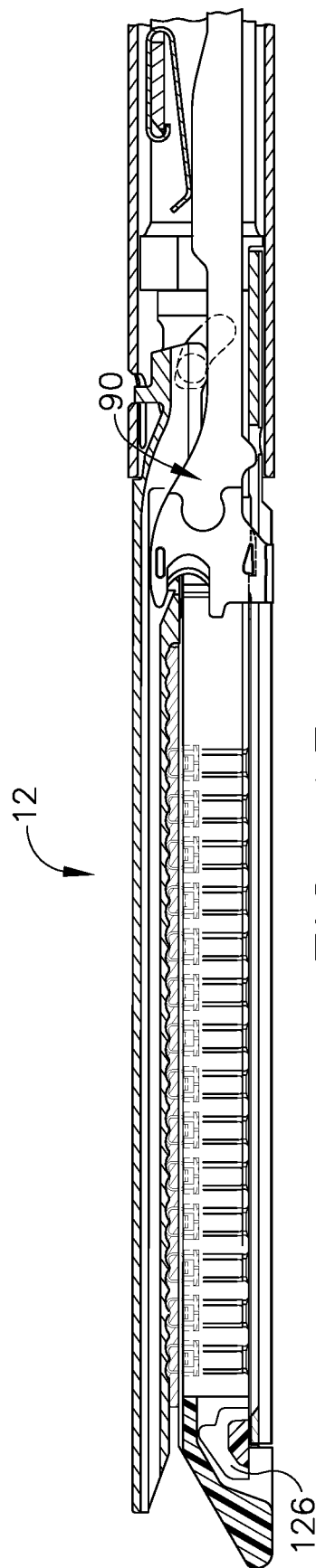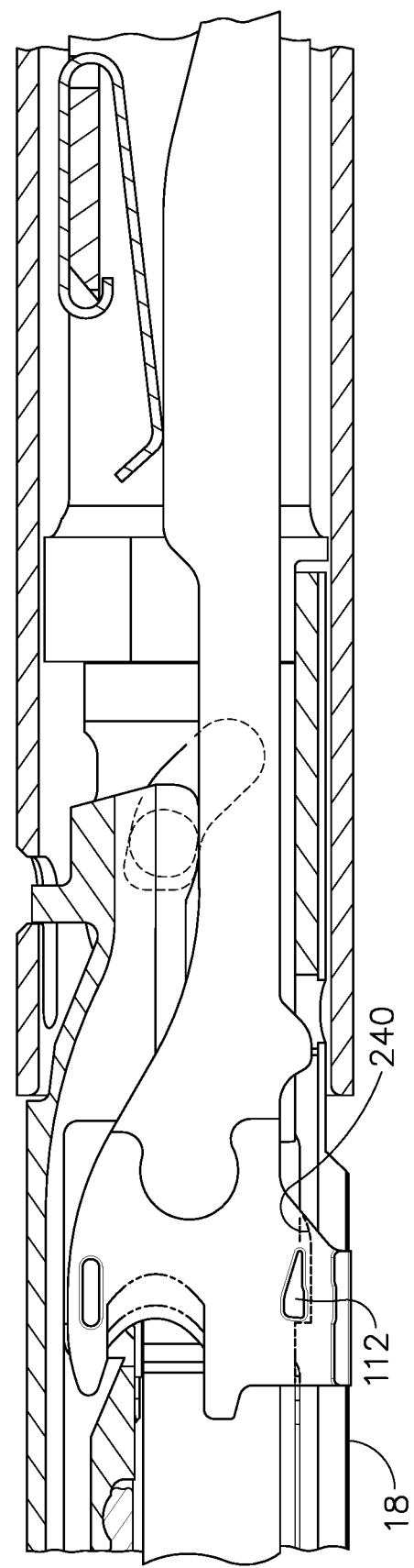

ARTICULATING SURGICAL STAPLING INSTRUMENT INCORPORATING A TWO-PIECE E-BEAM FIRING MECHANISM

CROSS-REFERENCE TO RELATED APPLICATIONS

This application is a continuation application claiming priority under 35 U.S.C. § 120 to U.S. patent application Ser. No. 16/384,096, entitled ARTICULATING SURGICAL STAPLING INSTRUMENT INCORPORATING A TWO-PIECE E-BEAM FIRING MECHANISM, filed Apr. 15, 2019, now U.S. Patent Application Publication No. 2019/0307456, which is a continuation application claiming priority under 35 U.S.C. § 120 to U.S. patent application Ser. No. 15/679,300, entitled ARTICULATING SURGICAL STAPLING INSTRUMENT INCORPORATING A TWO-PIECE E-BEAM FIRING MECHANISM, filed Aug. 17, 2017, which issued on May 21, 2019 as U.S. Pat. No. 10,292,707, which is a continuation application claiming priority under 35 U.S.C. § 120 to U.S. patent application Ser. No. 14/850,030, entitled ARTICULATING SURGICAL STAPLING INSTRUMENT INCORPORATING A TWO-PIECE E-BEAM FIRING MECHANISM, filed Sep. 10, 2015, which issued on Aug. 22, 2017 as U.S. Pat. No. 9,737,303, which is a continuation application claiming priority under 35 U.S.C. § 120 to U.S. patent application Ser. No. 14/521,748, entitled STAPLE CARTRIDGE, filed Oct. 23, 2014, which issued on Dec. 6, 2016 as U.S. Pat. No. 9,510,830, which is a continuation application claiming priority under 35 U.S.C. § 120 to U.S. patent application Ser. No. 14/175,148, entitled SURGICAL STAPLING INSTRUMENT, filed Feb. 7, 2014, which issued on Mar. 15, 2016 as U.S. Pat. No. 9,282,966, which is a continuation-in-part application claiming priority under 35 U.S.C. § 120 to U.S. patent application Ser. No. 13/369,601, entitled ROBOTICALLY-CONTROLLED SURGICAL END EFFECTOR SYSTEM, filed on Feb. 9, 2012, which issued on Jul. 22, 2014 as U.S. Pat. No. 8,783,541, which is a continuation application claiming priority under 35 U.S.C. § 120 to U.S. patent application Ser. No. 13/118,246, entitled ROBOTICALLY-DRIVEN SURGICAL INSTRUMENT WITH E-BEAM DRIVER, filed on May 27, 2011, which issued on Jun. 23, 2015 as U.S. Pat. No. 9,060,770, which is a continuation-in-part application claiming priority under 35 U.S.C. § 120 to U.S. patent application Ser. No. 11/538,154, entitled ARTICULATING SURGICAL STAPLING INSTRUMENT INCORPORATING A TWO-PIECE E-BEAM FIRING MECHANISM, filed on Oct. 3, 2006, now U.S. Patent Application Publication No. 2007/0084897, the entire disclosures of which are hereby incorporated by reference herein. This application is a continuation application claiming priority under 35 U.S.C. § 120 to U.S. patent application Ser. No. 16/384,096, entitled ARTICULATING SURGICAL STAPLING INSTRUMENT INCORPORATING A TWO-PIECE E-BEAM FIRING MECHANISM, filed Apr. 15, 2019, now U.S. Patent Application Publication No. 2019/0307456, which is a continuation application claiming priority under 35 U.S.C. § 120 to U.S. patent application Ser. No. 15/679,300, entitled ARTICULATING SURGICAL STAPLING INSTRUMENT INCORPORATING A TWO-PIECE E-BEAM FIRING MECHANISM, filed Aug. 17, 2017, which issued on May 21, 2019 as U.S. Pat. No. 10,292,707, which is a continuation application claiming priority under 35 U.S.C. § 120 to U.S. patent application Ser. No. 14/850,030, entitled ARTICULATING SURGICAL STAPLING INSTRUMENT INCORPORATING A TWO-PIECE E-BEAM FIRING MECHANISM, filed Sep. 10, 2015, which issued on Aug. 22, 2017 as U.S. Pat. No. 9,737,303, which is a continuation application under 35 U.S.C. § 120 to U.S. patent application Ser. No. 14/521,748, entitled STAPLE CARTRIDGE, filed Oct. 23, 2014, which issued on Dec. 6, 2016 as U.S. Pat. No. 9,510,830, which is a continuation application claiming priority under 35 U.S.C. § 120 to U.S. patent application Ser. No. 14/175,148, entitled SURGICAL STAPLING INSTRUMENT, filed Feb. 7, 2014, which issued on Mar. 15, 2016 as U.S. Pat. No. 9,282,966, which is a continuation-in-part application claiming priority under 35 U.S.C. § 120 to U.S. patent application Ser. No. 11/141,753, entitled SURGICAL STAPLING INSTRUMENT HAVING AN ELECTROACTIVE POLYMER ACTUATED MEDICAL SUBSTANCE DISPENSER, filed on Jun. 1, 2005, which issued on Dec. 9, 2014 as U.S. Pat. No. 8,905,977, which claims the benefit under 35 U.S.C. § 119(e) of U.S. Provisional Patent Application Ser. No. 60/591,694, entitled SURGICAL INSTRUMENT INCORPORATING AN ELECTRICALLY ACTUATED ARTICULATION MECHANISM, filed on Jul. 28, 2004, the entire disclosures of which are hereby incorporated by reference herein.

FIELD OF THE INVENTION

The present invention relates in general to surgical instruments that are suitable for endoscopically inserting an end effector that is actuated by a longitudinally driven firing member, and more particularly a surgical stapling and severing instrument that has an articulating shaft.

BACKGROUND OF THE INVENTION

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Positioning the end effector is constrained by the trocar. Generally these endoscopic surgical instruments include a long shaft between the end effector and a handle portion manipulated by the clinician. This long shaft enables insertion to a desired depth and rotation about the longitudinal axis of the shaft, thereby positioning the end effector to a degree. With judicious placement of the trocar and use of graspers, for instance, through another trocar, often this amount of positioning is sufficient. Surgical stapling and severing instruments, such as described in U.S. Pat. No. 5,465,895, are an example of an endoscopic surgical instrument that successfully positions an end effector by insertion and rotation.

More recently, U.S. patent application Ser. No. 10/443,617, entitled SURGICAL STAPLING INSTRUMENT INCORPORATING AN E-BEAM FIRING MECHANISM, filed on May 20, 2003, now U.S. Pat. No. 6,978,921, which is incorporated by reference in its entirety, describes an improved "E-beam" firing bar for severing tissue and actuating staples. Some of the additional advantages include affirmatively spacing the jaws of the end effector, or more specifically a staple applying assembly, even if slightly too much or too little tissue is clamped for optimal staple formation. Moreover, the E-beam firing bar engages the end effector and staple cartridge in a way that enables several beneficial lockouts to be incorporated.

Depending upon the nature of the operation, it may be desirable to further adjust the positioning of the end effector of an endoscopic surgical instrument. In particular, it is often desirable to orient the end effector at an axis transverse to the longitudinal axis of the shaft of the instrument. The transverse movement of the end effector relative to the instrument shaft is conventionally referred to as "articulation". This is typically accomplished by a pivot (or articulation) joint being placed in the extended shaft just proximal to the staple applying assembly. This allows the surgeon to articulate the staple applying assembly remotely to either side for better surgical placement of the staple lines and easier tissue manipulation and orientation. This articulated positioning permits the clinician to more easily engage tissue in some instances, such as behind an organ. In addition, articulated positioning advantageously allows an endoscope to be positioned behind the end effector without being blocked by the instrument shaft.

Approaches to articulating a surgical stapling and severing instrument tend to be complicated by integrating control of the articulation along with the control of closing the end effector to clamp tissue and fire the end effector (i.e., stapling and severing) within the small diameter constraints of an endoscopic instrument. Generally, the three control motions are all transferred through the shaft as longitudinal translations. For instance, U.S. Pat. No. 5,673,840 discloses an accordion-like articulation mechanism ("flex-neck") that is articulated by selectively drawing back one of two connecting rods through the implement shaft, each rod offset respectively on opposite sides of the shaft centerline. The connecting rods ratchet through a series of discrete positions.

Another example of longitudinal control of an articulation mechanism is U.S. Pat. No. 5,865,361 that includes an articulation link offset from a camming pivot such that pushing or pulling longitudinal translation of the articulation link effects articulation to a respective side. Similarly, U.S. Pat. No. 5,797,537 discloses a similar rod passing through the shaft to effect articulation.

In commonly-owned U.S. patent application Ser. No. 10/615,973, entitled SURGICAL INSTRUMENT INCORPORATING AN ARTICULATION MECHANISM HAVING ROTATION ABOUT THE LONGITUDINAL AXIS, now U.S. Pat. No. 7,111,769, the disclosure of which is hereby incorporated by reference in its entirety, a rotational motion is used to transfer articulation motion as an alternative to a longitudinal motion.

In the application entitled SURGICAL STAPLING INSTRUMENT INCORPORATING AN E-BEAM FIRING MECHANISM, U.S. patent application Ser. No. 10/443,617, filed on May 20, 2003, now U.S. Pat. No. 6,978,921, the disclosure of which was previously incorporated by reference in its entirety, a surgical severing and stapling instrument, suitable for laparoscopic and endoscopic clinical procedures, clamps tissue within an end effector of an elongate channel pivotally opposed by an anvil. An E-beam firing bar moves distally through the clamped end effector to sever tissue and to drive staples on each side of the cut. The E-beam firing bar affirmatively spaces the anvil from the elongate channel to assure properly formed closed staples, especially when an amount of tissue is clamped that is inadequate to space the end effector. In particular, an upper pin of the firing bar longitudinally moves through an anvil slot and a channel slot is captured between a lower cap and a middle pin of the firing bar to assure a minimum spacing. While this E-beam firing bar has a number of advantages, additional features are desirable to enhance manufacturability and to minimize dimensional variations.

Consequently, a significant need exists for a surgical instrument with a firing bar that advantageously assures proper spacing between clamped jaws of an end effector and which facilitates articulation of its shaft.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 is a perspective view of a two-piece knife and firing bar ("E-beam") of the staple applying assembly of FIG. 2.

FIG. 5 is a perspective view of a wedge sled of a staple cartridge of the staple applying assembly of FIG. 1.

FIG. 9 is a left side view in elevation taken generally along the longitudinal axis of line 6-6 of a closed staple applying assembly of FIG. 2 to include center contact points between the two-piece knife and wedge sled but also laterally offset to show staples and staple drivers within the staple cartridge.

FIG. 10 is a left side detail view in elevation of the staple applying assembly of FIG. 9 with the two-piece knife retracted slightly more as typical for staple cartridge replacement.

FIG. 13 is a left side cross-sectional view in elevation of the closed staple applying assembly of FIG. 12 after firing of the staple cartridge and retraction of the two-piece knife.

FIG. 14 is a left side cross-sectional detail view in elevation of the staple applying assembly of FIG. 13 with the two-piece knife allowed to drop into a lockout position.

DETAILED DESCRIPTION OF THE INVENTION

The entire disclosure of U.S. patent application Ser. No. 11/082,495, entitled SURGICAL INSTRUMENT INCORPORATING AN ELECTRICALLY ACTUATED ARTICULATION MECHANISM, filed on Mar. 17, 2005, now U.S. Pat. No. 7,506,790, is incorporated herein by reference. The entire disclosure of U.S. Pat. No. 6,667,825, entitled STABLE CONJUGATED POLYMER ELECTROCHROMIC DEVICES INCORPORATING IONIC LIQUIDS, issued on Jan. 3, 2002, is incorporated herein by reference. The entire disclosure of U.S. patent application Ser. No. 11/061,908, entitled SURGICAL INSTRUMENT INCORPORATING A FLUID TRANSFER CONTROLLED ARTICULATION MECHANISM, filed on Feb. 18, 2005, now U.S. Pat. No. 7,559,450, is incorporated herein by reference.

Figure 1:
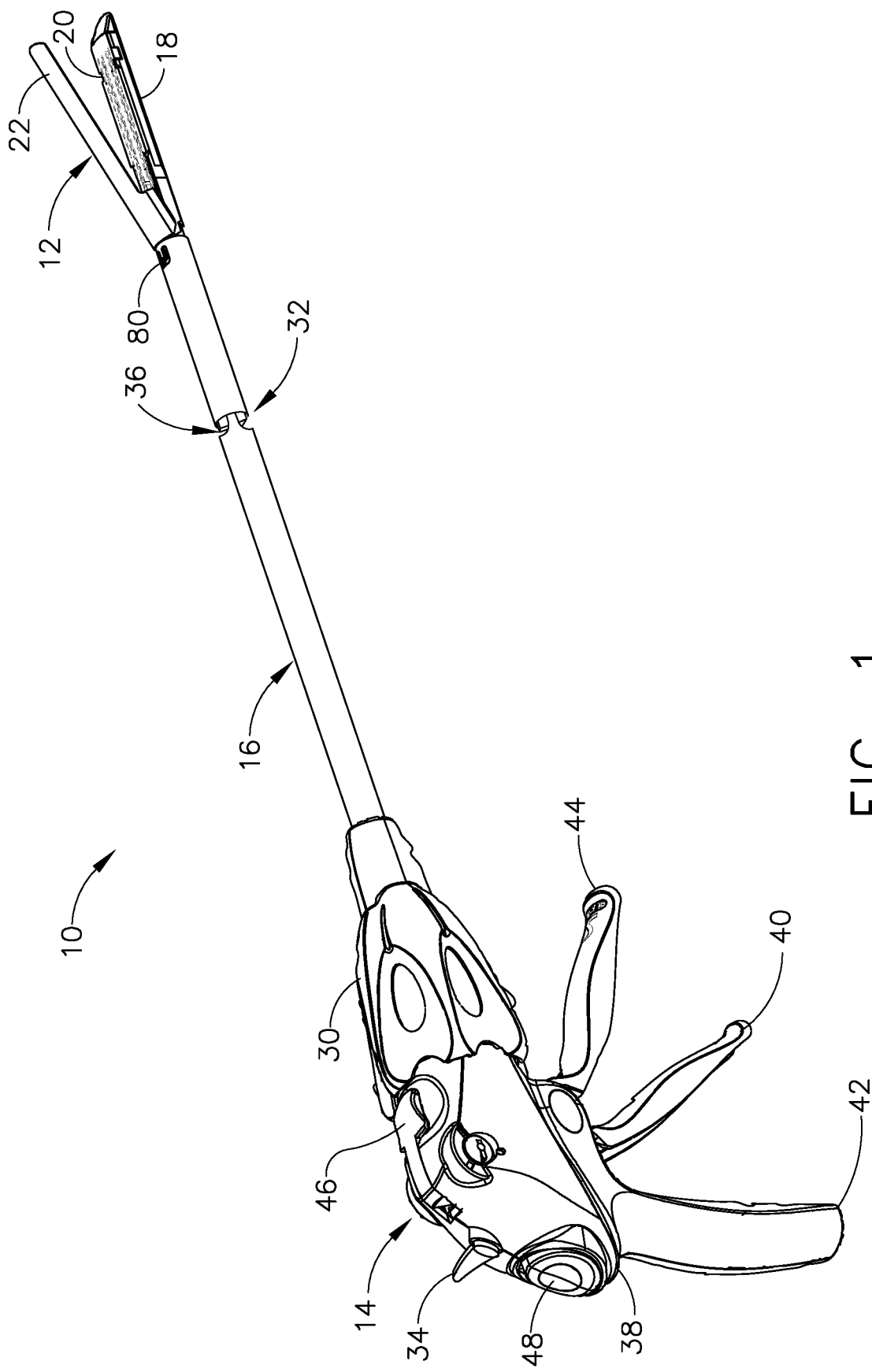
FIG. 1 is a perspective view of an endoscopic surgical stapling instrument for surgical stapling and severing in an open, unarticulated state.
Figure 2:
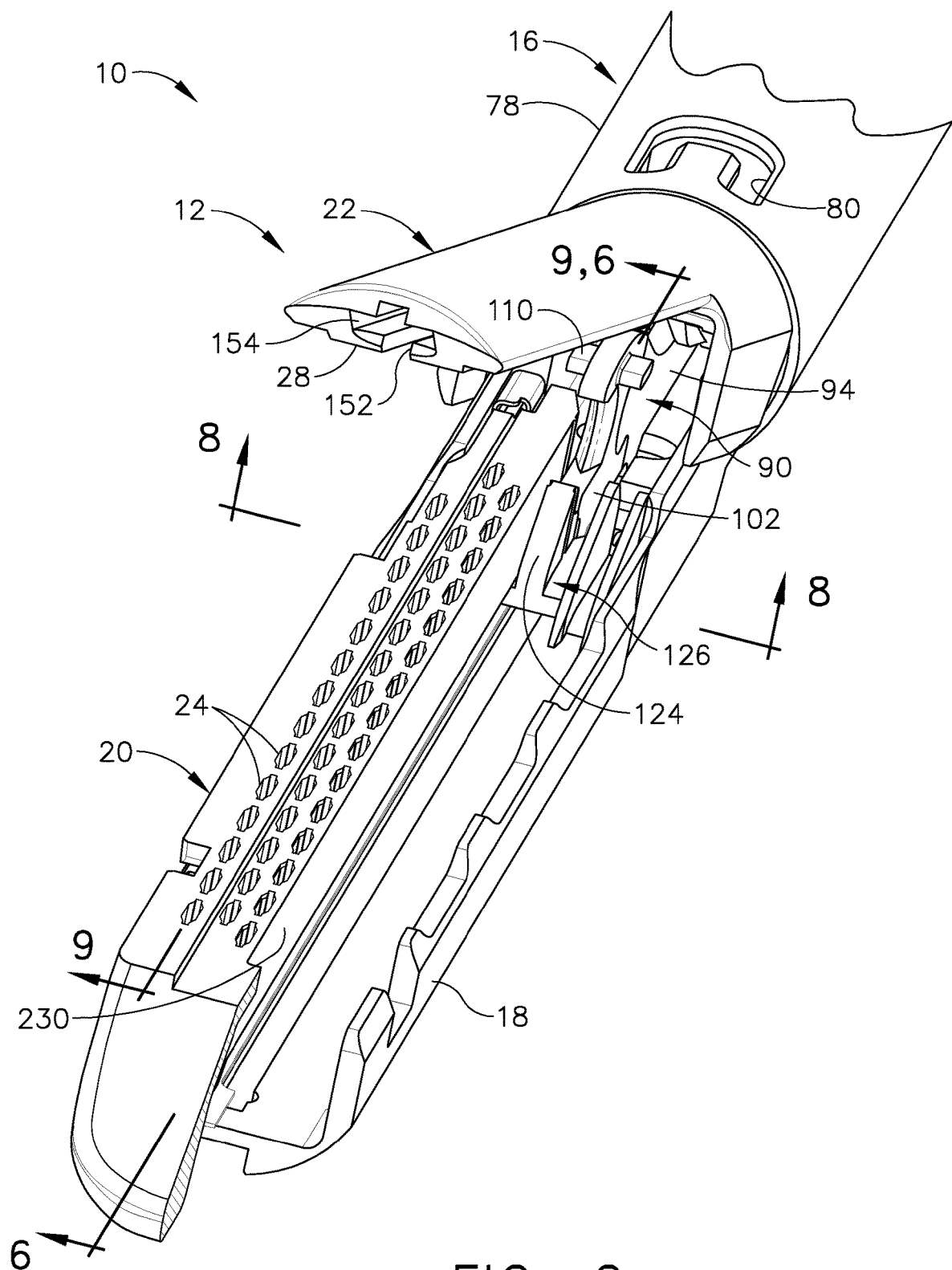
FIG. 2 is a left, front perspective view of an open staple applying assembly of the surgical stapling instrument of FIG. 1 with a right half portion of a replaceable staple cartridge included in a staple channel.
Figure 3:
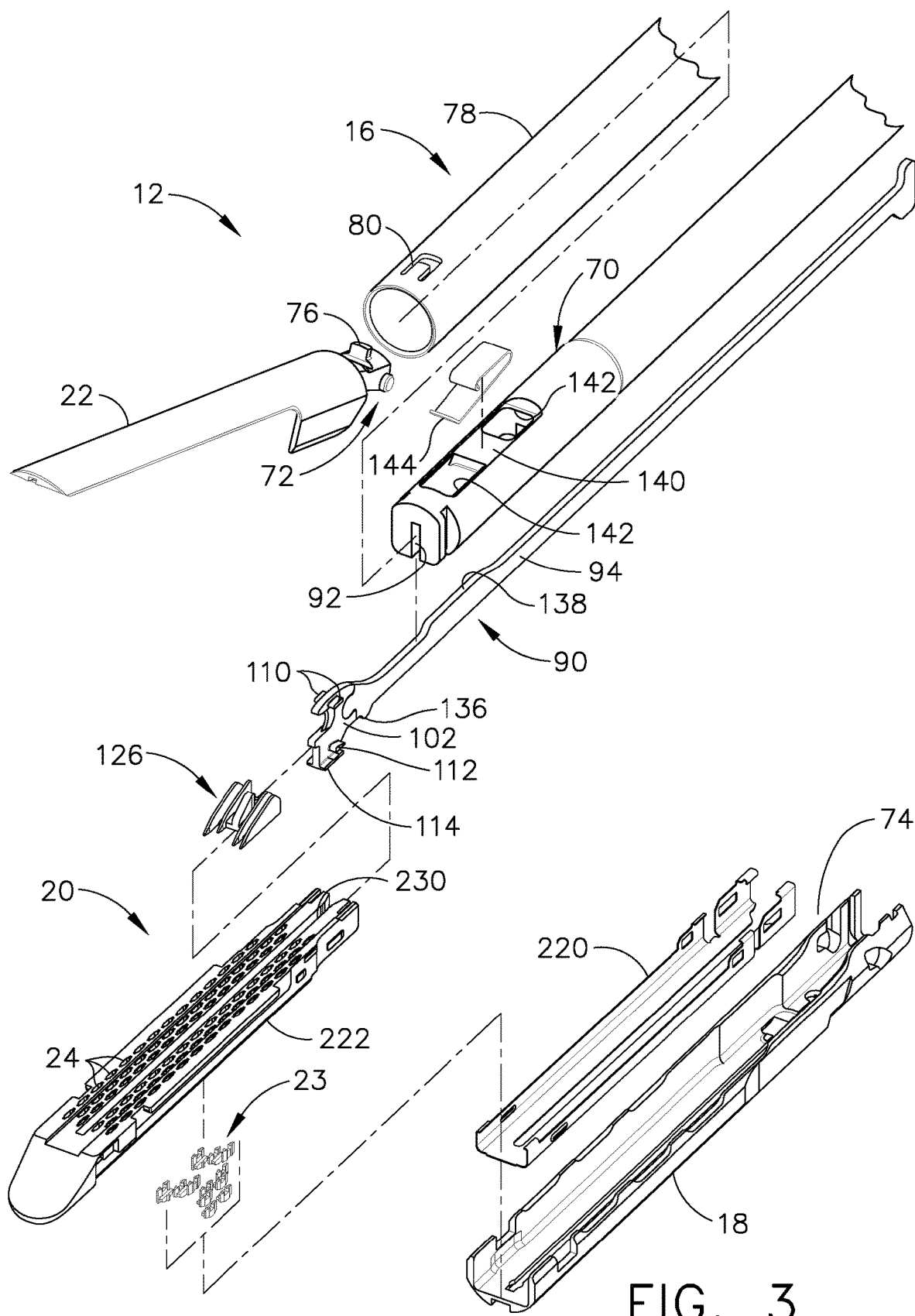
FIG. 3 is an exploded perspective view of the staple applying assembly of FIG. 2 with a complete replaceable staple cartridge and an alternative nonarticulating shaft configuration.

In FIGS. 1-3, a surgical stapling instrument 10 has at its distal end an end effector, depicted as a staple applying assembly 12, spaced apart from a handle 14 (FIG. 2) by an elongate shaft 16. The staple applying assembly 12 includes a staple channel 18 for receiving a replaceable staple cartridge 20. Pivotally attached to the staple channel 18 is an anvil 22 that clamps tissue to the staple cartridge 20 and serves to deform staples 23 (FIG. 3) driven up from staple holes 24 in the staple cartridge 20 against staple forming recesses 26 (FIG. 6) in an anvil undersurface 28 into a closed shape. When the staple applying assembly 12 is closed, its cross sectional area, as well as the elongate shaft 16 are suitable for insertion through a small surgical opening, such as through a cannula of a trocar (not shown).

With particular reference to FIG. 1, correct placement and orientation of the staple applying assembly 12 is facilitated by controls on the handle 14. In particular, a rotation knob 30 causes rotation of the shaft 16 about its longitudinal axis, and hence rotation of the staple applying assembly 12. Additional positioning is enabled at an articulation joint 32 in the shaft 16 that pivots the staple applying assembly 12 in an arc from the longitudinal axis of the shaft 16, thereby allowing placement behind an organ or allowing other instruments such as an endoscope (not shown) to be oriented behind the staple applying assembly 12. This articulation is advantageously effected by an articulation control switch 34 on the handle 14 that transmits an electrical signal to the articulation joint 32 to an Electroactive Polymer (EAP) actuator 36, powered by an EAP controller and power supply 38 contained within the handle 14.

Once positioned with tissue in the staple applying assembly 12, a surgeon closes the anvil 22 by drawing a closure trigger 40 proximally toward a pistol grip 42. Once clamped thus, the surgeon may grasp a more distally presented firing trigger 44, drawing it back to effect firing of the staple applying assembly 12, which in some applications is achieved in one single firing stroke and in other applications by multiple firing strokes. Firing accomplishes simultaneously stapling of at least two rows of staples while severing the tissue therebetween.

Retraction of the firing components may be automatically initiated upon full travel. Alternatively, a retraction lever 46 may be drawn aft to effect retraction. With the firing components retracted, the staple applying assembly 12 may be unclamped and opened by the surgeon slightly drawing the closure trigger 40 aft toward the pistol grip 42 and depressing a closure release button 48 and then releasing the closure trigger 40, thereby releasing the two stapled ends of severed tissue from the staple applying assembly 12.

Staple Applying Assembly

While an articulation joint 32 is depicted in FIG. 1, for clarity and as an alternative application, the surgical stapling instrument 10 of FIGS. 2-14 omit an articulation joint 32. It should be appreciated, however, that aspects of the present invention have particular advantages for articulation as described below with regard to FIGS. 15-18.

In FIGS. 1-3, the staple applying assembly 12 accomplishes the functions of clamping onto tissue, driving staples and severing tissue by two distinct motions transferred longitudinally down the shaft 16 over a shaft frame 70. This shaft frame 70 is proximally attached to the handle 14 and coupled for rotation with the rotation knob 30. An illustrative multi-stroke handle 14 for the surgical stapling and severing instrument 10 of FIG. 1 is described in greater detail in the commonly-owned U.S. patent application Ser. No. 10/674,026, entitled SURGICAL STAPLING INSTRUMENT INCORPORATING A MULTISTROKE FIRING POSITION INDICATOR AND RETRACTION MECHANISM, now U.S. Pat. No. 7,364,061, the disclosure of which is hereby incorporated by reference in its entirety, with additional features and variation as described herein. While a multi-stroke handle 14 advantageously supports applications with high firing forces over a long distance, applications consistent with the present invention may incorporate a single firing stroke, such as described in commonly-owned U.S. patent application Ser. No. 10/441,632, entitled SURGICAL STAPLING INSTRUMENT HAVING SEPARATE DISTINCT CLOSING AND FIRING SYSTEMS, now U.S. Pat. No. 7,000,818, the disclosure of which is hereby incorporated by reference in its entirety.

With particular reference to FIG. 3, the distal end of the shaft frame 70 is attached to the staple channel 18. The anvil 22 has a proximal pivoting end 72 that is pivotally received within a proximal end 74 of the staple channel 18, just distal to its engagement to the shaft frame 70. The pivoting end 72 of the anvil 22 includes a closure feature 76 proximate but distal to its pivotal attachment with the staple channel 18. Thus, a closure tube 78, whose distal end includes a horseshoe aperture 80 that engages this closure feature 76, selectively imparts an opening motion to the anvil 22 during proximal longitudinal motion and a closing motion to the anvil 22 during distal longitudinal motion of the closure tube 78 sliding over the shaft frame 70 in response to the closure trigger 40.

The shaft frame 70 encompasses and guides a firing motion from the handle 14 through a longitudinally reciprocating, two-piece knife and firing bar 90. In particular, the shaft frame 70 includes a longitudinal firing bar slot 92 that receives a proximal portion of the two-piece knife and firing bar 90, specifically a laminate tapered firing bar 94. It should be appreciated that the laminate tapered firing bar 94 may be substituted with a solid firing bar or of other materials in applications not intended to pass through an articulation joint, such as depicted in FIGS. 2-14.

An E-beam 102 is the distal portion of the two-piece knife and firing bar 90, which facilitates separate closure and firing as well as spacing of the anvil 22 from the elongate staple channel 18 during firing. With particular reference to FIGS. 3-4, in addition to any attachment treatment such as brazing or an adhesive, the knife and firing bar 90 are formed of a female vertical attachment aperture 104 proximally formed in the E-beam 102 that receives a corresponding male attachment member 106 distally presented by the laminated tapered firing bar 94, allowing each portion to be formed of a selected material and process suitable for their disparate functions (e.g., strength, flexibility, friction). The E-beam 102 may be advantageously formed of a material having suitable material properties for forming a pair of top pins 110, a pair of middle pins 112 and a bottom pin or foot 114, as well as being able to acquire a sharp cutting edge 116. In addition, integrally formed and proximally projecting top guide 118 and middle guide 120 bracketing each vertical end of the cutting edge 116 further define a tissue staging area 122 assisting in guiding tissue to the sharp cutting edge 116 prior to being severed. The middle guide 120 also serves to engage and fire the staple applying apparatus 12 by abutting a stepped central member 124 of a wedge sled 126 (FIG. 5) that effects staple formation by the staple applying assembly 12, as described in greater detail below.

Forming these features (e.g., top pins 110, middle pins 112, and bottom foot 114) integrally with the E-beam 102 facilitates manufacturing at tighter tolerances relative to one another as compared to being assembled from a plurality of parts, ensuring desired operation during firing and/or effective interaction with various lockout features of the staple applying assembly 12.

Figure 6:
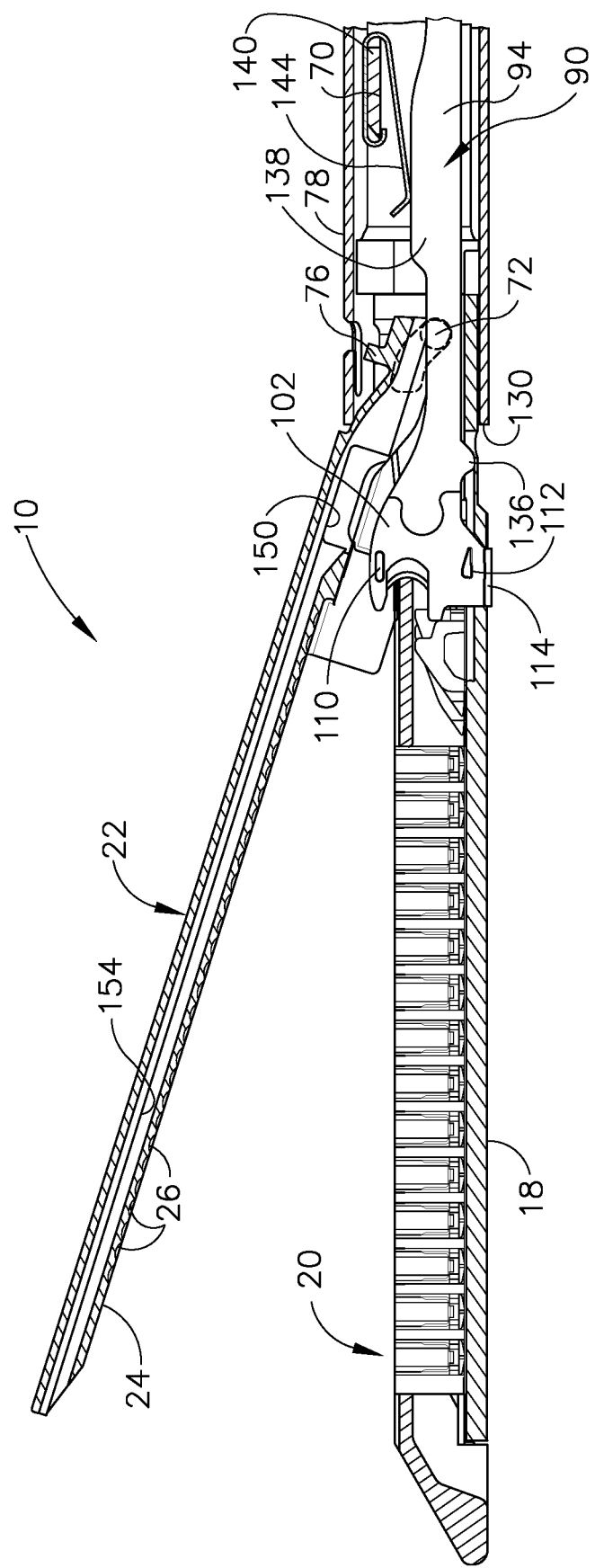
FIG. 6 is a left side view in elevation taken in longitudinal cross section along a centerline line 6-6 of the staple applying assembly of FIG. 2.
Figure 7:
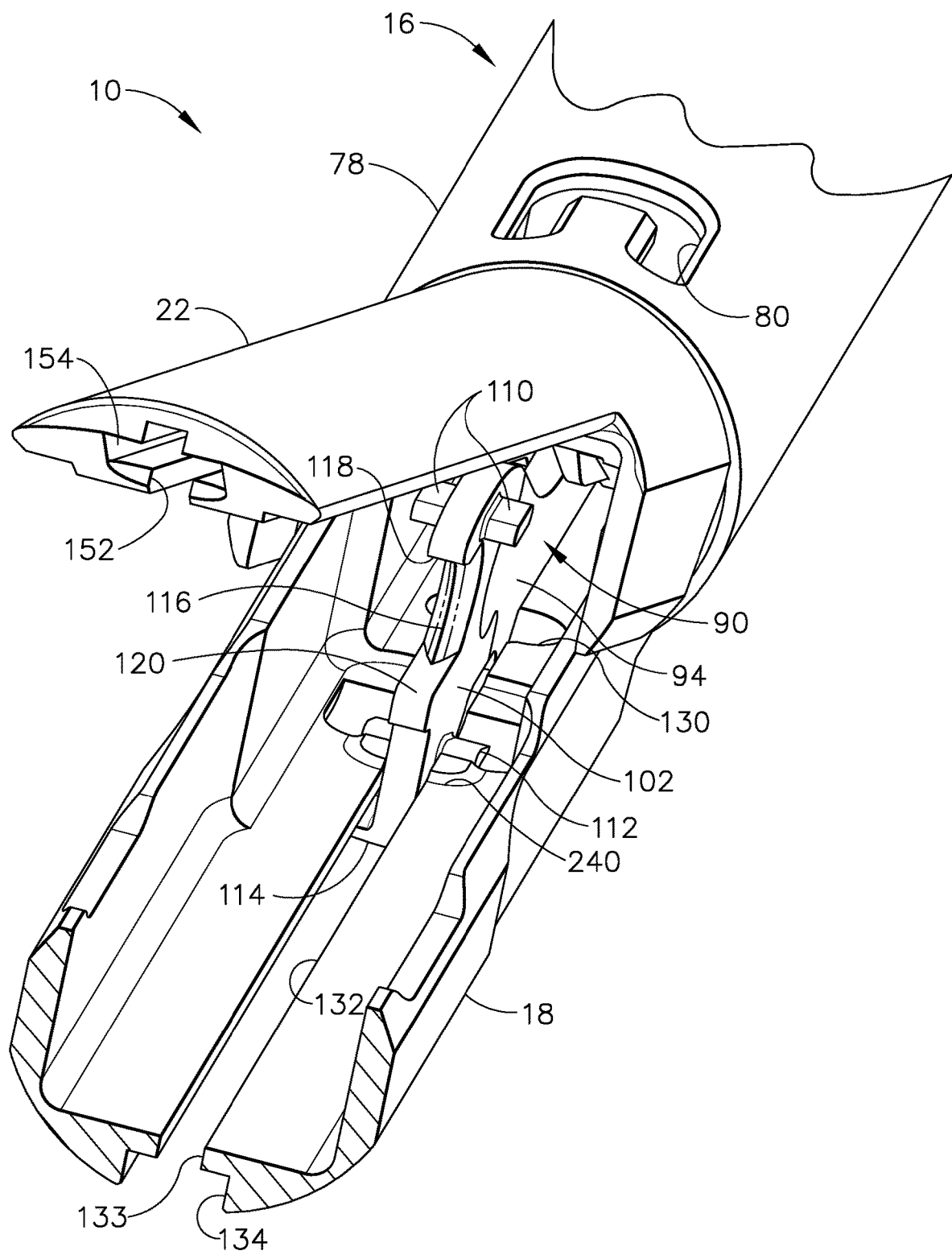
FIG. 7 is a perspective view of the open staple applying assembly of FIG. 2 without the replaceable staple cartridge, a portion of the staple channel proximate to a middle pin of two-piece knife and firing bar, and without a distal portion of a staple channel.

In FIGS. 6-7, the surgical stapling instrument 10 is shown open, with the E-beam 102 fully retracted. During assembly, the lower foot 114 of the E-beam 102 is dropped through a widened hole 130 in the staple channel 18 and the E-beam 102 is then advanced such that the E-beam 102 slides distally along a lower track 132 formed in the staple channel 18. In particular, the lower track 132 includes a narrow slot 133 that opens up as a widened slot 134 on an undersurface of the staple channel 18 to form an inverted T-shape in lateral cross section, as depicted particularly in FIGS. 7 and 8, which communicates with the widened hole 130. Once assembled, the components proximally coupled to the laminate tapered firing bar 94 do not allow the lower foot 114 to proximally travel again to the widened hole 130 to permit disengagement.

In FIG. 9, the laminate tapered firing bar 94 facilitates insertion of the staple applying assembly 12 through a trocar. In particular, a more distal, downward projection 136 raises the E-beam 102 when fully retracted. This is accomplished by placement of the downward projection 136 at a point where it cams upwardly on a proximal edge of the widened hole 130 in the staple channel 18.

In FIG. 10, the laminate tapered firing bar 94 also enhances operation of certain lockout features that may be incorporated into the staple channel 18 by including a more proximal upward projection 138 that is urged downwardly by the shaft frame 70 during an initial portion of the firing travel. In particular, a lateral bar 140 is defined between a pair of square apertures 142 in the shaft frame 70 (FIG. 3).

A clip spring 144 that encompasses the lateral bar 140 downwardly urges a portion of the laminate tapered firing bar 94 projecting distally out of the longitudinal firing bar slot 92, which ensures certain advantageous lockout features are engaged when appropriate. This urging is more pronounced or confined solely to that portion of the firing travel when the upward projection 138 contacts the clip spring 144.

In FIGS. 6-7, the E-beam 102 is retracted with the top pins 110 thereof residing within an anvil pocket 150 near the pivoting proximal end of the anvil 22. A downwardly open vertical anvil slot 152 (FIG. 2) laterally widens in the anvil 22 into an anvil internal track 154 that captures the top pins 110 of the E-beam 102 as they distally advance during firing, as depicted in FIGS. 9-10, affirmatively spacing the anvil 22 from the staple channel 18. Thus, with the E-beam 102 retracted, the surgeon is able to repeatably open and close the staple applying assembly 12 until satisfied with the placement and orientation of tissue captured therein for stapling and severing, yet the E-beam 102 assists in proper positioning of tissue even for a staple applying assembly 12 of reduced diameter and correspondingly reduced rigidity.

Figure 8:
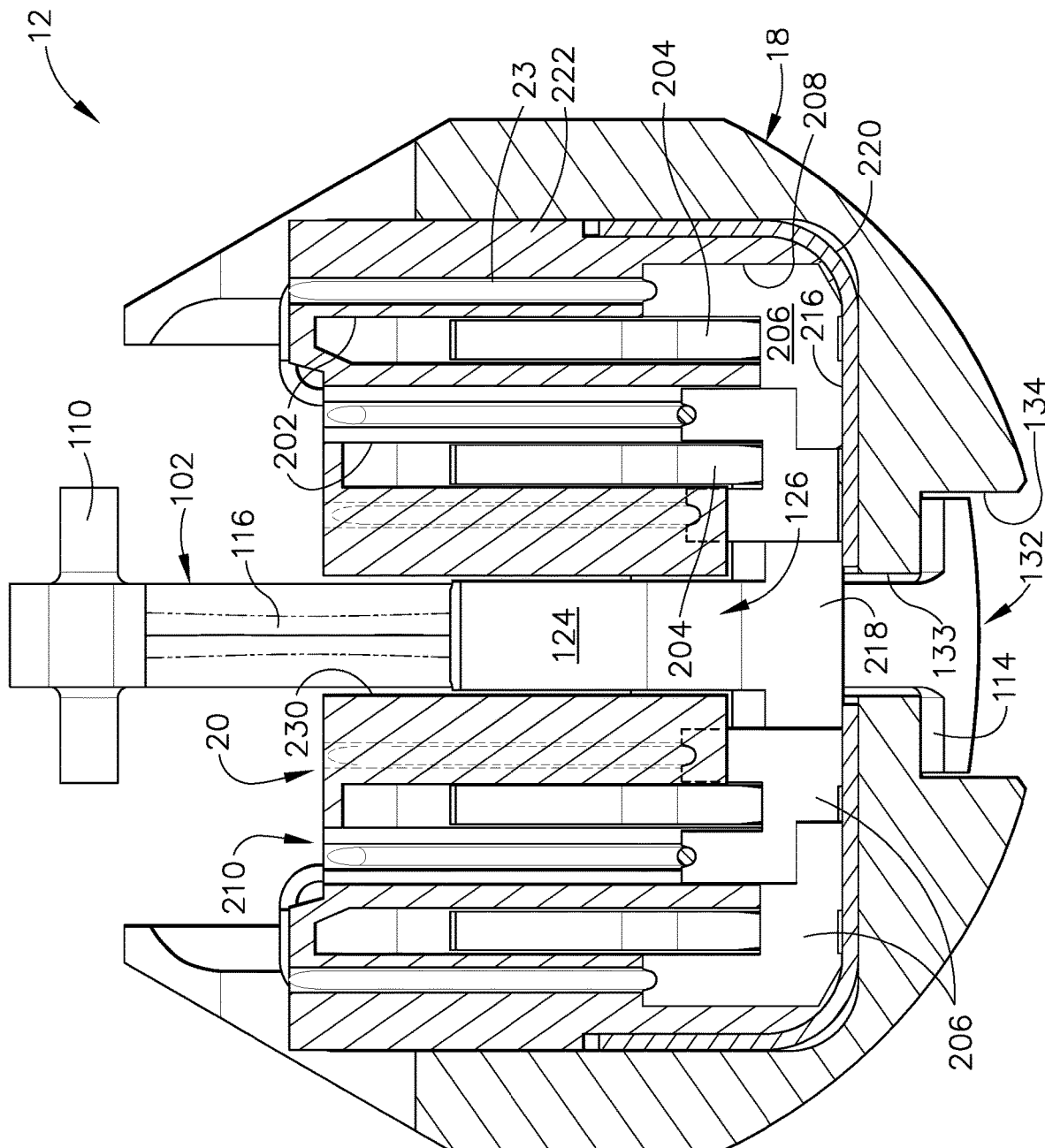
FIG. 8 is a front view in elevation taken in cross section along line 8-8 of the staple applying assembly of FIG. 2 depicting internal staple drivers of the staple cartridge and portions of the two-piece knife and firing bar.

In FIGS. 2-3, 5-6, 8-14, the staple applying assembly 12 is shown with the replaceable staple cartridge 20 that includes the wedge sled 126. Longitudinally aligned and parallel plurality of downwardly open wedge slots 202 (FIG. 8) receive respective wedges 204 integral to the wedge sled 126. In FIGS. 8-10, the wedge sled 126 thus cams upwardly a plurality of staple drivers 206 that are vertically slidable within staple driver recesses 208. In this illustrative version, each staple driver 206 includes two vertical prongs, each translating upwardly into a respective staple hole 210 to upwardly force out and deform a staple 23 resting thereupon against a staple forming surface 214 (FIG. 10) of the anvil 22. A central firing recess 216 (FIG. 3) defined within the staple cartridge 20 proximate to the staple channel 18 allows the passage of the bottom, horizontal portion 218 (FIG. 5) of the wedge sled 126 as well as the middle pins 112 of the E-beam 102. Specifically, a staple cartridge tray 220 (FIGS. 3, 8) attaches to and underlies a polymer staple cartridge body 222 that has the staple driver recesses 208, staple holes 210, and central firing recess 216 formed therein. As staples 23 are thus formed to either side, the sharp cutting edge 116 enters a vertical through slot 230 passing through the longitudinal axis of the staple cartridge 20, excepting only a most distal end thereof.

Firing the staple applying assembly 12 begins as depicted in FIG. 10 with the two-piece knife and firing bar 90 proximally drawn until the downward projection 136 cams the middle guide 120 on the E-beam 102 upward and aft, allowing a new staple cartridge 20 to be inserted into the staple channel 18 when the anvil 22 is open as depicted in FIGS. 2, 6.

Figure 11:
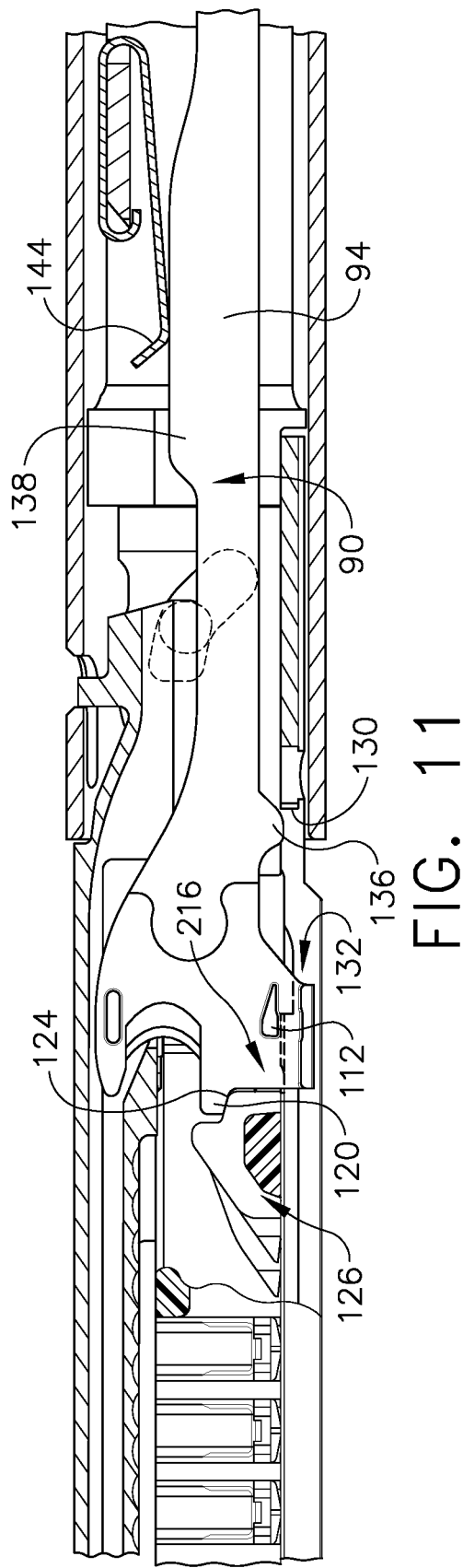
FIG. 11 is a left side detail view in elevation of the staple applying assembly of FIG. 10 with the two-piece knife beginning to fire, corresponding to the configuration depicted in FIG. 9.

In FIG. 11, the two-piece knife and firing bar 90 has been distally advanced a small distance, allowing the downward projection 136 to drop into the widened hole 130 of the lower track 132 under the urging of the clip spring 144 against the upward projection 138 of the laminate tapered firing bar 94. The middle guide 120 prevents further downward rotation by resting upon the stepped central member 124 of the wedge sled 126, thus maintaining the middle pin 112 of the E-beam within the central firing recess 216.

Figure 12:
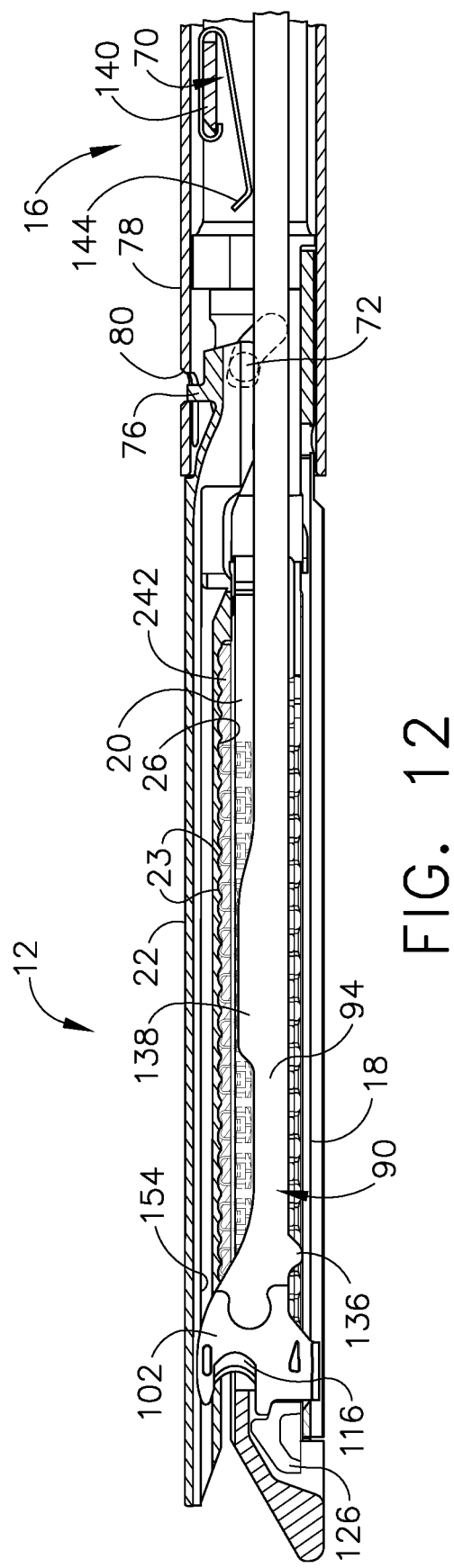
FIG. 12 is a left side cross-sectional view in elevation of the closed staple applying assembly of FIG. 9 after the two-piece knife and firing bar has distally fired.
Figure 15:
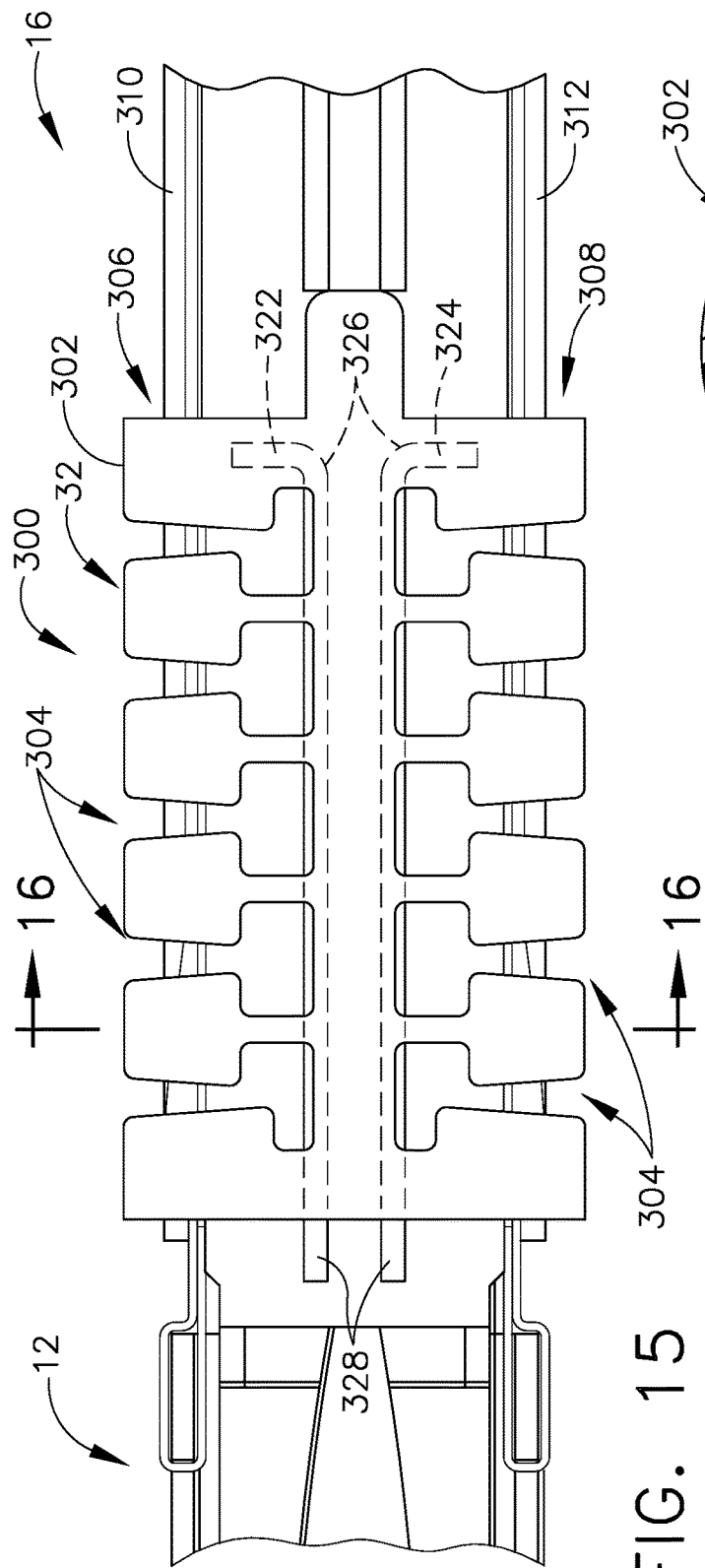
FIG. 15 is a top view in section taken along lines 15-15 of an articulation joint (flex neck) of the surgical stapling instrument of FIG. 1.
Figure 16:
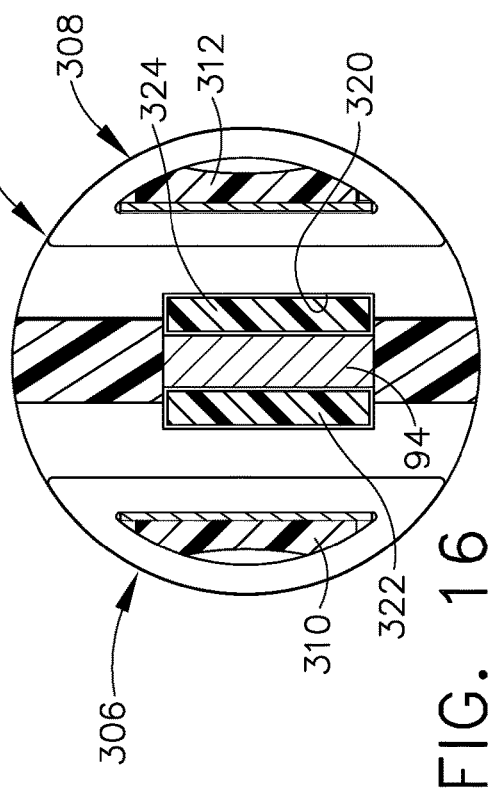
FIG. 16 is a front view in elevation taken in vertical cross section along lines 16-16 of the articulation joint of FIG. 15, showing electroactive polymer (EAP) plate articulation actuators and EAP support plates for a firing bar.
Figure 17:
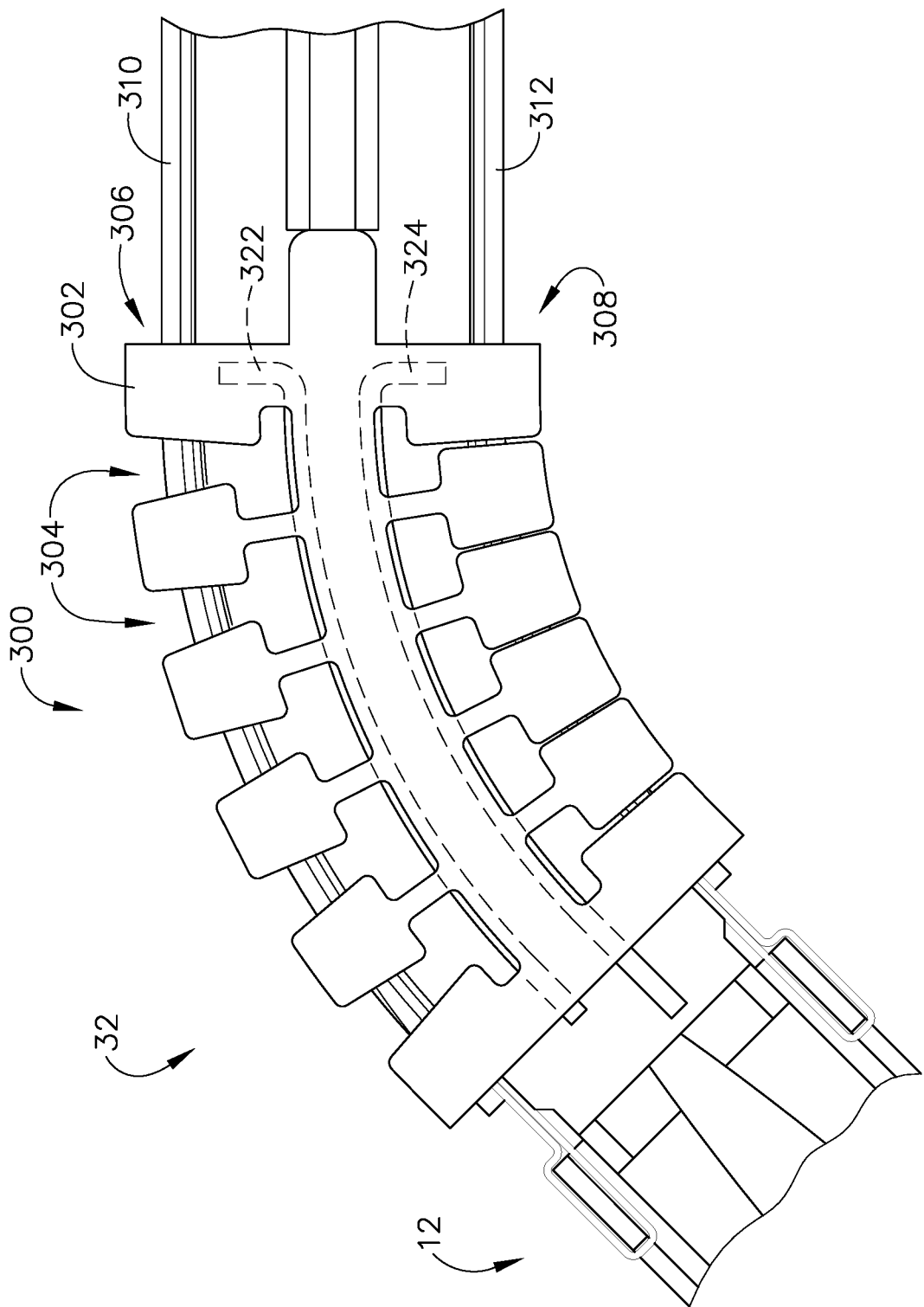
FIG. 17 is a top view in section along lines 15-15 of the articulation joint of FIG. 16 after articulation.
Figure 18:
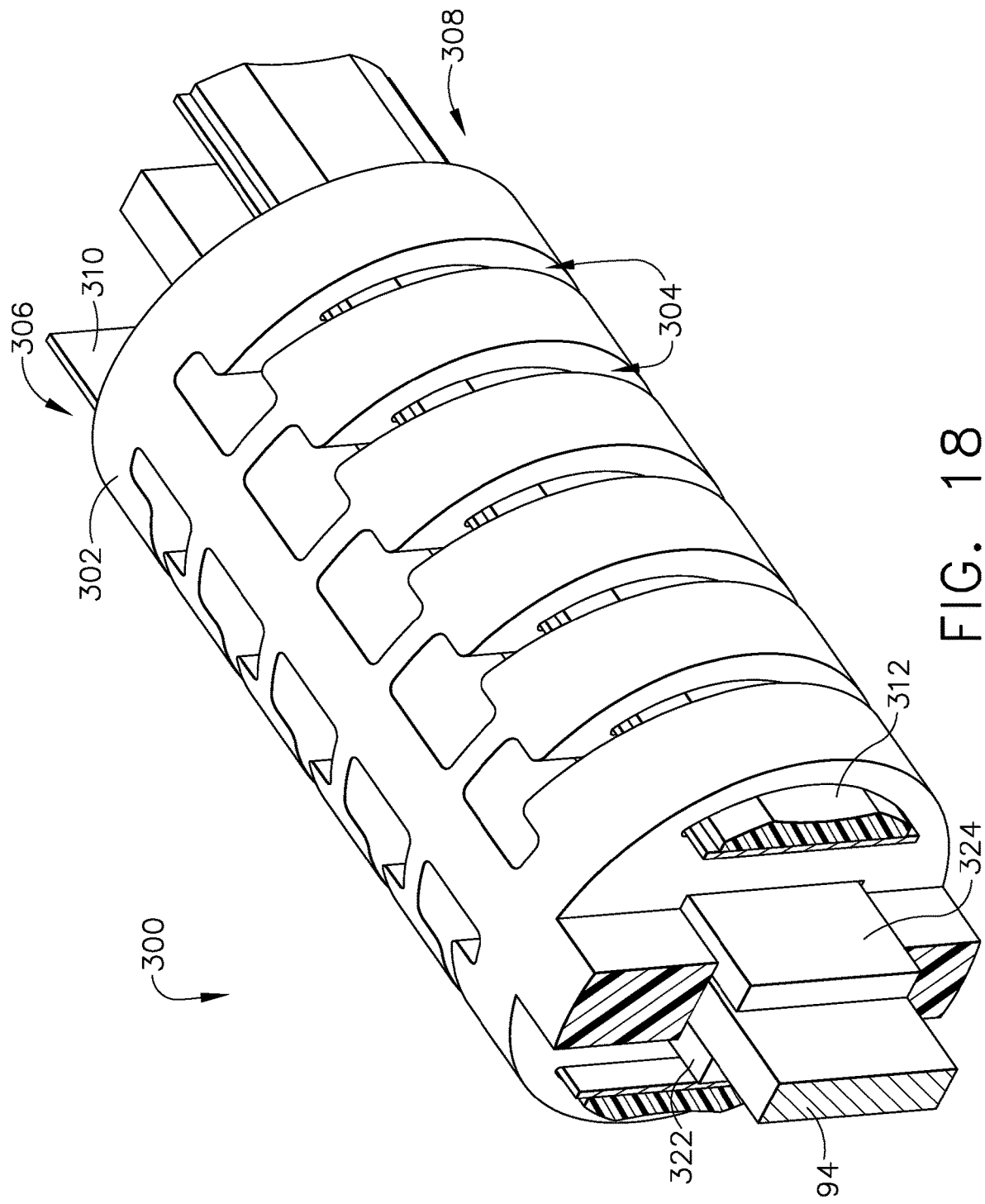
FIG. 18 is a perspective view of the articulation joint of FIG. 15.

In FIG. 12, the two-piece knife and firing bar 90 has been distally fired, advancing the wedge sled 126 to cause formation of staples 23 while severing tissue 242 clamped between the anvil 22 and staple cartridge 20 with the sharp cutting edge 116. Thereafter, in FIG. 13, the two-piece knife and firing bar 90 is retracted, leaving the wedge sled 126 distally positioned.

In FIG. 14, the middle pin 112 is allowed to translate down into a lockout recess 240 formed in the staple channel 18 (also see FIGS. 7, 10). Thus, the operator would receive a tactile indication as the middle pin 112 encounters the distal edge of the lockout recess 240 when the wedge sled 126 (not shown in FIG. 14) is not proximally positioned (i.e., missing staple cartridge 20 or spent staple cartridge 20).

In FIG. 1, an articulation joint 32 is depicted that advantageously benefits from the flexible strength of the two-piece knife and firing bar 90. In FIGS. 15-18, the articulation joint 32 is depicted as a flex neck joint 300 formed by vertebral column body 302 having laterally symmetric pairs of arcing recesses 304 that allow articulation in an articulation plane. It is generally known to simultaneously compress and expand respective lateral sides 306, 308 by selective movement of control rods (not shown) that longitudinally pass through the respective lateral sides 306, 308. Depicted, however, are EAP plate actuators 310, 312, each capable of powered deflection to one or both lateral directions.

A central passage 320 (FIG. 16) defined longitudinally through the vertebral column body 302 receives a pair of support plates 322, 324 that prevent buckling and binding of the laminate tapered firing bar 94. In the illustrative version, each support plate 322, 324 has a proximal fixed end 326 (FIG. 15) and a sliding end 328 to accommodate changes in radial distance during articulation. Having a firing bar 94 of a thinner thickness is thus supported.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while there are a number of advantages to having a wedge sled integral to a staple cartridge, in some applications consistent with aspects of the present invention, the wedge sled may be integral instead to an E-beam. For instance, an entire end effector may be replaceable rather than just the staple cartridge.

What is claimed is:

1. A surgical instrument, comprising:
   an end effector, comprising:
      an elongate channel; and
      an anvil operably coupled to said elongate channel, wherein said anvil and said elongate channel are configurable between an open configuration and a closed configuration, and wherein said anvil comprises an anvil slot;
   a distal beam head movable between a proximal position and a distal position, wherein said distal beam head comprises:
      a cutting edge;
      an upper flange configured to slidably engage said anvil; and
      a lower flange configured to slidably engage said elongate channel, wherein said upper flange and said lower flange are configured to affirmatively space said elongate channel and said anvil as said distal beam head moves toward said distal position;
   an articulation joint;
   a firing bar configured to transfer a firing motion to said distal beam head through said articulation joint, wherein said firing bar comprises a plurality of laminated strips, and wherein a thickness of said distal beam head is greater than a thickness of at least two strips of said plurality of laminated strips; and
   a joint, wherein said firing bar is connected to said distal beam head at said joint.

2. The surgical instrument of claim 1, further comprising an elongate shaft, wherein said end effector is rotatable relative to said elongate shaft about said articulation joint.

3. The surgical instrument of claim 1, further comprising a closure driver movable between a first position and a second position, wherein said anvil and said elongate channel are configured to transition toward said closed configuration based on said closure driver moving toward said second position.

4. The surgical instrument of claim 1, wherein said distal beam head comprises an aperture, wherein said firing bar comprises an attachment member, and wherein said attachment member is positioned within said aperture to couple said distal beam head to said firing bar.

5. The surgical instrument of claim 1, wherein said firing bar is tapered.

6. The surgical instrument of claim 1, wherein said end effector further comprises a staple cartridge, and wherein said staple cartridge comprises a stepped deck.

7. The surgical instrument of claim 1, wherein said end effector further comprises a staple cartridge, and wherein said staple cartridge is replaceable.

8. The surgical instrument of claim 1, wherein said distal beam head is comprised of a first material, and wherein said firing bar is comprised of a second material different than said first material.

9. A surgical system, comprising:
   an end effector, comprising:
      an elongate channel; and
      an anvil operably coupled to said elongate channel, wherein said anvil and said elongate channel are configurable between an open configuration and a clamped configuration, and wherein said anvil comprises an anvil slot; and
   a beam head movable between an unfired position and a fired position, wherein said beam head comprises:
      a knife;
      a first pin configured to slidably engage said anvil; and
      a second pin configured to slidably engage said elongate channel, wherein said first pin and said second pin are configured to maintain said elongate channel and said anvil in said clamped configuration as said beam head moves toward said fired position;
   an articulation joint;
   a firing bar configured to transfer a firing motion to said beam head through said articulation joint, wherein said firing bar comprises a plurality of laminated strips; and
   a joint, wherein said firing bar is connected to said beam head at said joint.

10. The surgical system of claim 9, further comprising an elongate shaft, wherein said end effector is rotatable relative to said elongate shaft about said articulation joint.

11. The surgical system of claim 9, further comprising a clamping driver movable between a first position and a second position, wherein said anvil and said elongate channel are configured to transition toward said clamped configuration based on said clamping driver moving toward said second position.

12. The surgical system of claim 9, wherein said beam head comprises an aperture, wherein said firing bar comprises an attachment member, and wherein said attachment member is positionable within said aperture to couple said beam head to said firing bar.

13. The surgical system of claim 9, wherein said firing bar is tapered.

14. The surgical system of claim 9, wherein said end effector further comprises a fastener cartridge, and wherein said fastener cartridge comprises a stepped deck.

15. The surgical system of claim 9, wherein said end effector further comprises a fastener cartridge, and wherein said fastener cartridge is replaceable.

16. A surgical system, comprising:
an end effector, comprising:
  a first jaw; and
  a second jaw, wherein said first jaw and said second jaw are configurable between an open configuration and a closed configuration, and wherein said second jaw comprises a second jaw slot;
a beam head movable between a starting position and an ending position, wherein said beam head comprises:
  a blade;
  a first arm configured to slidably engage said first jaw; and
  a second arm configured to slidably engage said second jaw, wherein said first arm and said second arm are configured to maintain a spacing between said first jaw and said second jaw as said beam head moves toward said ending position;
an articulation joint; and
a firing bar configured to transfer a firing motion to said beam head through said articulation joint, wherein said firing bar comprises a plurality of laminated strips; and
a joint, wherein said firing bar is connected to said beam head at said joint.

17. The surgical system of claim 16, further comprising an elongate shaft, wherein said end effector is rotatable relative to said elongate shaft about said articulation joint.

18. The surgical system of claim 16, further comprising a closure driver movable between a first position and a second position, wherein said first jaw and said second jaw are configured to transition toward said closed configuration based on said closure driver moving toward said second position.

19. The surgical system of claim 16, wherein said firing bar is tapered.

20. The surgical system of claim 16, wherein said end effector further comprises a staple cartridge, and wherein said staple cartridge comprises a stepped deck.

21. The surgical system of claim 16, wherein said end effector further comprises a staple cartridge, and wherein said staple cartridge is replaceable.

\* \* \* \* \*